United States Patent
Tang et al.

(10) Patent No.: US 7,425,625 B2
(45) Date of Patent: *Sep. 16, 2008

(54) CAROTENOID KETOLASE GENES WITH IMPROVED KETOCAROTENOID YIELD

(75) Inventors: Xiao-Song Tang, Hockessin, DE (US);
Qiong Cheng, Wilmington, DE (US);
Luan Tao, Havertown, PA (US); Joanne Y. Shyr, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/147,915

(22) Filed: Jun. 8, 2005

(65) Prior Publication Data
US 2006/0003403 A1    Jan. 5, 2006

Related U.S. Application Data

(60) Provisional application No. 60/577,970, filed on Jun. 8, 2004.

(51) Int. Cl.
*C07H 21/04* (2006.01)
*C12P 1/00* (2006.01)

(52) U.S. Cl. ........................ 536/23.2; 435/41
(58) Field of Classification Search ........................ None
See application file for complete search history.

(56) References Cited

U.S. PATENT DOCUMENTS

| | | |
|---|---|---|
| 5,916,791 A | 6/1999 | Hirschberg et al. |
| 5,965,795 A | 10/1999 | Hirschberg et al. |
| 6,218,599 B1 | 4/2001 | Hirschberg et al. |
| 7,074,604 B1 * | 7/2006 | Tang et al. .................. 435/189 |

FOREIGN PATENT DOCUMENTS

| | | |
|---|---|---|
| CN | 1380415 A | 11/2002 |
| FR | 2 792 335 | 10/2000 |
| WO | WO 99/07867 | 2/1999 |
| WO | WO 00/61764 | 10/2000 |
| WO | WO 02/079395 A2 | 10/2002 |

OTHER PUBLICATIONS

Kawarabayasi et al. (2001) DNA Research, vol. 8, p. 123-140.*
Mann et al. (2000) Nature Biotechnology, vol. 18, p. 888-892.*
U.S. Appl. No. 10/209,372, filed Jul. 30, 2002, Cheng et al.
G. Armstrong, Carotenoid Genetics and Biochemistry, Comprehensive Natural Products Chemistry, Elsevier Press, vol. 2:321-352, 1999.
Laure Hannibal et al., Isolation and Characterization of Canthaxanthin Biosynthesis Genes from the Photosynthetic Bacterium Bradyrhizoblum sp. Strain ORS278, Journal of Bacteriology, vol. 182(13):3850-3853, 2000.

(Continued)

*Primary Examiner*—Kathleen Kerr Bragdon
*Assistant Examiner*—Alexander D Kim

(57) ABSTRACT

Protein engineered CrtO ketolases isolated from *Rhodococcus erythropolis* AN12 are provided having increased carotenoid ketolase activity. Methods using the present CrtO ketolases are also provided for increasing ketocarotenoid production in suitable production hosts.

24 Claims, 2 Drawing Sheets

Common carotenoids produced by ketolase together with hydroxylase

OTHER PUBLICATIONS

Norihiko Misawa et al., Structure and Functional Analysis of a Marine Bacterial Carotenoid Biosynthesis Gene Cluster and Astaxanthin Biosynthetic Pathway Proposed at the Gene Level, Journal of Bacteriology, vol. 177(22):6575-6584, Nov. 1995.

Zairen Sun et al., Differential expression of two isopentenyl pyrophosphate isomerases and enhanced carotenoid accumulation in a unicellular chlorophyte, PNAS, vol. 95:11482-11488, 1998.

Jurgen Breitenbach et al., Expression in *Escherichia coli* and properties of the carotene ketolase from *Haematococcus pluvialis*, FEMS Microbiology Letters, vol. 140:241-246, 1996.

Delphine Lagarde et al., Increased Production of Zeaxanthin and Other Pigments by Application of Genetic Engineering Techniques to Synechocystis sp. Strain PCC 6803, Applied and Environmental Microbiology, vol. 66(1):64-72, 2000.

Kazumori Masamoto et al., beta-Carotene Hydroxylase Gene from the Cyanobacterium Synechocystis sp. PCC6803, Plant Cell Physiol., vol. 39(5):560-564, 1998.

Yasukazu Nakamura et al., Complete Genome Structure of *Gloeobacter violaceus* PCC 7421, a Cyanobacterium that Lacks Thylakoids (Supplement), DNA Research, vol. 10-Supplement:181-201, 2003.

Mark Harker et al., Biosynthesis of ketocarotenoids in transgenic cyanobacteria expressing the algal gene for beta-C-4-oxygenase, crtO, FEBS Letters, vol. 404:129-134, 1997.

Burnett, William V. et al., The nucleotide sequence of the gene encoding for XP55, a major secreted protein from *Streptomyces lividans*, Nucleic Acids Research, 1987, p. 3926, vol. 16, No. 9.

Kawarabayasi, Yutaka et al., Complete Genome Sequence of an Aerobic Thermoacidophilic Crenarchaeon, *Sulfolobus tokodaii* strain 7, DNA Research, 2001, p. 123-140, vol. 8.

Mann, Varda et al., Metabolic engineering os astaxanthin production in tobacco flowers, Nature Biotechnology, Aug. 2000, p. 888-892, vol. 18.

International Search Report dated Nov. 23, 2007, International Application No. PCT/2005/20411, International Filing date Jun. 8, 2005.

* cited by examiner

```
                        SEQUENCE LISTING

<160> NUMBER OF SEQ ID NOS: 52

<210> SEQ ID NO 1
<211> LENGTH: 1599
<212> TYPE: DNA
<213> ORGANISM: Rhodococcus erythropolis AN12
<220> FEATURE:
<221> NAME/KEY: CDS
<222> LOCATION: (1)..(1599)

<400> SEQUENCE: 1 gtg agc gca ttt ctc gac gcc gtc gtc gtc ggt tcc gga cac aac gcg      48
Val Ser Ala Phe Leu Asp Ala Val Val Val Gly Ser Gly His Asn Ala
1               5                   10                  15 ctc gtt tcg gcc gcg tat ctc gca cgt gag ggt tgg tcg gtc gag gtt      96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc     288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc     336
Thr Asp Gly Pro Gly Ile Val Phe His Arg Asp Leu Asp Ala Thr Cys
                100                 105                 110 cag tcc atc gaa cga gct tgc ggg aca aag gac gcc gac gcg tac cgg     384
Gln Ser Ile Glu Arg Ala Cys Gly Thr Lys Asp Ala Asp Ala Tyr Arg
            115                 120                 125 cgg ttc gtc gcg gtc tgg tcg gag cgc agc cga cac gtg atg aag gca     432
Arg Phe Val Ala Val Trp Ser Glu Arg Ser Arg His Val Met Lys Ala
        130                 135                 140 ttt tcc aca ccg ccc acc gga tcg aac ctg atc ggt gcg ttc gga gga     480
Phe Ser Thr Pro Pro Thr Gly Ser Asn Leu Ile Gly Ala Phe Gly Gly
145                 150                 155                 160 ctg gcc aca gcg cgc ggc aac agc gaa ctg tcg cgg cag ttc ctc gcg     528
Leu Ala Thr Ala Arg Gly Asn Ser Glu Leu Ser Arg Gln Phe Leu Ala
                165                 170                 175
```

```
ccg ggc gac gca ctg ctg gac gag tat ttc gac agt gag gca ctc aag    576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa    624
Ala Ala Leu Ala Trp Phe Gly Ala Gln Ser Gly Pro Pro Met Ser Glu
            195                 200                 205 ccg gga acc gct ccg atg gtc ggc ttc gcg gcc ctc atg cac gtc ctg    672
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg    720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc    768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag    816
Val Thr Ser Ile Arg Arg Asn Ser Asn His Trp Thr Val Thr Thr Glu
        260                 265                 270 agc ggt cga gaa gtt cac gct cgc aag gta atc gcg ggt tgc cac atc    864
Ser Gly Arg Glu Val His Ala Arg Lys Val Ile Ala Gly Cys His Ile
    275                 280                 285 ctc acg aca ctc gat ctc ctg ggc aac gga ggc ttc gac cga acc acg    912
Leu Thr Thr Leu Asp Leu Leu Gly Asn Gly Gly Phe Asp Arg Thr Thr
    290                 295                 300 ctc gat cac tgg cgg cgg aag atc agg gtc ggc ccc ggc atc ggc gct    960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc   1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc   1056
Thr Thr Arg Glu Ser Thr Ser Gly Leu Gln Leu Leu Val Ser Asp Arg
        340                 345                 350 gcc cac ttg cgc act gca cac ggc gca gca ctg gca ggg gaa ctg cct   1104
Ala His Leu Arg Thr Ala His Gly Ala Ala Leu Ala Gly Glu Leu Pro
    355                 360                 365 cct cgc cct gcg gtt ctc gga atg agt ttc agc gga atc gat ccc acg   1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag   1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc   1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc   1296
Glu Ala Asp Arg Ile Val Gly Glu Met Glu Ala Phe Ala Pro Gly Phe
        420                 425                 430 acc gat tcc gtc ctc gac cgc ttc att caa act ccc cgc gac atc gag   1344
Thr Asp Ser Val Leu Asp Arg Phe Ile Gln Thr Pro Arg Asp Ile Glu
    435                 440                 445 tcg gaa ttg ggg atg atc ggc gga aat gtc atg cac gtc gag atg tca   1392
Ser Glu Leu Gly Met Ile Gly Gly Asn Val Met His Val Glu Met Ser
    450                 455                 460 ctc gat cag atg atg ttg tgg cga ccg ctt ccc gaa ctg tcc ggc cat   1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat   1488
Arg Val Pro Gly Ala Asp Gly Leu Tyr Leu Thr Gly Ala Ser Thr His
                485                 490                 495
```

```
ccc ggt ggt ggt gtg tcc gga gcc agt ggt cgc agt gcc gct cga atc    1536
Pro Gly Gly Gly Val Ser Gly Ala Ser Gly Arg Ser Ala Ala Arg Ile
        500                 505                 510 gca ctg tcc gac agc cgc cgg ggt aaa gcg agt cag tgg atg cgt cgt    1584
Ala Leu Ser Asp Ser Arg Arg Gly Lys Ala Ser Gln Trp Met Arg Arg
    515                 520                 525 tcg agc agg tcg tga                                                 1599
Ser Ser Arg Ser
    530

<210> SEQ ID NO 2
<211> LENGTH: 532
<212> TYPE: PRT
<213> ORGANISM: Rhodococcus erythropolis AN12

<400> SEQUENCE: 2

Val Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg
        35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
    130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
```

-continued

```
         305                 310                 315                 320
Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
        435                 440                 445

Ser Glu Leu Gly Met Ile Gly Gly Asn Val Met His Val Glu Met Ser
    450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Met Arg Arg
        515                 520                 525

Ser Ser Arg Ser
    530
```

```
<210> SEQ ID NO 3
<211> LENGTH: 1599
<212> TYPE: DNA
<213> ORGANISM: artificial sequence
<220> FEATURE:
<223> OTHER INFORMATION: crt0319

<400> SEQUENCE: 3
atgagcgcct tcctggacgc ggtcgtggtc ggcagcggtc ataacgccct ggtcagcgcc     60
gcctatctgg cccgcgaagg ctggagcgtc gaagtcctgg aaaaggacac cgtcctgggt    120
ggcgccgtca gcaccgtcga acgcttcccg ggctacaaag tcgaccgcgg cagcagcgcc    180
catctgatga tccgccatag cggcatcatc gaagaactgg gtctgggtgc acatggcctg    240
cgttacatcg actgcgaccc gtgggccttt gctccgcctg caccgggtac cgatggtcct    300
ggtatcgtct tccaccgtga cctggacgcc acctgccaaa gcatcgaacg cgcctgcggt    360
accaaagacg ccgatgccta tgtcgcttc gtcgccgtct ggtcggaacg cagccgccat    420
gtcatgaaag ccttcagcac ccctccgacc ggtagcaacc tgatcggtgc gtttggtggc    480
ctggcgaccg cacgtggtaa cagcgaactg tcccgtcaat tcctggctcc gggtgacgcc    540
ttgctggacg aatacttcga ctccgaagcc ctgaaagccg ctctggcctg gtttggtgct    600
caatccggtc ctccgatgtc cgaacctggc accgctccta tggtcggctt cgccgctttg    660
atgcatgtct gccgccagg tcgtgctgtg ggtggctccg gtcgctgtc ggcagccctg    720
gcgtcccgca tggccgtcga tggtgcgacc gtcgccctgg gtgatggtgt caccagcatc    780
```

```
cgtcgcaaca gcaaccattg gaccgtcacc accgaaagcg gccgtgaagt ccatgcccgc    840
aaagtcatcg ccggctgcca tatcctgacc accttggact tgctgggcaa cggtggcttc    900
gatcgcacca ctctggacca ttggcgtcgt aagatccgtg tcggtccagg catcggtgcc    960
gtcctgcgtc tggccaccag cgccttgccg agctatcgtg gtgatgccac cacccgcgaa   1020
agcacctccg gtctgcaact gctggtcagc gaccgtgccc atctgcgtac cgcgcatggc   1080
gctgccttgg ctggtgaact gccaccgcgt cctgctgtcc tgggcatgag cttcagcggc   1140
atcgatccga cgattgctcc ggccggtcgt catcaagtca ccctgtggag ccaatggcaa   1200
ccgtatcgcc tgagcggtca tcgtgactgg gccagcgtcg ctgaagccga agccgaccgt   1260
atcgtgggtg aaatggaagc tttcgctccg ggtttcaccg actccgtcct ggaccgcttc   1320
atccaaacgc cgcgtgatat cgaaagcgaa ctgggtatga tcggcggtaa cgtcatgcat   1380
gtcgagatga gcctggacca aatgatgctg tggcgtccgt tgccggaact gtcgggccac   1440
cgcgtgccgg gtgccgatgg cctgtatctg acgggtgcca gcacccatcc gggtggtggc   1500
gtctcgggtg cctccggtcg cagcgccgcc cgcattgccc tgagcgacag ccgccgcggc   1560
aaagccagcc aatggatgcg tcgcagcagc cgtagctaa                          1599
```

<210> SEQ ID NO 4
<211> LENGTH: 1608
<212> TYPE: DNA
<213> ORGANISM: artificial sequence
<220> FEATURE:
<223> OTHER INFORMATION: crtO303
<220> FEATURE:
<221> NAME/KEY: CDS
<222> LOCATION: (1)..(1608)

<400> SEQUENCE: 4

```
atg gcc ctt atg agc gca ttt ctc gac gcc gtc gtc gtc ggt tcc gga      48
Met Ala Leu Met Ser Ala Phe Leu Asp Ala Val Val Val Gly Ser Gly
1               5                   10                  15 cac aac gcg ctc gtt tcg gcc gcg tat ctc gca cgt gag ggt tgg tcg      96
His Asn Ala Leu Val Ser Ala Ala Tyr Leu Ala Arg Glu Gly Trp Ser
                20                  25                  30 gtc gag gtt ctc gag aag gac acg gtt ctc ggc ggt gcc gtc tcg acc     144
Val Glu Val Leu Glu Lys Asp Thr Val Leu Gly Gly Ala Val Ser Thr
            35                  40                  45 gtc gag cga ttt ccc gga tac aag gtg gac cgg ggg tcg tct gcg cac     192
Val Glu Arg Phe Pro Gly Tyr Lys Val Asp Arg Gly Ser Ser Ala His
        50                  55                  60 ctc atg atc cga cac agt ggc atc atc gag gaa ctc gga ctc ggc gcg     240
Leu Met Ile Arg His Ser Gly Ile Ile Glu Glu Leu Gly Leu Gly Ala
65                  70                  75                  80 cac ggc ctt cgc tac atc gac tgt gac ccg tgg gcg ttc gct ccg ccc     288
His Gly Leu Arg Tyr Ile Asp Cys Asp Pro Trp Ala Phe Ala Pro Pro
                85                  90                  95 gcc cct ggc acc gac ggg ccg ggc atc gtg ttt cat cgc gac ctc gat     336
Ala Pro Gly Thr Asp Gly Pro Gly Ile Val Phe His Arg Asp Leu Asp
                100                 105                 110 gca acc tgc cag tcc atc gaa cga gct tgc ggg aca aag gac gcc gac     384
Ala Thr Cys Gln Ser Ile Glu Arg Ala Cys Gly Thr Lys Asp Ala Asp
            115                 120                 125 gcg tac cgg cgg ttc gtc gcg gtc tgg tcg gag cgc agc cga cac gtg     432
Ala Tyr Arg Arg Phe Val Ala Val Trp Ser Glu Arg Ser Arg His Val
        130                 135                 140 atg aag gca ttt tcc aca ccg ccc acc gga tcg aac ctg atc ggt gcg     480
```

```
Met Lys Ala Phe Ser Thr Pro Pro Thr Gly Ser Asn Leu Ile Gly Ala
145                 150                 155                 160 ttc gga gga ctg gcc aca gcg cgc ggc aac agc gaa ctg tcg cgg cag    528
Phe Gly Gly Leu Ala Thr Ala Arg Gly Asn Ser Glu Leu Ser Arg Gln
                165                 170                 175 ttc ctc gcg ccg ggc gac gca ctg ctg gac gag tat ttc gac agt gag    576
Phe Leu Ala Pro Gly Asp Ala Leu Leu Asp Glu Tyr Phe Asp Ser Glu
                180                 185                 190 gca ctc aag gca gcg ttg gcg tgg ttc ggc gcc cag tcc ggg cct ccg    624
Ala Leu Lys Ala Ala Leu Ala Trp Phe Gly Ala Gln Ser Gly Pro Pro
                195                 200                 205 atg tcg gaa ccg gga acc gct ccg atg gtc ggc ttc gcg gcc ctc atg    672
Met Ser Glu Pro Gly Thr Ala Pro Met Val Gly Phe Ala Ala Leu Met
    210                 215                 220 cac gtc ctg ccg ccc ggg cga gca gtc gga ggg agc ggc gca ctg agt    720
His Val Leu Pro Pro Gly Arg Ala Val Gly Gly Ser Gly Ala Leu Ser
225                 230                 235                 240 gct gcg ttg gca tcc cgg atg gct gtc gac ggc gcc acc gtc gcg ctc    768
Ala Ala Leu Ala Ser Arg Met Ala Val Asp Gly Ala Thr Val Ala Leu
                245                 250                 255 ggt gac ggc gtg acg tcg atc cgc cgg aac tcg aat cac tgg acc gtc    816
Gly Asp Gly Val Thr Ser Ile Arg Arg Asn Ser Asn His Trp Thr Val
                260                 265                 270 aca acc gag agc ggt cga gaa gtt cac gct cgc aag gta atc gcg ggt    864
Thr Thr Glu Ser Gly Arg Glu Val His Ala Arg Lys Val Ile Ala Gly
                275                 280                 285 tgc cac atc ctc acg aca ctc gat ctc ctg ggc aac gga ggc ttc gac    912
Cys His Ile Leu Thr Thr Leu Asp Leu Leu Gly Asn Gly Gly Phe Asp
    290                 295                 300 cga acc acg ctc gat cac tgg cgg cgg aag atc agg gtc ggc ccc ggc    960
Arg Thr Thr Leu Asp His Trp Arg Arg Lys Ile Arg Val Gly Pro Gly
305                 310                 315                 320 atc ggc gct gta ttg cga ctg gcg aca tct gcg ctc ccg tcc tac cgc   1008
Ile Gly Ala Val Leu Arg Leu Ala Thr Ser Ala Leu Pro Ser Tyr Arg
                325                 330                 335 ggc gac gcc acg aca cgg gaa agt acc tcg gga ttg caa tta ctc gtt   1056
Gly Asp Ala Thr Thr Arg Glu Ser Thr Ser Gly Leu Gln Leu Leu Val
                340                 345                 350 tcc gat cgc gcc cac ttg cgc act gca cac ggc gca gca ctg gca ggg   1104
Ser Asp Arg Ala His Leu Arg Thr Ala His Gly Ala Ala Leu Ala Gly
                355                 360                 365 gaa ctg cct cct cgc cct gcg gtt ctc gga atg agt ttc agc gga atc   1152
Glu Leu Pro Pro Arg Pro Ala Val Leu Gly Met Ser Phe Ser Gly Ile
                370                 375                 380 gat ccc acg atc gcc ccg gcc ggg cgg cat cag gtg aca ctg tgg tcg   1200
Asp Pro Thr Ile Ala Pro Ala Gly Arg His Gln Val Thr Leu Trp Ser
385                 390                 395                 400 cag tgg cag ccg tat cgt ctc agc gga cat cgc gat tgg gcg tcg gtc   1248
Gln Trp Gln Pro Tyr Arg Leu Ser Gly His Arg Asp Trp Ala Ser Val
                405                 410                 415 gcc gag gcc gag gcc gac cgg atc gtc ggc gag atg gag gct ttt gca   1296
Ala Glu Ala Glu Ala Asp Arg Ile Val Gly Glu Met Glu Ala Phe Ala
                420                 425                 430 ccc gga ttc acc gat tcc gtc ctc gac cgc ttc att caa act ccc cgc   1344
Pro Gly Phe Thr Asp Ser Val Leu Asp Arg Phe Ile Gln Thr Pro Arg
                435                 440                 445 gac atc gag tcg gaa ttg ggg atg atc ggc gga aat gtc atg cac gtc   1392
Asp Ile Glu Ser Glu Leu Gly Met Ile Gly Gly Asn Val Met His Val
450                 455                 460
```

-continued

```
gag atg tca ctc gat cag atg atg ttg tgg cga ccg ctt ccc gaa ctg      1440
Glu Met Ser Leu Asp Gln Met Met Leu Trp Arg Pro Leu Pro Glu Leu
465                 470                 475                 480 tcc ggc cat cgc gtt ccg gga gca gac ggg ttg tat ctg acc gga gcc      1488
Ser Gly His Arg Val Pro Gly Ala Asp Gly Leu Tyr Leu Thr Gly Ala
                485                 490                 495 tcg acg cat ccc ggt ggt ggt gtg tcc gga gcc agt ggt cgc agt gcc      1536
Ser Thr His Pro Gly Gly Gly Val Ser Gly Ala Ser Gly Arg Ser Ala
            500                 505                 510 gct cga atc gca ctg tcc gac agc cgc cgg ggt aaa gcg agt cag tgg      1584
Ala Arg Ile Ala Leu Ser Asp Ser Arg Arg Gly Lys Ala Ser Gln Trp
        515                 520                 525 atg cgt cgt tcg agc cgc tcg tga                                      1608
Met Arg Arg Ser Ser Arg Ser
    530                 535

<210> SEQ ID NO 5
<211> LENGTH: 535
<212> TYPE: PRT
<213> ORGANISM: artificial sequence
<220> FEATURE:
<223> OTHER INFORMATION: Synthetic Construct

<400> SEQUENCE: 5
```

Met Ala Leu Met Ser Ala Phe Leu Asp Ala Val Val Gly Ser Gly
1               5                   10                  15

His Asn Ala Leu Val Ser Ala Ala Tyr Leu Ala Arg Glu Gly Trp Ser
                20                  25                  30

Val Glu Val Leu Glu Lys Asp Thr Val Leu Gly Gly Ala Val Ser Thr
            35                  40                  45

Val Glu Arg Phe Pro Gly Tyr Lys Val Asp Arg Gly Ser Ser Ala His
        50                  55                  60

Leu Met Ile Arg His Ser Gly Ile Ile Glu Glu Leu Gly Leu Gly Ala
65                  70                  75                  80

His Gly Leu Arg Tyr Ile Asp Cys Asp Pro Trp Ala Phe Ala Pro Pro
                85                  90                  95

Ala Pro Gly Thr Asp Gly Pro Gly Ile Val Phe His Arg Asp Leu Asp
            100                 105                 110

Ala Thr Cys Gln Ser Ile Glu Arg Ala Cys Gly Thr Lys Asp Ala Asp
        115                 120                 125

Ala Tyr Arg Arg Phe Val Ala Val Trp Ser Glu Arg Ser Arg His Val
    130                 135                 140

Met Lys Ala Phe Ser Thr Pro Pro Thr Gly Ser Asn Leu Ile Gly Ala
145                 150                 155                 160

Phe Gly Gly Leu Ala Thr Ala Arg Gly Asn Ser Glu Leu Ser Arg Gln
                165                 170                 175

Phe Leu Ala Pro Gly Asp Ala Leu Leu Asp Glu Tyr Phe Asp Ser Glu
            180                 185                 190

Ala Leu Lys Ala Ala Leu Ala Trp Phe Gly Ala Gln Ser Gly Pro Pro
        195                 200                 205

Met Ser Glu Pro Gly Thr Ala Pro Met Val Gly Phe Ala Ala Leu Met
    210                 215                 220

His Val Leu Pro Pro Gly Arg Ala Val Gly Gly Ser Gly Ala Leu Ser
225                 230                 235                 240

Ala Ala Leu Ala Ser Arg Met Ala Val Asp Gly Ala Thr Val Ala Leu
                245                 250                 255

Gly Asp Gly Val Thr Ser Ile Arg Arg Asn Ser Asn His Trp Thr Val

|     |     |     |     | 260 |     |     |     | 265 |     |     |     | 270 |     |
| --- | --- | --- | --- | --- | --- | --- | --- | --- | --- | --- | --- | --- | --- |
| Thr | Thr | Glu | Ser | Gly | Arg | Glu | Val | His | Ala | Arg | Lys | Val | Ile | Ala | Gly |
|     |     |     | 275 |     |     |     |     | 280 |     |     |     |     | 285 |

Thr Thr Glu Ser Gly Arg Glu Val His Ala Arg Lys Val Ile Ala Gly
            275                 280                 285

Cys His Ile Leu Thr Thr Leu Asp Leu Leu Gly Asn Gly Gly Phe Asp
    290                 295                 300

Arg Thr Thr Leu Asp His Trp Arg Arg Lys Ile Arg Val Gly Pro Gly
305                 310                 315                 320

Ile Gly Ala Val Leu Arg Leu Ala Thr Ser Ala Leu Pro Ser Tyr Arg
                325                 330                 335

Gly Asp Ala Thr Thr Arg Glu Ser Thr Ser Gly Leu Gln Leu Leu Val
            340                 345                 350

Ser Asp Arg Ala His Leu Arg Thr Ala His Gly Ala Ala Leu Ala Gly
        355                 360                 365

Glu Leu Pro Pro Arg Pro Ala Val Leu Gly Met Ser Phe Ser Gly Ile
    370                 375                 380

Asp Pro Thr Ile Ala Pro Ala Gly Arg His Gln Val Thr Leu Trp Ser
385                 390                 395                 400

Gln Trp Gln Pro Tyr Arg Leu Ser Gly His Arg Asp Trp Ala Ser Val
                405                 410                 415

Ala Glu Ala Glu Ala Asp Arg Ile Val Gly Glu Met Glu Ala Phe Ala
            420                 425                 430

Pro Gly Phe Thr Asp Ser Val Leu Asp Arg Phe Ile Gln Thr Pro Arg
        435                 440                 445

Asp Ile Glu Ser Glu Leu Gly Met Ile Gly Gly Asn Val Met His Val
450                 455                 460

Glu Met Ser Leu Asp Gln Met Met Leu Trp Arg Pro Leu Pro Glu Leu
465                 470                 475                 480

Ser Gly His Arg Val Pro Gly Ala Asp Gly Leu Tyr Leu Thr Gly Ala
                485                 490                 495

Ser Thr His Pro Gly Gly Val Ser Gly Ala Ser Gly Arg Ser Ala
            500                 505                 510

Ala Arg Ile Ala Leu Ser Asp Ser Arg Gly Lys Ala Ser Gln Trp
        515                 520                 525

Met Arg Arg Ser Ser Arg Ser
    530                 535

<210> SEQ ID NO 6
<211> LENGTH: 1599
<212> TYPE: DNA
<213> ORGANISM: artificial sequence
<220> FEATURE:
<223> OTHER INFORMATION: crtO320

<400> SEQUENCE: 6

```
atgagcgcat tctcgacgc cgtcgtcgtc ggttccggac acaacgcgct cgtttcggcc      60
gcgtatctcg cacgtgaggg ttggtcggtc gaggttctcg agaaggacac ggttctcggc     120
ggtgccgtct cgaccgtcga gcgatttccc ggatacaagg tggaccgggg gtcgtctgcg     180
cacctcatga tccgacacag tggcatcatc gaggaactcg gactcggcgc gcacggcctt     240
cgctacatcg actgtgaccc gtgggcgttc gctccgcccg ccctggcac cgacgggccg      300 ggcatcgtgt tcatcgcga cctcgatgca acctgccagt ccatcgaacg agcttgcggg     360
acaaaggacg ccgacgcgta ccggcggttc gtcgcggtct ggtcggagcg cagccgacac     420
gtgatgaagg cattttccac accgcccacc ggatcgaacc tgatcggtgc gttcggagga     480
```

```
ctggccacag cgcgcggcaa cagcgaactg tcgcggcagt tcctcgcgcc gggcgacgca       540
ctgctggacg agtatttcga cagtgaggca ctcaaggcag cgttggcgtg gttcggcgcc       600
cagtccgggc ctccgatgtc ggaaccggga accgctccga tggtcggctt cgcggccctc       660
atgcacgtcc tgccgcccgg gcgagcagtc ggagggagcg cgcactgag tgctgcgttg       720 gcatcccgga tggctgtcga cggcgccacc gtcgcgctcg gtgacggcgt gacgtcgatc       780
cgccggaact cgaatcactg gaccgtcaca accgagagcg gtcgagaagt tcacgctcgc       840
aaggtaatcg cgggttgcca catcctcacg acactcgatc tcctgggcaa cggaggcttc       900
gaccgaacca cgctcgatca ctggcggcgg aagatcaggg tcggcccgg catcggcgct        960 gtattgcgac tggcgacatc tgcgctcccg tcctaccgcg gcgacgccac gacacgggaa      1020
agtacctcgg gattgcaatt actcgtttcc gatcgcgccc acttgcgcac tgcacacggc      1080
gcagcactgg caggggaact gcctcctcgc cctgcggttc tcggaatgag tttcagcgga      1140
atcgatccca cgatcgcccc ggccgggcgg catcaggtga cactgtggtc gcagtggcag      1200
ccgtatcgtc tcagcggaca tcgcgattgg gcgtcggtcg ccgaggccga ggccgaccgg      1260
atcgtcggcg agatggaggc ttttgcaccc ggattcaccg attccgtcct cgaccgcttc      1320
attcaaactc cccgcgacat cgagtcggaa ttggggatga tcggcggaaa tgtcatgcac      1380
gtcgagatgt cactcgatca gatgatgttg tggcgaccgc ttcccgaact gtccggccat      1440
cgcgttccgg gagcagacgg gttgtatctg accggagcct cgacgcatcc cggtggtggt      1500
gtgtccggag ccagtggtcg cagtgccgct cgaatcgcac tgtccgacag ccgccggggt      1560
aaagcgagtc agtggatgcg tcgttcgagc cgctcgtga                            1599

<210> SEQ ID NO 7
<211> LENGTH: 27
<212> TYPE: DNA
<213> ORGANISM: artificial sequence
<220> FEATURE:
<223> OTHER INFORMATION: Primer

<400> SEQUENCE: 7
agccaattga aggaggaata aaccatg                                           27

<210> SEQ ID NO 8
<211> LENGTH: 27
<212> TYPE: DNA
<213> ORGANISM: artificial sequence
<220> FEATURE:
<223> OTHER INFORMATION: Primer

<400> SEQUENCE: 8
gcgaattcct ctagattagc tacggct                                           27

<210> SEQ ID NO 9
<211> LENGTH: 30
<212> TYPE: DNA
<213> ORGANISM: artificial sequence
<220> FEATURE:
<223> OTHER INFORMATION: Primer

<400> SEQUENCE: 9
taacaattga aggaggaata aaccatggcc                                        30

<210> SEQ ID NO 10
<211> LENGTH: 30
<212> TYPE: DNA
<213> ORGANISM: artificial sequence
```

```
<220> FEATURE:
<223> OTHER INFORMATION: Primer

<400> SEQUENCE: 10
gcgaattcct ctagatcacg agcggctcga                                      30

<210> SEQ ID NO 11
<211> LENGTH: 19
<212> TYPE: DNA
<213> ORGANISM: artificial sequence
<220> FEATURE:
<223> OTHER INFORMATION: Primer

<400> SEQUENCE: 11
gccattagcc agaccggca                                                  19

<210> SEQ ID NO 12
<211> LENGTH: 18
<212> TYPE: DNA
<213> ORGANISM: artificial sequence
<220> FEATURE:
<223> OTHER INFORMATION: Primer

<400> SEQUENCE: 12
gcgcctggcc agtgaaca                                                   18

<210> SEQ ID NO 13
<211> LENGTH: 1599
<212> TYPE: DNA
<213> ORGANISM: artificial sequence
<220> FEATURE:
<223> OTHER INFORMATION: 319M3022
<220> FEATURE:
<221> NAME/KEY: CDS
<222> LOCATION: (1)..(1599)

<400> SEQUENCE: 13 atg agc acc ttc ctg gac gcg gtc gtg gtc ggc agc ggt cat aac gcc      48
Met Ser Thr Phe Leu Asp Ala Val Val Val Gly Ser Gly His Asn Ala
1               5                   10                  15 ctg gtc agc gcc gcc tat ctg gcc cgc gaa ggc tgg agc gtc gaa gtc      96
Leu Val Ser Ala Ala Tyr Leu Ala Arg Glu Gly Trp Ser Val Glu Val
            20                  25                  30 ctg gaa aag gac acc gtc ctg ggt ggc gcc gtc agc acc gtc gaa cgc     144
Leu Glu Lys Asp Thr Val Leu Gly Gly Ala Val Ser Thr Val Glu Arg
        35                  40                  45 ttc ccg ggc tac aaa gtc gac cgc ggc agc agc gcc cat ctg atg atc     192
Phe Pro Gly Tyr Lys Val Asp Arg Gly Ser Ser Ala His Leu Met Ile
    50                  55                  60 cgc cat agc ggc atc atc gaa gaa ctg ggt ctg ggt gca cat ggc ctg     240
Arg His Ser Gly Ile Ile Glu Glu Leu Gly Leu Gly Ala His Gly Leu
65                  70                  75                  80 cgt tac atc gac tgc gac ccg tgg gcc ttt gct ccg cct gca ccg ggt     288
Arg Tyr Ile Asp Cys Asp Pro Trp Ala Phe Ala Pro Pro Ala Pro Gly
                85                  90                  95 acc gat ggt cct ggt atc gtc ttc cac cgt gac ctg gac gcc acc tgc     336
Thr Asp Gly Pro Gly Ile Val Phe His Arg Asp Leu Asp Ala Thr Cys
            100                 105                 110 caa agc atc gaa cgc gcc tgc ggt acc aaa gac gcc gat gcc tat cgt     384
Gln Ser Ile Glu Arg Ala Cys Gly Thr Lys Asp Ala Asp Ala Tyr Arg
        115                 120                 125 cgc ttc gtc gcc gtc tgg tcg gaa cgc agc cgc cat gtc atg aaa gcc     432
Arg Phe Val Ala Val Trp Ser Glu Arg Ser Arg His Val Met Lys Ala
    130                 135                 140
```

-continued

```
ttc agc acc cct ccg acc ggt agc aac ctg atc ggt gcg ttt ggt ggc    480
Phe Ser Thr Pro Pro Thr Gly Ser Asn Leu Ile Gly Ala Phe Gly Gly
145                 150                 155                 160 ctg gcg acc gca cgt ggt aac agc gaa ctg tcc cgt caa ttc ctg gct    528
Leu Ala Thr Ala Arg Gly Asn Ser Glu Leu Ser Arg Gln Phe Leu Ala
                165                 170                 175 ccg ggt gac gcc ttg ctg gac gaa tac ttc gac tcc gaa gcc ctg aaa    576
Pro Gly Asp Ala Leu Leu Asp Glu Tyr Phe Asp Ser Glu Ala Leu Lys
            180                 185                 190 gcc gct ctg gcc tgg ttt ggt gct caa tcc ggt cct ccg atg tcc gaa    624
Ala Ala Leu Ala Trp Phe Gly Ala Gln Ser Gly Pro Pro Met Ser Glu
        195                 200                 205 cct ggc acc gct cct atg gtc ggc ttc gcc gct ttg atg cat gtc ttg    672
Pro Gly Thr Ala Pro Met Val Gly Phe Ala Ala Leu Met His Val Leu
    210                 215                 220 ccg cca ggt cgt gct gtg ggt ggc tcc ggt gcg ctg tcg gca gcc ctg    720
Pro Pro Gly Arg Ala Val Gly Gly Ser Gly Ala Leu Ser Ala Ala Leu
225                 230                 235                 240 gcg tcc cgc atg gcc gtc gat ggt gcg acc gtc gcc ctg ggt gat ggt    768
Ala Ser Arg Met Ala Val Asp Gly Ala Thr Val Ala Leu Gly Asp Gly
                245                 250                 255 gtc acc agc atc cgt cgc gac agc aac cat tgg acc gtc acc acc gaa    816
Val Thr Ser Ile Arg Arg Asp Ser Asn His Trp Thr Val Thr Thr Glu
            260                 265                 270 agc ggc cgt gaa gtc cat gcc cgc aaa gtc atc gcc ggc tgc cat atc    864
Ser Gly Arg Glu Val His Ala Arg Lys Val Ile Ala Gly Cys His Ile
        275                 280                 285 ctg acc acc ttg gac ttg ctg ggc aac ggt ggc ttc gat cgc acc act    912
Leu Thr Thr Leu Asp Leu Leu Gly Asn Gly Gly Phe Asp Arg Thr Thr
    290                 295                 300 ctg gac cat tgg cgt cgt aag atc cgt gtc ggt cca ggc atc ggt gcc    960
Leu Asp His Trp Arg Arg Lys Ile Arg Val Gly Pro Gly Ile Gly Ala
305                 310                 315                 320 gtc ctg cgt ctg gcc acc agc gcc ttg ccg agc tat cgt ggt gat gcc    1008
Val Leu Arg Leu Ala Thr Ser Ala Leu Pro Ser Tyr Arg Gly Asp Ala
                325                 330                 335 acc acc cgc gaa agc acc tcc ggt ctg caa ctg ctg gtc agc gac cgt    1056
Thr Thr Arg Glu Ser Thr Ser Gly Leu Gln Leu Leu Val Ser Asp Arg
            340                 345                 350 gcc cat ctg cgt acc gcg cat ggc gct gcc ttg gct ggt gaa ctg cca    1104
Ala His Leu Arg Thr Ala His Gly Ala Ala Leu Ala Gly Glu Leu Pro
        355                 360                 365 ccg cgt cct gct gtc ctg ggc atg agc ttc agc ggc atc gat ccg acg    1152
Pro Arg Pro Ala Val Leu Gly Met Ser Phe Ser Gly Ile Asp Pro Thr
    370                 375                 380 att gct ccg gcc ggt cgt cat caa gtc acc ctg tgg agc caa tgg caa    1200
Ile Ala Pro Ala Gly Arg His Gln Val Thr Leu Trp Ser Gln Trp Gln
385                 390                 395                 400 ccg tat cgc ctg agc ggt cat cgt gac tgg gcc agc gtc gct gaa gcc    1248
Pro Tyr Arg Leu Ser Gly His Arg Asp Trp Ala Ser Val Ala Glu Ala
                405                 410                 415 gaa gcc gac cgt atc gtg ggt gaa atg gaa gct ttc gct ccg ggt ttc    1296
Glu Ala Asp Arg Ile Val Gly Glu Met Glu Ala Phe Ala Pro Gly Phe
            420                 425                 430 acc gac tcc gtc ctg gac cgc ttc atc caa acg ccg cgt gat atc gaa    1344
Thr Asp Ser Val Leu Asp Arg Phe Ile Gln Thr Pro Arg Asp Ile Glu
        435                 440                 445 agc gaa ctg ggt atg atc ggc ggt aac gtc atg cat gtc gag atg agc    1392
Ser Glu Leu Gly Met Ile Gly Gly Asn Val Met His Val Glu Met Ser
```

```
                450                 455                 460
ctg gac caa atg atg ctg tgg cgt ccg ttg ccg gaa ctg tcg ggc cac      1440
Leu Asp Gln Met Met Leu Trp Arg Pro Leu Pro Glu Leu Ser Gly His
465                 470                 475                 480 cgc gtg ccg ggt gcc gat ggc ctg tat ctg acg ggt gcc agc acc cat      1488
Arg Val Pro Gly Ala Asp Gly Leu Tyr Leu Thr Gly Ala Ser Thr His
                485                 490                 495 ccg ggt ggt ggc gtc tcg ggt gcc tcc ggt cgc agc gcc gcc cgc att      1536
Pro Gly Gly Gly Val Ser Gly Ala Ser Gly Arg Ser Ala Ala Arg Ile
            500                 505                 510 gcc ctg agc gac agc cgc cgc ggt aaa gcc agc caa tgg ttg cgt cgc      1584
Ala Leu Ser Asp Ser Arg Arg Gly Lys Ala Ser Gln Trp Leu Arg Arg
        515                 520                 525 agc agc cgt agc taa                                                  1599
Ser Ser Arg Ser
    530
```

<210> SEQ ID NO 14
<211> LENGTH: 532
<212> TYPE: PRT
<213> ORGANISM: artificial sequence
<220> FEATURE:
<223> OTHER INFORMATION: Synthetic Construct

<400> SEQUENCE: 14

```
Met Ser Thr Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg
        35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
    130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255
```

```
Val Thr Ser Ile Arg Arg Asp Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Leu Ala Gly Glu Leu Pro
        355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
        435                 440                 445

Ser Glu Leu Gly Met Ile Gly Gly Asn Val Met His Val Glu Met Ser
    450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Leu Arg Arg
        515                 520                 525

Ser Ser Arg Ser
    530

<210> SEQ ID NO 15
<211> LENGTH: 1608
<212> TYPE: DNA
<213> ORGANISM: artificial sequence
<220> FEATURE:
<223> OTHER INFORMATION: 303M3044
<220> FEATURE:
<221> NAME/KEY: CDS
<222> LOCATION: (1)..(1608)

<400> SEQUENCE: 15 atg gcc ctt atg cgc gca ttt ctc gac gcc gtc gtc gtc ggt tcc gga      48
Met Ala Leu Met Arg Ala Phe Leu Asp Ala Val Val Val Gly Ser Gly
1               5                   10                  15 cac aac gcg ctc gtt tcg gcc gcg tat ctc gca cgt gag ggt tgg tcg      96
His Asn Ala Leu Val Ser Ala Ala Tyr Leu Ala Arg Glu Gly Trp Ser
            20                  25                  30 gtc gag gtt ctc gag aag gac acg gtt ctc ggc ggt gcc gtc tcg acc     144
Val Glu Val Leu Glu Lys Asp Thr Val Leu Gly Gly Ala Val Ser Thr
        35                  40                  45
```

-continued

| | |
|---|---|
| gtc gag cga ttt ccc gga tac aag gtg gac cgg ggg tcg tct gcg cac<br>Val Glu Arg Phe Pro Gly Tyr Lys Val Asp Arg Gly Ser Ser Ala His<br>50                            55                         60 | 192 |
| ctc atg atc cga cac agt ggc atc atc gag gaa ctg gga ctc ggc gcg<br>Leu Met Ile Arg His Ser Gly Ile Ile Glu Glu Leu Gly Leu Gly Ala<br>65                            70                         75                         80 | 240 |
| cac ggc ctt cgc tac atc gac tgt gac ccg tgg gcg ttc gct ccg ccc<br>His Gly Leu Arg Tyr Ile Asp Cys Asp Pro Trp Ala Phe Ala Pro Pro<br>                         85                         90                         95 | 288 |
| gcc cct ggc acc gac ggg ccg ggc atc gtg ttt cat cgc gac ctc gat<br>Ala Pro Gly Thr Asp Gly Pro Gly Ile Val Phe His Arg Asp Leu Asp<br>                 100                     105                     110 | 336 |
| gca acc tgc cag tcc atc gaa cga gct tgc ggg aca aag gac gcc gac<br>Ala Thr Cys Gln Ser Ile Glu Arg Ala Cys Gly Thr Lys Asp Ala Asp<br>                 115                     120                     125 | 384 |
| gcg tac cgg cgg ttc gtc gcg gtc tgg tcg gag cgc agc cga cac gtg<br>Ala Tyr Arg Arg Phe Val Ala Val Trp Ser Glu Arg Ser Arg His Val<br>130                           135                     140 | 432 |
| atg aag gca ttt tcc aca ccg ccc acc gga tcg aac ctg atc ggt gcg<br>Met Lys Ala Phe Ser Thr Pro Pro Thr Gly Ser Asn Leu Ile Gly Ala<br>145                         150                     155                 160 | 480 |
| ttc gga gga ctg gcc aca gcg cgc ggc aac agc gaa ctg tcg cgg cag<br>Phe Gly Gly Leu Ala Thr Ala Arg Gly Asn Ser Glu Leu Ser Arg Gln<br>                 165                     170                     175 | 528 |
| ttc ctc gcg ccg ggc gac gca ctg ctg gac gag tat ttc gac agt gag<br>Phe Leu Ala Pro Gly Asp Ala Leu Leu Asp Glu Tyr Phe Asp Ser Glu<br>                 180                     185                     190 | 576 |
| gca ctc aag gca gcg ttg gcg tgg ttc ggc gcc cag tcc ggg cct ccg<br>Ala Leu Lys Ala Ala Leu Ala Trp Phe Gly Ala Gln Ser Gly Pro Pro<br>                 195                     200                     205 | 624 |
| atg tcg gaa ccg gga acc gct ccg atg gtc ggc ttc gcg gcc ctc atg<br>Met Ser Glu Pro Gly Thr Ala Pro Met Val Gly Phe Ala Ala Leu Met<br>210                           215                     220 | 672 |
| cac gtc ctg ccg ccc ggg cga gca gtc gga ggg agc ggc gca ctg agt<br>His Val Leu Pro Pro Gly Arg Ala Val Gly Gly Ser Gly Ala Leu Ser<br>225                           230                     235                 240 | 720 |
| gct gcg ttg gca tcc cgg atg gct gtc gac ggc gcc acc gtc gcg ctc<br>Ala Ala Leu Ala Ser Arg Met Ala Val Asp Gly Ala Thr Val Ala Leu<br>                 245                     250                     255 | 768 |
| ggt gac ggc gtg acg tcg atc cgc cgg aac tcg aat cac tgg acc gtc<br>Gly Asp Gly Val Thr Ser Ile Arg Arg Asn Ser Asn His Trp Thr Val<br>                 260                     265                     270 | 816 |
| aca acc gag agc ggt cga gaa gtt cac gct cgc aag gta atc gcg ggt<br>Thr Thr Glu Ser Gly Arg Glu Val His Ala Arg Lys Val Ile Ala Gly<br>                 275                     280                     285 | 864 |
| tgc cac atc ctc acg aca ctc gat ctc ctg ggc aac gga ggc ttc gac<br>Cys His Ile Leu Thr Thr Leu Asp Leu Leu Gly Asn Gly Gly Phe Asp<br>290                           295                     300 | 912 |
| cga acc acg ctc gat cac tgg cgg cgg aag atc agg gtc ggc ccc ggc<br>Arg Thr Thr Leu Asp His Trp Arg Arg Lys Ile Arg Val Gly Pro Gly<br>305                           310                     315                 320 | 960 |
| atc ggc gct gta ttg cga ctg gcg aca tct gcg ctc ccg tcc tac cgc<br>Ile Gly Ala Val Leu Arg Leu Ala Thr Ser Ala Leu Pro Ser Tyr Arg<br>                 325                     330                     335 | 1008 |
| ggc gac gcc acg aca cgg gaa agt acc tcg gga ttg caa tta ctc gtt<br>Gly Asp Ala Thr Thr Arg Glu Ser Thr Ser Gly Leu Gln Leu Leu Val<br>                 340                     345                     350 | 1056 |
| tcc gat cgc gcc cac ttg cgc act gca cac ggc gca gca ctg gca ggg<br>Ser Asp Arg Ala His Leu Arg Thr Ala His Gly Ala Ala Leu Ala Gly | 1104 |

```
                          355                 360                 365
gaa ctg cct cct cgc cct gcg gtt ctc gga atg agt ttc agc gga atc        1152
Glu Leu Pro Pro Arg Pro Ala Val Leu Gly Met Ser Phe Ser Gly Ile
    370                 375                 380 gat ccc acg atc gcc ccg gcc ggg cgg cat cag gtg aca ctg tgg tcg        1200
Asp Pro Thr Ile Ala Pro Ala Gly Arg His Gln Val Thr Leu Trp Ser
385                 390                 395                 400 cag tgg cag ccg tat cgt ctc agc gga cat cgc gat tgg gcg tcg gtc        1248
Gln Trp Gln Pro Tyr Arg Leu Ser Gly His Arg Asp Trp Ala Ser Val
            405                 410                 415 gcc gag gcc gag gcc gac cgg atc gtc ggc gag atg gag gct ttt gca        1296
Ala Glu Ala Glu Ala Asp Arg Ile Val Gly Glu Met Glu Ala Phe Ala
                420                 425                 430 ccc gga ttc acc gat tcc gtc ctc gac cgc ttc att caa act ccc cgc        1344
Pro Gly Phe Thr Asp Ser Val Leu Asp Arg Phe Ile Gln Thr Pro Arg
                    435                 440                 445 gac atc gag tcg gaa ttg ggg atg atc ggc gga aat gtc atg cac gtc        1392
Asp Ile Glu Ser Glu Leu Gly Met Ile Gly Gly Asn Val Met His Val
    450                 455                 460 gag atg tca ctc gat cag atg atg ttg tgg cga ccg ctt ccc gaa ctg        1440
Glu Met Ser Leu Asp Gln Met Met Leu Trp Arg Pro Leu Pro Glu Leu
465                 470                 475                 480 tcc ggc cat cgc gtt ccg gga gca gac ggg ttg tat ctg acc gga gcc        1488
Ser Gly His Arg Val Pro Gly Ala Asp Gly Leu Tyr Leu Thr Gly Ala
            485                 490                 495 tcg aca cat ccc ggt ggt ggt gtg tcc gga gcc agt ggt cgc agt gcc        1536
Ser Thr His Pro Gly Gly Gly Val Ser Gly Ala Ser Gly Arg Ser Ala
                500                 505                 510 gct cga atc gca ctg tcc gac agc cgc cgg ggt aaa gcg agt cag tgg        1584
Ala Arg Ile Ala Leu Ser Asp Ser Arg Arg Gly Lys Ala Ser Gln Trp
                    515                 520                 525 atg cgt cgt tcg agc cgc tcg tga                                        1608
Met Arg Arg Ser Ser Arg Ser
    530                 535

<210> SEQ ID NO 16
<211> LENGTH: 535
<212> TYPE: PRT
<213> ORGANISM: artificial sequence
<220> FEATURE:
<223> OTHER INFORMATION: Synthetic Construct

<400> SEQUENCE: 16

Met Ala Leu Met Arg Ala Phe Leu Asp Ala Val Val Gly Ser Gly
1               5                   10                  15

His Asn Ala Leu Val Ser Ala Ala Tyr Leu Ala Arg Glu Gly Trp Ser
            20                  25                  30

Val Glu Val Leu Glu Lys Asp Thr Val Leu Gly Gly Ala Val Ser Thr
        35                  40                  45

Val Glu Arg Phe Pro Gly Tyr Lys Val Asp Arg Gly Ser Ser Ala His
    50                  55                  60

Leu Met Ile Arg His Ser Gly Ile Ile Glu Glu Leu Gly Leu Gly Ala
65                  70                  75                  80

His Gly Leu Arg Tyr Ile Asp Cys Asp Pro Trp Ala Phe Ala Pro Pro
                85                  90                  95

Ala Pro Gly Thr Asp Gly Pro Gly Ile Val Phe His Arg Asp Leu Asp
            100                 105                 110

Ala Thr Cys Gln Ser Ile Glu Arg Ala Cys Gly Thr Lys Asp Ala Asp
        115                 120                 125
```

```
Ala Tyr Arg Arg Phe Val Ala Val Trp Ser Glu Arg Ser His Val
    130                 135                 140
Met Lys Ala Phe Ser Thr Pro Pro Thr Gly Ser Asn Leu Ile Gly Ala
145                 150                 155                 160
Phe Gly Gly Leu Ala Thr Ala Arg Gly Asn Ser Glu Leu Ser Arg Gln
                165                 170                 175
Phe Leu Ala Pro Gly Asp Ala Leu Leu Asp Glu Tyr Phe Asp Ser Glu
            180                 185                 190
Ala Leu Lys Ala Ala Leu Ala Trp Phe Gly Ala Gln Ser Gly Pro Pro
        195                 200                 205
Met Ser Glu Pro Gly Thr Ala Pro Met Val Gly Phe Ala Ala Leu Met
    210                 215                 220
His Val Leu Pro Pro Gly Arg Ala Val Gly Ser Gly Ala Leu Ser
225                 230                 235                 240
Ala Ala Leu Ala Ser Arg Met Ala Val Asp Gly Ala Thr Val Ala Leu
                245                 250                 255
Gly Asp Gly Val Thr Ser Ile Arg Arg Asn Ser Asn His Trp Thr Val
            260                 265                 270
Thr Thr Glu Ser Gly Arg Glu Val His Ala Arg Lys Val Ile Ala Gly
        275                 280                 285
Cys His Ile Leu Thr Thr Leu Asp Leu Leu Gly Asn Gly Gly Phe Asp
    290                 295                 300
Arg Thr Thr Leu Asp His Trp Arg Arg Lys Ile Arg Val Gly Pro Gly
305                 310                 315                 320
Ile Gly Ala Val Leu Arg Leu Ala Thr Ser Ala Leu Pro Ser Tyr Arg
                325                 330                 335
Gly Asp Ala Thr Thr Arg Glu Ser Thr Ser Gly Leu Gln Leu Leu Val
            340                 345                 350
Ser Asp Arg Ala His Leu Arg Thr Ala His Gly Ala Ala Leu Ala Gly
        355                 360                 365
Glu Leu Pro Pro Arg Pro Ala Val Leu Gly Met Ser Phe Ser Gly Ile
    370                 375                 380
Asp Pro Thr Ile Ala Pro Ala Gly Arg His Gln Val Thr Leu Trp Ser
385                 390                 395                 400
Gln Trp Gln Pro Tyr Arg Leu Ser Gly His Arg Asp Trp Ala Ser Val
                405                 410                 415
Ala Glu Ala Glu Ala Asp Arg Ile Val Gly Glu Met Glu Ala Phe Ala
            420                 425                 430
Pro Gly Phe Thr Asp Ser Val Leu Asp Arg Phe Ile Gln Thr Pro Arg
        435                 440                 445
Asp Ile Glu Ser Glu Leu Gly Met Ile Gly Gly Asn Val Met His Val
    450                 455                 460
Glu Met Ser Leu Asp Gln Met Met Leu Trp Arg Pro Leu Pro Glu Leu
465                 470                 475                 480
Ser Gly His Arg Val Pro Gly Ala Asp Gly Leu Tyr Leu Thr Gly Ala
                485                 490                 495
Ser Thr His Pro Gly Gly Val Ser Gly Ala Ser Gly Arg Ser Ala
            500                 505                 510
Ala Arg Ile Ala Leu Ser Asp Ser Arg Gly Lys Ala Ser Gln Trp
        515                 520                 525
Met Arg Arg Ser Ser Arg Ser
    530                 535
```

<210> SEQ ID NO 17
<211> LENGTH: 1599
<212> TYPE: DNA
<213> ORGANISM: artificial sequence
<220> FEATURE:
<223> OTHER INFORMATION: 320M4006
<220> FEATURE:
<221> NAME/KEY: CDS
<222> LOCATION: (1)..(1599)

<400> SEQUENCE: 17

| | | | | | | | | | | | | | | | | |
|---|---|---|---|---|---|---|---|---|---|---|---|---|---|---|---|---|
| atg | agc | gca | ttt | ctc | gac | gcc | gtc | gtc | gtc | ggt | tcc | gga | cac | aac | gca | 48 |
| Met | Ser | Ala | Phe | Leu | Asp | Ala | Val | Val | Val | Gly | Ser | Gly | His | Asn | Ala | |
| 1 | | | | 5 | | | | | 10 | | | | | 15 | | |
| ctc | gtt | tcg | gcc | gcg | tat | ctc | gca | cgt | gag | ggt | tgg | tcg | gtc | gag | gtt | 96 |
| Leu | Val | Ser | Ala | Ala | Tyr | Leu | Ala | Arg | Glu | Gly | Trp | Ser | Val | Glu | Val | |
| | | | 20 | | | | | 25 | | | | | 30 | | | |
| ctc | gag | aag | gac | acg | gtt | ctc | ggc | ggt | gcc | gtc | tcg | acc | gtc | gag | cga | 144 |
| Leu | Glu | Lys | Asp | Thr | Val | Leu | Gly | Gly | Ala | Val | Ser | Thr | Val | Glu | Arg | |
| | 35 | | | | | 40 | | | | | 45 | | | | | |
| ttt | ccc | gga | tac | aag | gtg | gac | cgg | ggg | tcg | tct | gcg | cac | ctc | atg | atc | 192 |
| Phe | Pro | Gly | Tyr | Lys | Val | Asp | Arg | Gly | Ser | Ser | Ala | His | Leu | Met | Ile | |
| 50 | | | | | 55 | | | | | 60 | | | | | | |
| cga | cac | agt | ggc | atc | atc | gag | gaa | ctc | gga | ctc | ggc | gcg | cac | ggc | ctt | 240 |
| Arg | His | Ser | Gly | Ile | Ile | Glu | Glu | Leu | Gly | Leu | Gly | Ala | His | Gly | Leu | |
| 65 | | | | | 70 | | | | | 75 | | | | | 80 | |
| cgc | tac | atc | gac | tgt | gac | ccg | tgg | gcg | ttc | gct | ccg | ccc | gcc | cct | ggc | 288 |
| Arg | Tyr | Ile | Asp | Cys | Asp | Pro | Trp | Ala | Phe | Ala | Pro | Pro | Ala | Pro | Gly | |
| | | | | 85 | | | | | 90 | | | | | 95 | | |
| acc | gac | ggg | ccg | ggc | atc | gtg | ttt | cat | cgc | gac | ctc | gat | gca | acc | tgc | 336 |
| Thr | Asp | Gly | Pro | Gly | Ile | Val | Phe | His | Arg | Asp | Leu | Asp | Ala | Thr | Cys | |
| | | | 100 | | | | | 105 | | | | | 110 | | | |
| cag | tcc | atc | gaa | cga | gct | tgc | ggg | aca | aag | gac | gcc | gac | gcg | tac | cgg | 384 |
| Gln | Ser | Ile | Glu | Arg | Ala | Cys | Gly | Thr | Lys | Asp | Ala | Asp | Ala | Tyr | Arg | |
| | 115 | | | | | 120 | | | | | 125 | | | | | |
| cgg | ttc | gtc | gcg | gtc | tgg | tcg | gag | cgc | agc | cga | cac | gtg | atg | aag | gca | 432 |
| Arg | Phe | Val | Ala | Val | Trp | Ser | Glu | Arg | Ser | Arg | His | Val | Met | Lys | Ala | |
| 130 | | | | | 135 | | | | | 140 | | | | | | |
| ttt | tcc | aca | ccg | ccc | acc | gga | tcg | aac | ctg | atc | ggt | gcg | ttc | gga | gga | 480 |
| Phe | Ser | Thr | Pro | Pro | Thr | Gly | Ser | Asn | Leu | Ile | Gly | Ala | Phe | Gly | Gly | |
| 145 | | | | | 150 | | | | | 155 | | | | | 160 | |
| ctg | gcc | aca | gcg | cgc | ggc | aac | agc | gaa | ctg | tcg | cgg | cag | ttc | ctc | gcg | 528 |
| Leu | Ala | Thr | Ala | Arg | Gly | Asn | Ser | Glu | Leu | Ser | Arg | Gln | Phe | Leu | Ala | |
| | | | | 165 | | | | | 170 | | | | | 175 | | |
| ccg | ggc | gac | gca | ctg | ctg | gac | gag | tat | ttc | gac | agt | gag | gca | ctc | aag | 576 |
| Pro | Gly | Asp | Ala | Leu | Leu | Asp | Glu | Tyr | Phe | Asp | Ser | Glu | Ala | Leu | Lys | |
| | | | 180 | | | | | 185 | | | | | 190 | | | |
| gca | gcg | ttg | gcg | tgg | ttc | ggc | gcc | cag | tcc | ggg | cct | ccg | atg | tcg | gaa | 624 |
| Ala | Ala | Leu | Ala | Trp | Phe | Gly | Ala | Gln | Ser | Gly | Pro | Pro | Met | Ser | Glu | |
| | 195 | | | | | 200 | | | | | 205 | | | | | |
| ccg | gga | acc | gct | ccg | atg | gtc | ggc | ttc | gcg | gcc | ctc | atg | cac | gtc | ctg | 672 |
| Pro | Gly | Thr | Ala | Pro | Met | Val | Gly | Phe | Ala | Ala | Leu | Met | His | Val | Leu | |
| 210 | | | | | 215 | | | | | 220 | | | | | | |
| ccg | ccc | ggg | cga | gca | gtc | gga | ggg | agc | ggc | gca | ctg | agt | gct | gcg | ttg | 720 |
| Pro | Pro | Gly | Arg | Ala | Val | Gly | Gly | Ser | Gly | Ala | Leu | Ser | Ala | Ala | Leu | |
| 225 | | | | | 230 | | | | | 235 | | | | | 240 | |
| gca | tcc | cgg | atg | gct | gtc | gac | ggc | gcc | acc | gtc | gcg | ctc | ggt | gac | ggc | 768 |
| Ala | Ser | Arg | Met | Ala | Val | Asp | Gly | Ala | Thr | Val | Ala | Leu | Gly | Asp | Gly | |
| | | | | 245 | | | | | 250 | | | | | 255 | | |
| gtg | acg | tcg | atc | cgc | cgg | aac | tcg | aat | cac | tgg | acc | gtc | aca | acc | gag | 816 |
| Val | Thr | Ser | Ile | Arg | Arg | Asn | Ser | Asn | His | Trp | Thr | Val | Thr | Thr | Glu | |

```
                   260                 265                 270
agc ggt cga gaa gtt cac gct cgc aag gta atc gcg ggt tgc cac atc       864
Ser Gly Arg Glu Val His Ala Arg Lys Val Ile Ala Gly Cys His Ile
            275                 280                 285 ctc acg aca ctc gat ctc ctg ggc aac gga ggc ttc gac cga acc acg       912
Leu Thr Thr Leu Asp Leu Leu Gly Asn Gly Gly Phe Asp Arg Thr Thr
        290                 295                 300 ctc gat cac tgg cgg cgg aag atc agg gtc ggc ccc ggc atc ggc gct       960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc      1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc      1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct      1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg      1152
Pro Arg Pro Ala Val Leu Gly Met Ser Phe Ser Gly Ile Asp Pro Thr
370                 375                 380 atc gcc ccg gcc ggg cgg cat cag gtc aca ctg tgg tcg cag tgg cag      1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc      1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc      1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag      1344
Thr Asp Ser Val Leu Asp Arg Phe Ile Gln Thr Pro Arg Asp Ile Glu
        435                 440                 445 acg gaa ttg ggg atg atc ggc gga aat gtc atg cac gtc gag atg tca      1392
Thr Glu Leu Gly Met Ile Gly Gly Asn Val Met His Val Glu Met Ser
450                 455                 460 ctc gat cag atg atg ttg tgg cga ccg ctt ccc gaa ctg tcc ggc cat      1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat      1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc      1536
Pro Gly Gly Gly Val Ser Gly Ala Ser Gly Arg Ser Ala Ala Arg Ile
            500                 505                 510 gca ctg tcc gac agc cgc cgg ggt aaa gcg agt cag tgg atg cgt cgt      1584
Ala Leu Ser Asp Ser Arg Arg Gly Lys Ala Ser Gln Trp Met Arg Arg
        515                 520                 525 tcg agc cgc tcg tga                                                   1599
Ser Ser Arg Ser
        530
```

<210> SEQ ID NO 18
<211> LENGTH: 532
<212> TYPE: PRT
<213> ORGANISM: artificial sequence
<220> FEATURE:
<223> OTHER INFORMATION: Synthetic Construct

<400> SEQUENCE: 18

-continued

```
Met Ser Ala Phe Leu Asp Ala Val Val Gly Ser Gly His Asn Ala
1               5                  10                 15

Leu Val Ser Ala Ala Tyr Leu Ala Arg Glu Gly Trp Ser Val Glu Val
            20                  25                  30

Leu Glu Lys Asp Thr Val Leu Gly Ala Val Ser Thr Val Glu Arg
        35                  40                  45

Phe Pro Gly Tyr Lys Val Asp Arg Gly Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
            115                 120                 125

Arg Phe Val Ala Val Trp Ser Glu Arg Ser Arg His Val Met Lys Ala
    130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
            245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
            325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
            405                 410                 415
```

```
Glu Ala Asp Arg Ile Val Gly Glu Met Glu Ala Phe Ala Pro Gly Phe
                420                 425                 430

Thr Asp Ser Val Leu Asp Arg Phe Ile Gln Thr Pro Arg Asp Ile Glu
            435                 440                 445

Thr Glu Leu Gly Met Ile Gly Gly Asn Val Met His Val Glu Met Ser
        450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Met Arg Arg
        515                 520                 525

Ser Ser Arg Ser
    530
```

<210> SEQ ID NO 19
<211> LENGTH: 1599
<212> TYPE: DNA
<213> ORGANISM: artificial sequence
<220> FEATURE:
<223> OTHER INFORMATION: 320M4007
<220> FEATURE:
<221> NAME/KEY: CDS
<222> LOCATION: (1)..(1599)

<400> SEQUENCE: 19

```
atg agc gca ttt ctc gac gcc gtc gtc gtc ggt tcc gga cac aac gcg      48
Met Ser Ala Phe Leu Asp Ala Val Val Val Gly Ser Gly His Asn Ala
1               5                   10                  15 ctt gtt tcg gcc gcg tat ctc gct cgt gag ggt tgg tcg gtc gag gtt      96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc     288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tac     336
Thr Asp Gly Pro Gly Ile Val Phe His Arg Asp Leu Asp Ala Thr Tyr
                100                 105                 110 cag tcc atc gaa cga gct tgc ggg aca aag gac gcc gac gcg tac cgg     384
Gln Ser Ile Glu Arg Ala Cys Gly Thr Lys Asp Ala Asp Ala Tyr Arg
            115                 120                 125 cgg ttc gtc gcg gtc tgg tcg gag cgc agc cga cac gtg atg aag gca     432
Arg Phe Val Ala Val Trp Ser Glu Arg Ser Arg His Val Met Lys Ala
        130                 135                 140 ttt tcc aca ccg ccc acc gga tcg aac ctg atc ggt gcg ttc gga gga     480
Phe Ser Thr Pro Pro Thr Gly Ser Asn Leu Ile Gly Ala Phe Gly Gly
145                 150                 155                 160 ctg gcc aca gcg cgc ggc aac agc gaa ctg tcg cgg cag ttc ctc gcg     528
Leu Ala Thr Ala Arg Gly Asn Ser Glu Leu Ser Arg Gln Phe Leu Ala
```

-continued

```
                  165                 170                 175
ccg ggc gac gca ctg ctg gac gag tat ttc gac agt gag gca ctc aag    576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa    624
Ala Ala Leu Ala Trp Phe Gly Ala Gln Ser Gly Pro Pro Met Ser Glu
        195                 200                 205 ccg gga acc gct ccg atg gtc ggc ttc gcg gcc ctc atg cac gtc ctg    672
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg    720
Pro Pro Gly Arg Ala Val Gly Gly Ser Gly Ala Leu Ser Ala Ala Leu
225                 230                 235                 240 gca tcc cgg atg gct gtc gac ggc gcc acc gtc acg ctc ggt gac ggc    768
Ala Ser Arg Met Ala Val Asp Gly Ala Thr Val Thr Leu Gly Asp Gly
                245                 250                 255 gtg acg tcg atc cgc cgg aac tcg aat cac tgg acc gtc aca acc gag    816
Val Thr Ser Ile Arg Arg Asn Ser Asn His Trp Thr Val Thr Thr Glu
            260                 265                 270 agc ggt cga gaa gtt cac gct cgc aag gta atc gcg ggt tgc cac atc    864
Ser Gly Arg Glu Val His Ala Arg Lys Val Ile Ala Gly Cys His Ile
        275                 280                 285 ctc acg aca ctc gat ctc ctg ggc aac gga ggc ttc gac cga acc acg    912
Leu Thr Thr Leu Asp Leu Leu Gly Asn Gly Gly Phe Asp Arg Thr Thr
    290                 295                 300 ctc gat cac tgg cgg cgg aag atc agg gtc ggc ccc ggc atc ggc gct    960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc    1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc    1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct    1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg    1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag    1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc    1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc    1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag    1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca    1392
Ser Glu Leu Gly Met Ile Gly Gly Asn Val Met His Val Glu Met Ser
    450                 455                 460 ctc gat cag atg atg ttg tgg cga ccg ctt ccc gaa ctg tcc ggc cat    1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat    1488
```

```
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc     1536
Pro Gly Gly Gly Val Ser Gly Ala Ser Gly Arg Ser Ala Ala Arg Ile
                500                 505                 510 gca ctg tcc gac agc cgc cgg ggt aaa gcg agt cgg tgg atg cgt cgt     1584
Ala Leu Ser Asp Ser Arg Arg Gly Lys Ala Ser Arg Trp Met Arg Arg
                515                 520                 525 tcg agc cgc tcg tga                                                 1599
Ser Ser Arg Ser
        530

<210> SEQ ID NO 20
<211> LENGTH: 532
<212> TYPE: PRT
<213> ORGANISM: artificial sequence
<220> FEATURE:
<223> OTHER INFORMATION: Synthetic Construct

<400> SEQUENCE: 20

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
        50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Tyr
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Thr Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285
```

```
Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
        435                 440                 445

Ser Glu Leu Gly Met Ile Gly Gly Asn Val Met His Val Glu Met Ser
450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Arg Trp Met Arg Arg
        515                 520                 525

Ser Ser Arg Ser
530
```

<210> SEQ ID NO 21
<211> LENGTH: 1599
<212> TYPE: DNA
<213> ORGANISM: artificial sequence
<220> FEATURE:
<223> OTHER INFORMATION: 320M4009
<220> FEATURE:
<221> NAME/KEY: CDS
<222> LOCATION: (1)..(1599)

<400> SEQUENCE: 21

```
atg aga gca ttt ctc gac gcc gtc gtc gtc ggt tcc gga cac aac gcg      48
Met Arg Ala Phe Leu Asp Ala Val Val Val Gly Ser Gly His Asn Ala
1               5                   10                  15 ctc gtt tcg gcc gcg tat ctc gca cgt gag ggt tgg tcg gtc gag gtt      96
Leu Val Ser Ala Ala Tyr Leu Ala Arg Glu Gly Trp Ser Val Glu Val
                20                  25                  30 ctc gag aag gac atg gtt ctc ggc ggt gcc gtc tcg acc gtc gag cga     144
Leu Glu Lys Asp Met Val Leu Gly Gly Ala Val Ser Thr Val Glu Arg
            35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
```

-continued

```
                65                  70                  75                  80
cgc tac atc gac tgt gac ccg tgg gcg ttc gct ccg ccc gcc cct ggc          288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc          336
Thr Asp Gly Pro Gly Ile Val Phe His Arg Asp Leu Asp Ala Thr Cys
            100                 105                 110 cag tcc atc gaa cgt gct tgc ggg aca aag gac gcc gac gcg tac cgg          384
Gln Ser Ile Glu Arg Ala Cys Gly Thr Lys Asp Ala Asp Ala Tyr Arg
            115                 120                 125 cgg ttc gtc gcg gtc tgg tcg gag cgc agc cga cac gtg atg aag gca          432
Arg Phe Val Ala Val Trp Ser Glu Arg Ser Arg His Val Met Lys Ala
        130                 135                 140 ttt tcc aca ccg ccc acc gga tcg aac ctg atc ggt gcg ttc gga gga          480
Phe Ser Thr Pro Pro Thr Gly Ser Asn Leu Ile Gly Ala Phe Gly Gly
145                 150                 155                 160 ctg gcc aca gcg cgc ggc aac agc gaa ctg tcg cgg cag ttc ctc gcg          528
Leu Ala Thr Ala Arg Gly Asn Ser Glu Leu Ser Arg Gln Phe Leu Ala
                165                 170                 175 ccg ggc gac gca ctg ctg gac gag tat ttc gac agt gag gca ctc aag          576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa          624
Ala Ala Leu Ala Trp Phe Gly Ala Gln Ser Gly Pro Pro Met Ser Glu
            195                 200                 205 ccg gga acc gct ccg atg gtc ggc ttc gcg gcc ctc atg cac gtc ctg          672
Pro Gly Thr Ala Pro Met Val Gly Phe Ala Ala Leu Met His Val Leu
        210                 215                 220 ccg ccc ggg cga gca gtc gga ggg agc ggc gca ctg agt gct gcg ttg          720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc          768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag          816
Val Thr Ser Ile Arg Arg Asn Ser Asn His Trp Thr Val Thr Thr Glu
            260                 265                 270 agc ggt cga gaa gtt cac gct cgc aag gta atc gcg ggt tgc cac atc          864
Ser Gly Arg Glu Val His Ala Arg Lys Val Ile Ala Gly Cys His Ile
            275                 280                 285 ctc acg aca ctc gat ctc ctg ggc aac gga ggc ttc gac cga acc acg          912
Leu Thr Thr Leu Asp Leu Leu Gly Asn Gly Gly Phe Asp Arg Thr Thr
        290                 295                 300 ctc gat cac tgg cgg cgg aag atc agg gtc ggc ccc ggc atc ggc gct          960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc         1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc         1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct         1104
Ala His Leu Arg Thr Ala His Gly Ala Ala Leu Ala Gly Glu Leu Pro
            355                 360                 365 cct cgc cct gcg gtt ctc gga atg agt ttc agc gga atc gat ccc acg         1152
Pro Arg Pro Ala Val Leu Gly Met Ser Phe Ser Gly Ile Asp Pro Thr
        370                 375                 380 atc gcc ccg gcc ggg cgg cat cag gtg aca ctg tgg tcg cag tgg cag         1200
```

```
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc     1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc     1296
Glu Ala Asp Arg Ile Val Gly Glu Met Glu Ala Phe Ala Pro Gly Phe
            420                 425                 430 acc gat tcc gtc ctc gac cgc ttc att caa act cca cgc gac atc gag     1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca     1392
Ser Glu Leu Gly Met Ile Gly Gly Asn Val Met His Val Glu Met Ser
    450                 455                 460 ctc gat cag atg atg ttg tgg cga ccg ctt ccc gaa ctg tcc ggc cat     1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat     1488
Arg Val Pro Gly Ala Asp Gly Leu Tyr Leu Thr Gly Ala Ser Thr His
                485                 490                 495 ccc ggt ggt ggt gtg tcc gga gcc agc ggt cgc agt gcc gct cga atc     1536
Pro Gly Gly Gly Val Ser Gly Ala Ser Gly Arg Ser Ala Ala Arg Ile
            500                 505                 510 gca ctg tcc gac agc cgc cgg ggt aaa gcg agt cag tgg atg cgt cgt     1584
Ala Leu Ser Asp Ser Arg Arg Gly Lys Ala Ser Gln Trp Met Arg Arg
        515                 520                 525 tcg agc cgc tcg tga                                                  1599
Ser Ser Arg Ser
    530

<210> SEQ ID NO 22
<211> LENGTH: 532
<212> TYPE: PRT
<213> ORGANISM: artificial sequence
<220> FEATURE:
<223> OTHER INFORMATION: Synthetic Construct

<400> SEQUENCE: 22

Met Arg Ala Phe Leu Asp Ala Val Val Gly Ser Gly His Asn Ala
1                 5                   10                  15

Leu Val Ser Ala Ala Tyr Leu Ala Arg Glu Gly Trp Ser Val Glu Val
                20                  25                  30

Leu Glu Lys Asp Met Val Leu Gly Gly Ala Val Ser Thr Val Glu Arg
            35                  40                  45

Phe Pro Gly Tyr Lys Val Asp Arg Gly Ser Ser Ala His Leu Met Ile
        50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Ala Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
    130                 135                 140

Phe Ser Thr Pro Pro Thr Gly Ser Asn Leu Ile Gly Ala Phe Gly Gly
145                 150                 155                 160
```

-continued

Leu Ala Thr Ala Arg Gly Asn Ser Glu Leu Ser Arg Gln Phe Leu Ala
            165                 170                 175

Pro Gly Asp Ala Leu Leu Asp Glu Tyr Phe Asp Ser Glu Ala Leu Lys
        180                 185                 190

Ala Ala Leu Ala Trp Phe Gly Ala Gln Ser Gly Pro Pro Met Ser Glu
    195                 200                 205

Pro Gly Thr Ala Pro Met Val Gly Phe Ala Ala Leu Met His Val Leu
210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
            245                 250                 255

Val Thr Ser Ile Arg Arg Asn Ser Asn His Trp Thr Val Thr Thr Glu
        260                 265                 270

Ser Gly Arg Glu Val His Ala Arg Lys Val Ile Ala Gly Cys His Ile
    275                 280                 285

Leu Thr Thr Leu Asp Leu Leu Gly Asn Gly Gly Phe Asp Arg Thr Thr
290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
            325                 330                 335

Thr Thr Arg Glu Ser Thr Ser Gly Leu Gln Leu Leu Val Ser Asp Arg
        340                 345                 350

Ala His Leu Arg Thr Ala His Gly Ala Leu Ala Gly Glu Leu Pro
    355                 360                 365

Pro Arg Pro Ala Val Leu Gly Met Ser Phe Ser Gly Ile Asp Pro Thr
370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
            405                 410                 415

Glu Ala Asp Arg Ile Val Gly Glu Met Glu Ala Phe Ala Pro Gly Phe
        420                 425                 430

Thr Asp Ser Val Leu Asp Arg Phe Ile Gln Thr Pro Arg Asp Ile Glu
    435                 440                 445

Ser Glu Leu Gly Met Ile Gly Gly Asn Val Met His Val Glu Met Ser
450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
            485                 490                 495

Pro Gly Gly Val Ser Gly Ala Ser Gly Arg Ser Ala Ala Arg Ile
        500                 505                 510

Ala Leu Ser Asp Ser Arg Arg Gly Lys Ala Ser Gln Trp Met Arg Arg
    515                 520                 525

Ser Ser Arg Ser
    530

<210> SEQ ID NO 23
<211> LENGTH: 1599
<212> TYPE: DNA
<213> ORGANISM: artificial sequence
<220> FEATURE:
<223> OTHER INFORMATION: 320M4018

<220> FEATURE:
<221> NAME/KEY: CDS
<222> LOCATION: (1)..(1599)

<400> SEQUENCE: 23

| | | | | | | | | | | | | | | | | |
|---|---|---|---|---|---|---|---|---|---|---|---|---|---|---|---|---|
| atg | agc | gca | ttt | ctc | gac | gcc | gtc | gtc | gtc | ggt | tcc | gga | cac | aac | gcg | 48 |
| Met | Ser | Ala | Phe | Leu | Asp | Ala | Val | Val | Val | Gly | Ser | Gly | His | Asn | Ala | |
| 1 | | | | 5 | | | | | 10 | | | | | 15 | | |
| ctc | gtt | tcg | gcc | gcg | tat | ctc | gca | cgt | gag | ggt | tgg | tcg | gtc | gag | gtt | 96 |
| Leu | Val | Ser | Ala | Ala | Tyr | Leu | Ala | Arg | Glu | Gly | Trp | Ser | Val | Glu | Val | |
| | | | 20 | | | | | 25 | | | | | 30 | | | |
| ctc | gag | aag | gac | acg | gtt | ctc | ggc | ggt | gcc | gtc | tcg | acc | gtc | gag | cga | 144 |
| Leu | Glu | Lys | Asp | Thr | Val | Leu | Gly | Gly | Ala | Val | Ser | Thr | Val | Glu | Arg | |
| | 35 | | | | | 40 | | | | | 45 | | | | | |
| ttt | ccc | gga | tac | aag | gtg | gac | cgg | ggg | tcg | tct | gcg | cac | ctc | atg | atc | 192 |
| Phe | Pro | Gly | Tyr | Lys | Val | Asp | Arg | Gly | Ser | Ser | Ala | His | Leu | Met | Ile | |
| 50 | | | | | 55 | | | | | 60 | | | | | | |
| cga | cac | agt | ggc | atc | atc | gag | gaa | ctc | gga | ctc | ggc | gcg | cac | ggc | ctt | 240 |
| Arg | His | Ser | Gly | Ile | Ile | Glu | Glu | Leu | Gly | Leu | Gly | Ala | His | Gly | Leu | |
| 65 | | | | 70 | | | | | 75 | | | | | 80 | | |
| cgc | tac | atc | gac | tgt | gac | ccg | tgg | gcg | ttc | gct | ccg | ccc | gcc | cct | ggc | 288 |
| Arg | Tyr | Ile | Asp | Cys | Asp | Pro | Trp | Ala | Phe | Ala | Pro | Pro | Ala | Pro | Gly | |
| | | | 85 | | | | | 90 | | | | | 95 | | | |
| acc | gac | ggg | ccg | ggc | atc | gtg | ttt | cat | cgc | gac | ctc | gat | gca | acc | tgc | 336 |
| Thr | Asp | Gly | Pro | Gly | Ile | Val | Phe | His | Arg | Asp | Leu | Asp | Ala | Thr | Cys | |
| | | 100 | | | | | 105 | | | | | 110 | | | | |
| cag | tcc | atc | gaa | cgt | gct | tgc | ggg | aca | aag | gac | gcc | gac | gcg | tac | cgg | 384 |
| Gln | Ser | Ile | Glu | Arg | Ala | Cys | Gly | Thr | Lys | Asp | Ala | Asp | Ala | Tyr | Arg | |
| | 115 | | | | | 120 | | | | | 125 | | | | | |
| cgg | ttc | gtc | gcg | gta | tgg | tcg | gag | cgc | agc | cga | cac | gtg | atg | aag | gca | 432 |
| Arg | Phe | Val | Ala | Val | Trp | Ser | Glu | Arg | Ser | Arg | His | Val | Met | Lys | Ala | |
| 130 | | | | | 135 | | | | | 140 | | | | | | |
| ttt | tcc | tca | ccg | ccc | acc | gga | tcg | aac | ctg | atc | ggt | gcg | ttc | gga | gga | 480 |
| Phe | Ser | Ser | Pro | Pro | Thr | Gly | Ser | Asn | Leu | Ile | Gly | Ala | Phe | Gly | Gly | |
| 145 | | | | | 150 | | | | | 155 | | | | | 160 | |
| ctg | gcc | aca | gcg | cgc | ggc | aac | agc | gaa | ctg | tcg | cgg | cag | ttc | ctc | gcg | 528 |
| Leu | Ala | Thr | Ala | Arg | Gly | Asn | Ser | Glu | Leu | Ser | Arg | Gln | Phe | Leu | Ala | |
| | | | 165 | | | | | 170 | | | | | 175 | | | |
| ccg | ggc | gac | gca | ctg | ctg | gac | gag | tat | ttc | gac | agt | gag | gca | ctc | aag | 576 |
| Pro | Gly | Asp | Ala | Leu | Leu | Asp | Glu | Tyr | Phe | Asp | Ser | Glu | Ala | Leu | Lys | |
| | | 180 | | | | | 185 | | | | | 190 | | | | |
| gca | gcg | ttg | gcg | tgg | ttc | ggc | gcc | cag | tcc | ggg | cct | ccg | atg | tcg | gaa | 624 |
| Ala | Ala | Leu | Ala | Trp | Phe | Gly | Ala | Gln | Ser | Gly | Pro | Pro | Met | Ser | Glu | |
| | 195 | | | | | 200 | | | | | 205 | | | | | |
| ccg | gga | acc | gct | ccg | atg | gtc | ggc | ttc | gcg | gcc | ctc | atg | cac | gtc | ctt | 672 |
| Pro | Gly | Thr | Ala | Pro | Met | Val | Gly | Phe | Ala | Ala | Leu | Met | His | Val | Leu | |
| 210 | | | | | 215 | | | | | 220 | | | | | | |
| ccg | ccc | ggg | cga | gca | gtc | gga | ggg | agc | ggc | gca | ctg | agt | gct | gcg | ttg | 720 |
| Pro | Pro | Gly | Arg | Ala | Val | Gly | Gly | Ser | Gly | Ala | Leu | Ser | Ala | Ala | Leu | |
| 225 | | | | | 230 | | | | | 235 | | | | | 240 | |
| gca | tcc | cgg | atg | gct | gtc | gac | ggc | gcc | acc | gtc | gcg | ctc | ggt | gac | ggc | 768 |
| Ala | Ser | Arg | Met | Ala | Val | Asp | Gly | Ala | Thr | Val | Ala | Leu | Gly | Asp | Gly | |
| | | | 245 | | | | | 250 | | | | | 255 | | | |
| gtg | acg | tcg | atc | cgc | cgg | aac | tcg | aat | cac | tgg | acc | gtc | aca | acc | gag | 816 |
| Val | Thr | Ser | Ile | Arg | Arg | Asn | Ser | Asn | His | Trp | Thr | Val | Thr | Thr | Glu | |
| | | 260 | | | | | 265 | | | | | 270 | | | | |
| agc | ggt | cga | gaa | gtt | cac | gct | cgc | aag | gta | atc | gcg | ggt | tgc | cac | atc | 864 |
| Ser | Gly | Arg | Glu | Val | His | Ala | Arg | Lys | Val | Ile | Ala | Gly | Cys | His | Ile | |
| | 275 | | | | | 280 | | | | | 285 | | | | | |
| ctc | acg | aca | ctc | gat | ctc | ctg | ggc | aac | gga | ggc | ttc | gac | cga | acc | acg | 912 |

```
ctc gat cac tgg cgg cgg aag atc agg gtc ggc ccc ggc atc ggc gct    960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc   1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc   1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct   1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg   1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag   1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc   1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc   1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag   1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg aca   1392
Ser Glu Leu Gly Met Ile Gly Gly Asn Val Met His Val Glu Met Thr
    450                 455                 460 ctc gat cag atg atg ttg tgg cga ccg ctt ccc gaa ctg tcc ggc cat   1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat   1488
Arg Val Pro Gly Ala Asp Gly Leu Tyr Leu Thr Gly Ala Ser Thr His
                485                 490                 495 cct ggt ggt ggt gtg tcc gga gcc agt ggt cgc agt gcc gct cga atc   1536
Pro Gly Gly Gly Val Ser Gly Ala Ser Gly Arg Ser Ala Ala Arg Ile
            500                 505                 510 gca ctg tcc gac agc cgc cgg ggt aaa gcg agt cag tgg atg cgt cgt   1584
Ala Leu Ser Asp Ser Arg Arg Gly Lys Ala Ser Gln Trp Met Arg Arg
        515                 520                 525 ttg agc cgc tcg tga                                               1599
Leu Ser Arg Ser
    530
```

<210> SEQ ID NO 24
<211> LENGTH: 532
<212> TYPE: PRT
<213> ORGANISM: artificial sequence
<220> FEATURE:
<223> OTHER INFORMATION: Synthetic Construct

<400> SEQUENCE: 24

```
Met Ser Ala Phe Leu Asp Ala Val Val Val Gly Ser Gly His Asn Ala
1               5                   10                  15

Leu Val Ser Ala Ala Tyr Leu Ala Arg Glu Gly Trp Ser Val Glu Val
            20                  25                  30
```

-continued

```
Leu Glu Lys Asp Thr Val Leu Gly Ala Val Ser Thr Val Glu Arg
        35                  40                  45
Phe Pro Gly Tyr Lys Val Asp Arg Gly Ser Ser Ala His Leu Met Ile
50                  55                  60
Arg His Ser Gly Ile Ile Glu Glu Leu Gly Leu Gly Ala His Gly Leu
65                  70                  75                  80
Arg Tyr Ile Asp Cys Asp Pro Trp Ala Phe Ala Pro Ala Pro Gly
                85                  90                  95
Thr Asp Gly Pro Gly Ile Val Phe His Arg Asp Leu Asp Ala Thr Cys
            100                 105                 110
Gln Ser Ile Glu Arg Ala Cys Gly Thr Lys Asp Ala Asp Ala Tyr Arg
            115                 120                 125
Arg Phe Val Ala Val Trp Ser Glu Arg Ser Arg His Val Met Lys Ala
130                 135                 140
Phe Ser Ser Pro Pro Thr Gly Ser Asn Leu Ile Gly Ala Phe Gly Gly
145                 150                 155                 160
Leu Ala Thr Ala Arg Gly Asn Ser Glu Leu Ser Arg Gln Phe Leu Ala
                165                 170                 175
Pro Gly Asp Ala Leu Leu Asp Glu Tyr Phe Asp Ser Glu Ala Leu Lys
            180                 185                 190
Ala Ala Leu Ala Trp Phe Gly Ala Gln Ser Gly Pro Pro Met Ser Glu
            195                 200                 205
Pro Gly Thr Ala Pro Met Val Gly Phe Ala Ala Leu Met His Val Leu
            210                 215                 220
Pro Pro Gly Arg Ala Val Gly Gly Ser Gly Ala Leu Ser Ala Ala Leu
225                 230                 235                 240
Ala Ser Arg Met Ala Val Asp Gly Ala Thr Val Ala Leu Gly Asp Gly
                245                 250                 255
Val Thr Ser Ile Arg Arg Asn Ser Asn His Trp Thr Val Thr Thr Glu
            260                 265                 270
Ser Gly Arg Glu Val His Ala Arg Lys Val Ile Ala Gly Cys His Ile
            275                 280                 285
Leu Thr Thr Leu Asp Leu Leu Gly Asn Gly Gly Phe Asp Arg Thr Thr
290                 295                 300
Leu Asp His Trp Arg Arg Lys Ile Arg Val Gly Pro Gly Ile Gly Ala
305                 310                 315                 320
Val Leu Arg Leu Ala Thr Ser Ala Leu Pro Ser Tyr Arg Gly Asp Ala
                325                 330                 335
Thr Thr Arg Glu Ser Thr Ser Gly Leu Gln Leu Leu Val Ser Asp Arg
            340                 345                 350
Ala His Leu Arg Thr Ala His Gly Ala Ala Leu Ala Gly Glu Leu Pro
            355                 360                 365
Pro Arg Pro Ala Val Leu Gly Met Ser Phe Ser Gly Ile Asp Pro Thr
            370                 375                 380
Ile Ala Pro Ala Gly Arg His Gln Val Thr Leu Trp Ser Gln Trp Gln
385                 390                 395                 400
Pro Tyr Arg Leu Ser Gly His Arg Asp Trp Ala Ser Val Ala Glu Ala
                405                 410                 415
Glu Ala Asp Arg Ile Val Gly Glu Met Glu Ala Phe Ala Pro Gly Phe
            420                 425                 430
Thr Asp Ser Val Leu Asp Arg Phe Ile Gln Thr Pro Arg Asp Ile Glu
            435                 440                 445
Ser Glu Leu Gly Met Ile Gly Gly Asn Val Met His Val Glu Met Thr
```

| | | | |
|---|---|---|---|
| | 450 | 455 | 460 |

Leu Asp Gln Met Met Leu Trp Arg Pro Leu Pro Glu Leu Ser Gly His
465 470 475 480

Arg Val Pro Gly Ala Asp Gly Leu Tyr Leu Thr Gly Ala Ser Thr His
                          485                     490                       495

Pro Gly Gly Val Ser Gly Ala Ser Gly Arg Ser Ala Ala Arg Ile
            500                 505                     510

Ala Leu Ser Asp Ser Arg Arg Gly Lys Ala Ser Gln Trp Met Arg Arg
              515                 520                   525

Leu Ser Arg Ser
    530

<210> SEQ ID NO 25
<211> LENGTH: 1599
<212> TYPE: DNA
<213> ORGANISM: artificial sequence
<220> FEATURE:
<223> OTHER INFORMATION: 320M4019
<220> FEATURE:
<221> NAME/KEY: CDS
<222> LOCATION: (1)..(1599)

<400> SEQUENCE: 25

| | | | | | | | | | | | | | | | | |
|---|---|---|---|---|---|---|---|---|---|---|---|---|---|---|---|---|
| atg | aac | gca | ttt | ctc | gac | gcc | gtc | gtc | gtc | ggt | tcc | gga | cac | aac | gcg | 48 |
| Met | Asn | Ala | Phe | Leu | Asp | Ala | Val | Val | Val | Gly | Ser | Gly | His | Asn | Ala | |
| 1 | | | | 5 | | | | | 10 | | | | | 15 | | |

| ctc | gtt | tcg | gcc | gcg | tat | ctc | gca | cgt | gag | ggt | tgg | tcg | gtc | gag | gtt | 96 |
|---|---|---|---|---|---|---|---|---|---|---|---|---|---|---|---|---|
| Leu | Val | Ser | Ala | Ala | Tyr | Leu | Ala | Arg | Glu | Gly | Trp | Ser | Val | Glu | Val | |
| | | | 20 | | | | | 25 | | | | | 30 | | | |

| ctc | gag | aag | gac | acg | gtt | ctc | ggc | ggt | gcc | gtc | tcg | acc | gtc | gag | cga | 144 |
|---|---|---|---|---|---|---|---|---|---|---|---|---|---|---|---|---|
| Leu | Glu | Lys | Asp | Thr | Val | Leu | Gly | Gly | Ala | Val | Ser | Thr | Val | Glu | Arg | |
| | | 35 | | | | | 40 | | | | | 45 | | | | |

| ttt | ccc | gga | tac | aag | gtg | gac | cgg | ggg | tcg | tct | gcg | cac | ctc | atg | atc | 192 |
|---|---|---|---|---|---|---|---|---|---|---|---|---|---|---|---|---|
| Phe | Pro | Gly | Tyr | Lys | Val | Asp | Arg | Gly | Ser | Ser | Ala | His | Leu | Met | Ile | |
| 50 | | | | | 55 | | | | | 60 | | | | | | |

| cga | cac | aat | ggc | atc | atc | gag | gaa | ctc | gga | ctc | ggc | gcg | cac | ggc | ctt | 240 |
|---|---|---|---|---|---|---|---|---|---|---|---|---|---|---|---|---|
| Arg | His | Asn | Gly | Ile | Ile | Glu | Glu | Leu | Gly | Leu | Gly | Ala | His | Gly | Leu | |
| 65 | | | | | 70 | | | | | 75 | | | | | 80 | |

| cgc | tac | atc | gac | tgt | gac | ccg | tgg | gcg | ttc | gct | ccg | ccc | gcc | cct | ggc | 288 |
|---|---|---|---|---|---|---|---|---|---|---|---|---|---|---|---|---|
| Arg | Tyr | Ile | Asp | Cys | Asp | Pro | Trp | Ala | Phe | Ala | Pro | Pro | Ala | Pro | Gly | |
| | | | | 85 | | | | | 90 | | | | | 95 | | |

| acc | gac | ggg | ccg | ggc | atc | gtg | ttt | cat | cgc | gac | ctc | gat | gca | acc | tgc | 336 |
|---|---|---|---|---|---|---|---|---|---|---|---|---|---|---|---|---|
| Thr | Asp | Gly | Pro | Gly | Ile | Val | Phe | His | Arg | Asp | Leu | Asp | Ala | Thr | Cys | |
| | | | 100 | | | | | 105 | | | | | 110 | | | |

| cag | tcc | atc | gaa | cga | gct | tgc | ggg | aca | aag | gac | gcc | gac | gcg | tac | cgg | 384 |
|---|---|---|---|---|---|---|---|---|---|---|---|---|---|---|---|---|
| Gln | Ser | Ile | Glu | Arg | Ala | Cys | Gly | Thr | Lys | Asp | Ala | Asp | Ala | Tyr | Arg | |
| | | 115 | | | | | 120 | | | | | 125 | | | | |

| cgg | ttc | gtc | gcg | gtc | tgg | tcg | gag | cgc | agc | cga | cac | gtg | atg | aag | gca | 432 |
|---|---|---|---|---|---|---|---|---|---|---|---|---|---|---|---|---|
| Arg | Phe | Val | Ala | Val | Trp | Ser | Glu | Arg | Ser | Arg | His | Val | Met | Lys | Ala | |
| 130 | | | | | 135 | | | | | 140 | | | | | | |

| tct | tcc | aca | ccg | ccc | acc | gga | tcg | aac | ctg | atc | ggt | gcg | ttc | gga | gga | 480 |
|---|---|---|---|---|---|---|---|---|---|---|---|---|---|---|---|---|
| Ser | Ser | Thr | Pro | Pro | Thr | Gly | Ser | Asn | Leu | Ile | Gly | Ala | Phe | Gly | Gly | |
| 145 | | | | | 150 | | | | | 155 | | | | | 160 | |

| ctg | gcc | aca | gcg | cgc | ggc | aac | agc | gaa | ctg | tcg | cgg | cag | ttc | ctc | gcg | 528 |
|---|---|---|---|---|---|---|---|---|---|---|---|---|---|---|---|---|
| Leu | Ala | Thr | Ala | Arg | Gly | Asn | Ser | Glu | Leu | Ser | Arg | Gln | Phe | Leu | Ala | |
| | | | 165 | | | | | 170 | | | | | 175 | | | |

| ccg | ggc | gac | gca | ctg | ctg | gac | gag | tat | ttc | gac | agt | gag | gca | ctc | aag | 576 |
|---|---|---|---|---|---|---|---|---|---|---|---|---|---|---|---|---|
| Pro | Gly | Asp | Ala | Leu | Leu | Asp | Glu | Tyr | Phe | Asp | Ser | Glu | Ala | Leu | Lys | |
| | | | 180 | | | | | 185 | | | | | 190 | | | |

| gca | gcg | ttg | gcg | tgg | ttc | ggc | gcc | cag | tcc | ggg | cct | ccg | atg | tcg | gaa | 624 |
|---|---|---|---|---|---|---|---|---|---|---|---|---|---|---|---|---|

```
                 Ala Ala Leu Ala Trp Phe Gly Ala Gln Ser Gly Pro Pro Met Ser Glu
                         195                 200                 205 ccg gga acc gct ccg atg gtc ggc ttc gcg gcc ctc atg cac gtc ctg          672
Pro Gly Thr Ala Pro Met Val Gly Phe Ala Ala Leu Met His Val Leu
        210                 215                 220 ccg ccc ggg cga gca gtc gga ggg agc ggc gca ctg agt gct gcg ttg          720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc          768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag          816
Val Thr Ser Ile Arg Arg Asn Ser Asn His Trp Thr Val Thr Thr Glu
            260                 265                 270 agc ggt cga gaa gtt cac gct cgc aag gta atc gcg ggt tgc cac atc          864
Ser Gly Arg Glu Val His Ala Arg Lys Val Ile Ala Gly Cys His Ile
        275                 280                 285 ctc acg aca ctc gat ctc ctg ggc aac gga ggc ttc gac cgg acc acg          912
Leu Thr Thr Leu Asp Leu Leu Gly Asn Gly Gly Phe Asp Arg Thr Thr
        290                 295                 300 ctc gat cac tgg cgg cgg aag atc agg gtc ggc ccc ggc atc ggc gct          960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc         1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc         1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct         1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg         1152
Pro Arg Pro Ala Val Leu Gly Met Ser Phe Ser Gly Ile Asp Pro Thr
        370                 375                 380 atc gcc ccg gcc ggg cgg cat cag gtg aca ctg tgg tcg cag tgg cag         1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc         1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc         1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc ggc atc gag         1344
Thr Asp Ser Val Leu Asp Arg Phe Ile Gln Thr Pro Arg Gly Ile Glu
        435                 440                 445 tcg gaa ttg ggg atg atc ggc gga aat gtc atg cac gtc gag atg tca         1392
Ser Glu Leu Gly Met Ile Gly Gly Asn Val Met His Val Glu Met Ser
        450                 455                 460 ctc gat cag atg atg ttg tgg cga ccg ctt ccc gaa ctg tcc ggc cat         1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat         1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc         1536
Pro Gly Gly Gly Val Ser Gly Ala Ser Gly Arg Ser Ala Ala Arg Ile
            500                 505                 510
```

```
gca ctg tcc gac agc cgc cgg ggt aaa gcg agt cag tgg atg cgt cgt    1584
Ala Leu Ser Asp Ser Arg Arg Gly Lys Ala Ser Gln Trp Met Arg Arg
        515                 520                 525 tcg agc cgc tcg tga                                                1599
Ser Ser Arg Ser
    530
```

<210> SEQ ID NO 26
<211> LENGTH: 532
<212> TYPE: PRT
<213> ORGANISM: artificial sequence
<220> FEATURE:
<223> OTHER INFORMATION: Synthetic Construct

<400> SEQUENCE: 26

```
Met Asn Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ala His Leu Met Ile
50                  55                  60

Arg His Asn Gly Ile Ile Glu Glu Leu Gly Leu Gly Ala His Gly Leu
65              70                  75                      80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
    130                 135                 140

Ser Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
```

-continued

```
                    325                 330                 335
Thr Thr Arg Glu Ser Thr Ser Gly Leu Gln Leu Leu Val Ser Asp Arg
                340                 345                 350

Ala His Leu Arg Thr Ala His Gly Ala Ala Leu Ala Gly Glu Leu Pro
            355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Gly Ile Glu
    435                 440                 445

Ser Glu Leu Gly Met Ile Gly Gly Asn Val Met His Val Glu Met Ser
450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Met Arg Arg
    515                 520                 525

Ser Ser Arg Ser
    530

<210> SEQ ID NO 27
<211> LENGTH: 1599
<212> TYPE: DNA
<213> ORGANISM: artificial sequence
<220> FEATURE:
<223> OTHER INFORMATION: 320M4020
<220> FEATURE:
<221> NAME/KEY: CDS
<222> LOCATION: (1)..(1599)

<400> SEQUENCE: 27 atg agc gca ttt ctc gac gcc gtc gtc gtc ggt tcc gga cac aac gcg    48
Met Ser Ala Phe Leu Asp Ala Val Val Val Gly Ser Gly His Asn Ala
1               5                   10                  15 ctc gtt tcg gcc gcg tat ctc gca cgt gag ggt tgg tcg gtc gag gtt    96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga   144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc   192
Phe Pro Gly Tyr Lys Val Asp Arg Gly Ser Ser Ala His Leu Met Ile
    50                  55                  60 cga cac agt ggc atc atc gag gaa ctc gga ctc ggc gcg cac ggc ctt   240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc   288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc   336
Thr Asp Gly Pro Gly Ile Val Phe His Arg Asp Leu Asp Ala Thr Cys
```

-continued

```
                Thr Asp Gly Pro Gly Ile Val Phe His Arg Asp Leu Asp Ala Thr Cys
                                100                 105                 110 cag tcc atc gaa cga gct tgc ggg aca aag gac gcc gac gcg tac cgg        384
Gln Ser Ile Glu Arg Ala Cys Gly Thr Lys Asp Ala Asp Ala Tyr Arg
            115                 120                 125 cgg ttc gtc gcg gtc tgg tcg gag cgc agc cga cac gtg ttg aag gca        432
Arg Phe Val Ala Val Trp Ser Glu Arg Ser Arg His Val Leu Lys Ala
    130                 135                 140 ttt tcc aca ccg ccc acc gga tcg aac ctg atc ggt gcg ttc gga gga        480
Phe Ser Thr Pro Pro Thr Gly Ser Asn Leu Ile Gly Ala Phe Gly Gly
145                 150                 155                 160 ctg gcc aca gtg cgc ggc aac agc gaa ctg tcg cgg cag ttc ctc gcg        528
Leu Ala Thr Val Arg Gly Asn Ser Glu Leu Ser Arg Gln Phe Leu Ala
                165                 170                 175 ccg ggc gac gca ctg ctg gac gag tat ttc gac agt gag gca ctc aag        576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa        624
Ala Ala Leu Ala Trp Phe Gly Ala Gln Ser Gly Pro Pro Met Ser Glu
    195                 200                 205 ccg gga acc gct ccg atg gtc ggc ttc gcg gcc ctc atg cac gtc ctg        672
Pro Gly Thr Ala Pro Met Val Gly Phe Ala Ala Leu Met His Val Leu
210                 215                 220 ccg ccc ggg cga gca gtc gga ggg agc ggc gca ctg agt gct gcg ttg        720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc        768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag        816
Val Thr Ser Ile Arg Arg Asn Ser Asn His Trp Thr Val Thr Thr Glu
            260                 265                 270 agc ggt cga gaa gtt cac gct cgc aag gta gtc gcg ggt tgc cac atc        864
Ser Gly Arg Glu Val His Ala Arg Lys Val Val Ala Gly Cys His Ile
    275                 280                 285 ctc acg aca ctc gat ctc ctg ggc aac gga ggc ttc gac cga acc acg        912
Leu Thr Thr Leu Asp Leu Leu Gly Asn Gly Gly Phe Asp Arg Thr Thr
290                 295                 300 ctc gat cac tgg cgg cgg aag atc agg gtc ggc ccc ggc atc ggc gct        960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc       1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc       1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct       1104
Ala His Leu Arg Thr Ala His Gly Ala Ala Leu Ala Gly Glu Leu Pro
    355                 360                 365 cct cgc cct gcg gtt ctc gga atg agt ttc agc gga atc gat ccc acg       1152
Pro Arg Pro Ala Val Leu Gly Met Ser Phe Ser Gly Ile Asp Pro Thr
370                 375                 380 atc gcc ccg gcc ggg cgg cat cag gtg aca ctg tgg tcg cag tgg cag       1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc       1248
Pro Tyr Arg Leu Ser Gly His Arg Asp Trp Ala Ser Val Ala Glu Ala
                405                 410                 415
```

-continued

```
gag gcc gac cgg atc gtc ggc gag atg gag gct ttt gca ccc gga ttc      1296
Glu Ala Asp Arg Ile Val Gly Glu Met Glu Ala Phe Ala Pro Gly Phe
        420                 425                 430 acc gat tcc gtc ctc gac cgc ttc att caa act ccc cgc gac atc gag      1344
Thr Asp Ser Val Leu Asp Arg Phe Ile Gln Thr Pro Arg Asp Ile Glu
    435                 440                 445 tcg gaa ttg ggg atg atc ggc gga aat gtc atg cac gtc gag atg tca      1392
Ser Glu Leu Gly Met Ile Gly Gly Asn Val Met His Val Glu Met Ser
450                 455                 460 ctc gat cag atg atg ttg tgg cga ccg ctt ccc gaa ctg tcc ggc cat      1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat      1488
Arg Val Pro Gly Ala Asp Gly Leu Tyr Leu Thr Gly Ala Ser Thr His
            485                 490                 495 ccc ggt ggt ggt gtg tcc gga gcc agt ggt cgc agt gcc gct cga atc      1536
Pro Gly Gly Gly Val Ser Gly Ala Ser Gly Arg Ser Ala Ala Arg Ile
        500                 505                 510 gca ctg tcc gac agc cgc cgg ggt aaa gcg agt cag tgg atg cgt cgt      1584
Ala Leu Ser Asp Ser Arg Arg Gly Lys Ala Ser Gln Trp Met Arg Arg
    515                 520                 525 tcg agc cgc tcg tga                                                   1599
Ser Ser Arg Ser
        530

<210> SEQ ID NO 28
<211> LENGTH: 532
<212> TYPE: PRT
<213> ORGANISM: artificial sequence
<220> FEATURE:
<223> OTHER INFORMATION: Synthetic Construct

<400> SEQUENCE: 28

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg
        35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Leu Lys Ala
    130                 135                 140

Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
```

-continued

```
                195                 200                 205
Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Val Ala Gly Cys His Ile
    275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
    355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
    435                 440                 445

Ser Glu Leu Gly Met Ile Gly Gly Asn Val Met His Val Glu Met Ser
    450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Met Arg Arg
    515                 520                 525

Ser Ser Arg Ser
    530

<210> SEQ ID NO 29
<211> LENGTH: 1599
<212> TYPE: DNA
<213> ORGANISM: artificial sequence
<220> FEATURE:
<223> OTHER INFORMATION: 320M4023
<220> FEATURE:
<221> NAME/KEY: CDS
<222> LOCATION: (1)..(1599)

<400> SEQUENCE: 29 atg aga gca ttt ctc gac gcc gtc gtc gtc ggt tcc gga cac aac gcg      48
```

```
Met Arg Ala Phe Leu Asp Ala Val Val Val Gly Ser Gly His Asn Ala
1               5                   10                  15 ctc gtt tcg gcc gcg tat ctc gca cgt gag ggt tgg tcg gtc gag gtt    96
Leu Val Ser Ala Ala Tyr Leu Ala Arg Glu Gly Trp Ser Val Glu Val
                20                  25                  30 ctc gag aag gat acg gtt ctc ggc ggt gcc gtc tcg acc gtc gag cga   144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc   192
Phe Pro Gly Tyr Lys Val Asp Arg Gly Ser Ser Ala His Leu Met Ile
    50                  55                  60 cga cac agt ggc atc atc gag gaa ctc gga ctc ggc gcg cac ggc ctt   240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc   288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc   336
Thr Asp Gly Pro Gly Ile Val Phe His Arg Asp Leu Asp Ala Thr Cys
            100                 105                 110 cag tcc atc gaa cga gct tgc ggg aca aag gac gcc gac gcg tac cgg   384
Gln Ser Ile Glu Arg Ala Cys Gly Thr Lys Asp Ala Asp Ala Tyr Arg
    115                 120                 125 cgg ttc gtc gcg gtc tgg tcg gag cgc agc cga cac gtg atg aag gca   432
Arg Phe Val Ala Val Trp Ser Glu Arg Ser Arg His Val Met Lys Ala
130                 135                 140 ttt tcc aca ccg ccc acc gga tcg aac ctg atc ggt gcg ttc gga gga   480
Phe Ser Thr Pro Pro Thr Gly Ser Asn Leu Ile Gly Ala Phe Gly Gly
145                 150                 155                 160 ctg gcc aca gcg cgc ggc aac agc gaa ctg tcg cgg cag ttc ctc gcg   528
Leu Ala Thr Ala Arg Gly Asn Ser Glu Leu Ser Arg Gln Phe Leu Ala
                165                 170                 175 ccg ggc gac gca ctg ctg gac gag tat ttc gac agt gag gca ctc aag   576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa   624
Ala Ala Leu Ala Trp Phe Gly Ala Gln Ser Gly Pro Pro Met Ser Glu
    195                 200                 205 ccg gga acc gct ccg atg gtc ggc ttc gcg gcc ctc atg cac gtc ctg   672
Pro Gly Thr Ala Pro Met Val Gly Phe Ala Ala Leu Met His Val Leu
210                 215                 220 ccg ccc ggg cga gca gtc gga ggg agc ggc gca ctg agt gct gcg ttg   720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc   768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag   816
Val Thr Ser Ile Arg Arg Asn Ser Asn His Trp Thr Val Thr Thr Glu
            260                 265                 270 agc ggt cga gaa gtt cac gct cgc aag gta atc gcg ggt tgc cac atc   864
Ser Gly Arg Glu Val His Ala Arg Lys Val Ile Ala Gly Cys His Ile
    275                 280                 285 ctc acg aca ctc ggt ctc ctg ggc aac gga ggc ttc gac cga acc acg   912
Leu Thr Thr Leu Gly Leu Leu Gly Asn Gly Gly Phe Asp Arg Thr Thr
290                 295                 300 ctc gat cac tgg cgg cgg aag atc agg gtc ggc ccc ggc atc ggc gct   960
Leu Asp His Trp Arg Arg Lys Ile Arg Val Gly Pro Gly Ile Gly Ala
305                 310                 315                 320
```

```
gta ttg cga ctg gcg aca tct gcg ctc ccg tcc tac cgc ggc gac gcc    1008
Val Leu Arg Leu Ala Thr Ser Ala Leu Pro Ser Tyr Arg Gly Asp Ala
            325                 330                 335 acg aca cgg gaa agt acc tcg gga ttg caa tta ctc gtt tcc gat cgc    1056
Thr Thr Arg Glu Ser Thr Ser Gly Leu Gln Leu Leu Val Ser Asp Arg
    340                 345                 350 gcc cac ttg cgc act gca cac ggc gca gca ctg gca ggg gaa ctg cct    1104
Ala His Leu Arg Thr Ala His Gly Ala Ala Leu Ala Gly Glu Leu Pro
355                 360                 365 cct cgc cct gcg gtt ctc gga atg agt ttc agc gga atc gat ccc acg    1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag    1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc    1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc    1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag    1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca    1392
Ser Glu Leu Gly Met Ile Gly Gly Asn Val Met His Val Glu Met Ser
450                 455                 460 ctc gat cag atg atg ttg tgg cga ccg ctt ccc gaa ctg tcc ggc cat    1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat    1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc    1536
Pro Gly Gly Gly Val Ser Gly Ala Ser Gly Arg Ser Ala Ala Arg Ile
            500                 505                 510 gca ctg tcc gac agc cgc cgg ggt aaa gcg agt cag tgg atg cgt cgt    1584
Ala Leu Ser Asp Ser Arg Arg Gly Lys Ala Ser Gln Trp Met Arg Arg
        515                 520                 525 tcg agc cgc tcg tga                                                 1599
Ser Ser Arg Ser
    530
```

<210> SEQ ID NO 30
<211> LENGTH: 532
<212> TYPE: PRT
<213> ORGANISM: artificial sequence
<220> FEATURE:
<223> OTHER INFORMATION: Synthetic Construct

<400> SEQUENCE: 30

```
Met Arg Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg
        35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
```

-continued

```
            65                  70                  75                  80
Arg Tyr Ile Asp Cys Asp Pro Trp Ala Phe Ala Pro Ala Pro Gly
                85                  90                  95
Thr Asp Gly Pro Gly Ile Val Phe His Arg Asp Leu Asp Ala Thr Cys
                100                 105                 110
Gln Ser Ile Glu Arg Ala Cys Gly Thr Lys Asp Ala Asp Ala Tyr Arg
                115                 120                 125
Arg Phe Val Ala Val Trp Ser Glu Arg Ser Arg His Val Met Lys Ala
                130                 135                 140
Phe Ser Thr Pro Pro Thr Gly Ser Asn Leu Ile Gly Ala Phe Gly Gly
145                 150                 155                 160
Leu Ala Thr Ala Arg Gly Asn Ser Glu Leu Ser Arg Gln Phe Leu Ala
                165                 170                 175
Pro Gly Asp Ala Leu Leu Asp Glu Tyr Phe Asp Ser Glu Ala Leu Lys
                180                 185                 190
Ala Ala Leu Ala Trp Phe Gly Ala Gln Ser Gly Pro Pro Met Ser Glu
                195                 200                 205
Pro Gly Thr Ala Pro Met Val Gly Phe Ala Ala Leu Met His Val Leu
                210                 215                 220
Pro Pro Gly Arg Ala Val Gly Gly Ser Gly Ala Leu Ser Ala Ala Leu
225                 230                 235                 240
Ala Ser Arg Met Ala Val Asp Gly Ala Thr Val Ala Leu Gly Asp Gly
                245                 250                 255
Val Thr Ser Ile Arg Arg Asn Ser Asn His Trp Thr Val Thr Thr Glu
                260                 265                 270
Ser Gly Arg Glu Val His Ala Arg Lys Val Ile Ala Gly Cys His Ile
                275                 280                 285
Leu Thr Thr Leu Gly Leu Leu Gly Asn Gly Gly Phe Asp Arg Thr Thr
                290                 295                 300
Leu Asp His Trp Arg Arg Lys Ile Arg Val Gly Pro Gly Ile Gly Ala
305                 310                 315                 320
Val Leu Arg Leu Ala Thr Ser Ala Leu Pro Ser Tyr Arg Gly Asp Ala
                325                 330                 335
Thr Thr Arg Glu Ser Thr Ser Gly Leu Gln Leu Leu Val Ser Asp Arg
                340                 345                 350
Ala His Leu Arg Thr Ala His Gly Ala Ala Leu Ala Gly Glu Leu Pro
                355                 360                 365
Pro Arg Pro Ala Val Leu Gly Met Ser Phe Ser Gly Ile Asp Pro Thr
                370                 375                 380
Ile Ala Pro Ala Gly Arg His Gln Val Thr Leu Trp Ser Gln Trp Gln
385                 390                 395                 400
Pro Tyr Arg Leu Ser Gly His Arg Asp Trp Ala Ser Val Ala Glu Ala
                405                 410                 415
Glu Ala Asp Arg Ile Val Gly Glu Met Glu Ala Phe Ala Pro Gly Phe
                420                 425                 430
Thr Asp Ser Val Leu Asp Arg Phe Ile Gln Thr Pro Arg Asp Ile Glu
                435                 440                 445
Ser Glu Leu Gly Met Ile Gly Gly Asn Val Met His Val Glu Met Ser
                450                 455                 460
Leu Asp Gln Met Met Leu Trp Arg Pro Leu Pro Glu Leu Ser Gly His
465                 470                 475                 480
Arg Val Pro Gly Ala Asp Gly Leu Tyr Leu Thr Gly Ala Ser Thr His
                485                 490                 495
```

```
Pro Gly Gly Val Ser Gly Ala Ser Gly Arg Ser Ala Ala Arg Ile
        500                 505                 510
Ala Leu Ser Asp Ser Arg Arg Gly Lys Ala Ser Gln Trp Met Arg Arg
    515                 520                 525
Ser Ser Arg Ser
    530

<210> SEQ ID NO 31
<211> LENGTH: 1599
<212> TYPE: DNA
<213> ORGANISM: artificial sequence
<220> FEATURE:
<223> OTHER INFORMATION: 320M4027
<220> FEATURE:
<221> NAME/KEY: CDS
<222> LOCATION: (1)..(1599)

<400> SEQUENCE: 31 atg agc gca ttt ctc gac gcc gtc gtc gtc ggt tcc gga cac aac gcg      48
Met Ser Ala Phe Leu Asp Ala Val Val Val Gly Ser Gly His Asn Ala
1               5                   10                  15 ctc gtt tcg gcc gcg tat ctc gca cgt gag ggt tgg tcg gtc gag gtt      96
Leu Val Ser Ala Ala Tyr Leu Ala Arg Glu Gly Trp Ser Val Glu Val
            20                  25                  30 ctc gag aag gac acg gtt ctc ggc ggt gcc gtc tcg acc gtc gag cga      144
Leu Glu Lys Asp Thr Val Leu Gly Gly Ala Val Ser Thr Val Glu Arg
        35                  40                  45 ttt ccc gga tac aag gtg gac cgg ggg tcg tct gcg cac ctc atg atc      192
Phe Pro Gly Tyr Lys Val Asp Arg Gly Ser Ser Ala His Leu Met Ile
    50                  55                  60 cga cac agt ggc atc atc gag gaa ctc gga ctc ggc gcg cac ggc ctt      240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc      288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc      336
Thr Asp Gly Pro Gly Ile Val Phe His Arg Asp Leu Asp Ala Thr Cys
            100                 105                 110 cag tcc atc gaa cga gct tgc ggg aca aag gac gcc gac gcg tac cgg      384
Gln Ser Ile Glu Arg Ala Cys Gly Thr Lys Asp Ala Asp Ala Tyr Arg
        115                 120                 125 cgg ttc gtc gcg gtc tgg tcg gag cgc agc cga cac gtg atg aag gca      432
Arg Phe Val Ala Val Trp Ser Glu Arg Ser Arg His Val Met Lys Ala
    130                 135                 140 ttt tcc aca ccg ccc acc gga tcg aac ctg atc ggt gcg ttc gga gga      480
Phe Ser Thr Pro Pro Thr Gly Ser Asn Leu Ile Gly Ala Phe Gly Gly
145                 150                 155                 160 ctg gcc aca gcg cgc ggc aac agc gaa ctg tcg cgg cag ttc ctc gcg      528
Leu Ala Thr Ala Arg Gly Asn Ser Glu Leu Ser Arg Gln Phe Leu Ala
                165                 170                 175 ccg ggc gac gca ctg ctg gac gag tat ttc gac agt gag gca ctc aag      576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa      624
Ala Ala Leu Ala Trp Phe Gly Ala Gln Ser Gly Pro Pro Met Ser Glu
        195                 200                 205 ccg gga acc gct ccg atg gtc ggc ttc gcg gcc ctc atg cac gtc ctg      672
Pro Gly Thr Ala Pro Met Val Gly Phe Ala Ala Leu Met His Val Leu
    210                 215                 220
```

```
ccg ccc ggg cga gca gtc gga ggg agc ggc gca ctg agt gct gcg ttg         720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc         768
Ala Ser Arg Met Ala Val Asp Gly Ala Thr Val Ala Leu Gly Asp Gly
            245                 250                 255 gtg acg tcg atc cgc cgg aac tcg aat cac tgg acc gtc aca acc gag         816
Val Thr Ser Ile Arg Arg Asn Ser Asn His Trp Thr Val Thr Thr Glu
        260                 265                 270 agc ggt cga gaa gtt cac gct cgc aag gta atc gcg ggt tgc cac atc         864
Ser Gly Arg Glu Val His Ala Arg Lys Val Ile Ala Gly Cys His Ile
    275                 280                 285 ctc acg aca ctc gat ctc ctg ggc aac gga ggc ttc gac cga acc acg         912
Leu Thr Thr Leu Asp Leu Leu Gly Asn Gly Gly Phe Asp Arg Thr Thr
290                 295                 300 ctc gat cac tgg cgg cgg aag atc agg gtc ggc ccc ggc atc ggc gct         960
Leu Asp His Trp Arg Arg Lys Ile Arg Val Gly Pro Gly Ile Gly Ala
305                 310                 315                 320 gta ttg cga ctg gcg aca tct gcg ctc ccg tct tac cgc ggc gac gcc        1008
Val Leu Arg Leu Ala Thr Ser Ala Leu Pro Ser Tyr Arg Gly Asp Ala
            325                 330                 335 acg aca cgg gaa agt acc tcg gga ttg caa tta ctc gtt tcc gat cgc        1056
Thr Thr Arg Glu Ser Thr Ser Gly Leu Gln Leu Leu Val Ser Asp Arg
        340                 345                 350 gcc cac ttg cgc act gca cac ggc gca gca ctg gca ggg gaa ctg cct        1104
Ala His Leu Arg Thr Ala His Gly Ala Ala Leu Ala Gly Glu Leu Pro
    355                 360                 365 cct cgc cct gcg gtt ctc gga atg agt ttc agc gga atc gat ccc acg        1152
Pro Arg Pro Ala Val Leu Gly Met Ser Phe Ser Gly Ile Asp Pro Thr
370                 375                 380 atc gcc ccg gcc ggg cgg cat cag gtg aca ctg tgg tcg cag tgg cag        1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc        1248
Pro Tyr Arg Leu Ser Gly His Arg Asp Trp Ala Ser Val Ala Glu Ala
            405                 410                 415 gag gcc gac cgg atc gtc ggc gag atg gag gct ttt gca ccc gga ttc        1296
Glu Ala Asp Arg Ile Val Gly Glu Met Glu Ala Phe Ala Pro Gly Phe
        420                 425                 430 acc gat tcc gtc ctc gac cgc ttc att caa act ccc cgc gac atc gag        1344
Thr Asp Ser Val Leu Asp Arg Phe Ile Gln Thr Pro Arg Asp Ile Glu
    435                 440                 445 tcg gaa ttg ggg atg atc ggc gga aat gtc atg cac gtc gag atg tca        1392
Ser Glu Leu Gly Met Ile Gly Gly Asn Val Met His Val Glu Met Ser
450                 455                 460 ctc gat cag atg atg ttg tgg cga ccg ctt ccc gaa ctg tcc ggc cat        1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat        1488
Arg Val Pro Gly Ala Asp Gly Leu Tyr Leu Thr Gly Ala Ser Thr His
            485                 490                 495 ccc ggt ggt ggt gtg tcc gga gcc agt ggt cgc agt gcc gct cga atc        1536
Pro Gly Gly Gly Val Ser Gly Ala Ser Gly Arg Ser Ala Ala Arg Ile
        500                 505                 510 gca ctg tcc gac agc cgc tgg ggt aaa gcg agt cag tgg atg cgt cgt        1584
Ala Leu Ser Asp Ser Arg Trp Gly Lys Ala Ser Gln Trp Met Arg Arg
    515                 520                 525 tcg agc cgc tcg tga                                                    1599
Ser Ser Arg Ser
    530
```

<210> SEQ ID NO 32
<211> LENGTH: 532
<212> TYPE: PRT
<213> ORGANISM: artificial sequence
<220> FEATURE:
<223> OTHER INFORMATION: Synthetic Construct

<400> SEQUENCE: 32

```
Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                    85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
    130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365
```

```
Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
        435                 440                 445

Ser Glu Leu Gly Met Ile Gly Gly Asn Val Met His Val Glu Met Ser
    450                 455                 460

Leu Asp Gln Met Met Leu Trp Arg Pro Leu Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Trp Gly Lys Ala Ser Gln Trp Met Arg Arg
        515                 520                 525

Ser Ser Arg Ser
    530

<210> SEQ ID NO 33
<211> LENGTH: 1599
<212> TYPE: DNA
<213> ORGANISM: artificial sequence
<220> FEATURE:
<223> OTHER INFORMATION: 320M4032
<220> FEATURE:
<221> NAME/KEY: CDS
<222> LOCATION: (1)..(1599)

<400> SEQUENCE: 33 atg agc gca ttt ctc gac gcc gtc gtc gtc ggt tcc gga cac aac ggg      48
Met Ser Ala Phe Leu Asp Ala Val Val Val Gly Ser Gly His Asn Gly
1               5                   10                  15 ctc gtt tcg gcc gcg tat ctc gca cgt gag ggt tgg tcg gtc gag gtt      96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc     288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc     336
Thr Asp Gly Pro Gly Ile Val Phe His Arg Asp Leu Asp Ala Thr Cys
            100                 105                 110 cag tcc atc gaa cga gct tgc ggg aca aag gac gcc gac gcg tac cgg     384
Gln Ser Ile Glu Arg Ala Cys Gly Thr Lys Asp Ala Asp Ala Tyr Arg
        115                 120                 125
```

| | | |
|---|---|---|
| cgg ttc gtc gcg gtc tgg tcg gag cgc agc cga cac gtg atg aag gca<br>Arg Phe Val Ala Val Trp Ser Glu Arg Ser Arg His Val Met Lys Ala<br>130                                 135                           140 | 432 |
| ttt tcc aca ccg ccc acc gga tcg aac ctg atc ggt gcg ttc gga gga<br>Phe Ser Thr Pro Pro Thr Gly Ser Asn Leu Ile Gly Ala Phe Gly Gly<br>145                                 150                           155                           160 | 480 |
| ctg gcc aca gcg cgc ggc aac agc gaa ctg tcg cgg cag ttc ctc gcg<br>Leu Ala Thr Ala Arg Gly Asn Ser Glu Leu Ser Arg Gln Phe Leu Ala<br>                          165                           170                           175 | 528 |
| ccg ggc gac gca ctg ctg gac gag tat ttc gac agt gag gca ctc aag<br>Pro Gly Asp Ala Leu Leu Asp Glu Tyr Phe Asp Ser Glu Ala Leu Lys<br>                    180                           185                           190 | 576 |
| gca gcg ttg gcg tgg ttc ggc gcc cag tcc ggg cct ccg atg tcg gaa<br>Ala Ala Leu Ala Trp Phe Gly Ala Gln Ser Gly Pro Pro Met Ser Glu<br>               195                           200                           205 | 624 |
| ccg gga acc gct ccg atg gtc ggc ttc gcc gcc ctc atg cac gtc ctg<br>Pro Gly Thr Ala Pro Met Val Gly Phe Ala Ala Leu Met His Val Leu<br>          210                           215                           220 | 672 |
| ccg ccc ggg cga gca gtc gga ggg agc ggc gca ctg agt gct gcg ctg<br>Pro Pro Gly Arg Ala Val Gly Gly Ser Gly Ala Leu Ser Ala Ala Leu<br>225                                 230                           235                           240 | 720 |
| gca tcc cgg atg gct gtc gac ggc gcc acc gtc gcg ctc ggt gac ggc<br>Ala Ser Arg Met Ala Val Asp Gly Ala Thr Val Ala Leu Gly Asp Gly<br>                          245                           250                           255 | 768 |
| gtg acg tcg atc cgc cgg aac tcg aat cac tgg acc gtc aca acc gag<br>Val Thr Ser Ile Arg Arg Asn Ser Asn His Trp Thr Val Thr Thr Glu<br>                    260                           265                           270 | 816 |
| agc ggt cga gag gtt cac gct cgc aag gta atc gcg ggt tgc cac atc<br>Ser Gly Arg Glu Val His Ala Arg Lys Val Ile Ala Gly Cys His Ile<br>               275                           280                           285 | 864 |
| ctc acg aca ctc gat ctc ctg ggc aac gga ggc ttc gac cga acc acg<br>Leu Thr Thr Leu Asp Leu Leu Gly Asn Gly Gly Phe Asp Arg Thr Thr<br>          290                           295                           300 | 912 |
| ctc gat cac tgg cgg cgg aag atc agg gtc ggc ccc ggc atc ggc gct<br>Leu Asp His Trp Arg Arg Lys Ile Arg Val Gly Pro Gly Ile Gly Ala<br>305                                 310                           315                           320 | 960 |
| gta ttg cga ctg gcg aca tct gcg ctc ccg tcc tac cgc ggc gac gcc<br>Val Leu Arg Leu Ala Thr Ser Ala Leu Pro Ser Tyr Arg Gly Asp Ala<br>                          325                           330                           335 | 1008 |
| acg aca cgg gaa agt acc tcg gga ttg caa tta ctc gtt tcc gat cgc<br>Thr Thr Arg Glu Ser Thr Ser Gly Leu Gln Leu Leu Val Ser Asp Arg<br>                    340                           345                           350 | 1056 |
| gcc cac ttg cgc act gca cac ggc gca gca ctg gca ggg gaa ctg cct<br>Ala His Leu Arg Thr Ala His Gly Ala Ala Leu Ala Gly Glu Leu Pro<br>               355                           360                           365 | 1104 |
| cct cgc cct gcg gtt ctc gga atg agt ttc agc gga atc gat ccc acg<br>Pro Arg Pro Ala Val Leu Gly Met Ser Phe Ser Gly Ile Asp Pro Thr<br>370                                 375                           380 | 1152 |
| atc gcc ccg gcc ggg cgg cat cag gtg aca ctg tgg tcg cag tgg cag<br>Ile Ala Pro Ala Gly Arg His Gln Val Thr Leu Trp Ser Gln Trp Gln<br>385                                 390                           395                           400 | 1200 |
| ccg tat cgt ctc agc gga cat cgc gat tgg gcg tcg gtc gcc gag gcc<br>Pro Tyr Arg Leu Ser Gly His Arg Asp Trp Ala Ser Val Ala Glu Ala<br>                          405                           410                           415 | 1248 |
| gag gcc gac cgg atc gtc ggc gag atg gag gct tat gca ccc gga ttc<br>Glu Ala Asp Arg Ile Val Gly Glu Met Glu Ala Tyr Ala Pro Gly Phe<br>                    420                           425                           430 | 1296 |
| acc gat tcc gtc ctc gac cgc ttc att caa act ccc cgc gac atc gag<br>Thr Asp Ser Val Leu Asp Arg Phe Ile Gln Thr Pro Arg Asp Ile Glu<br>                          435                           440                           445 | 1344 |

-continued

```
tcg gaa ttg ggg atg atc ggc gga aat gtc atg cac gtc gag atg tca      1392
Ser Glu Leu Gly Met Ile Gly Gly Asn Val Met His Val Glu Met Ser
    450                 455                 460 ctc gat cag atg atg ttg tgg cga ccg ctt ccc gaa ctg tcc ggc cat      1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat      1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc      1536
Pro Gly Gly Gly Val Ser Gly Ala Ser Gly Arg Ser Ala Ala Arg Ile
        500                 505                 510 gca ctg tcc gac agc cgc cgg ggt aaa gcg agt cag tgg atg cgt cgt      1584
Ala Leu Ser Asp Ser Arg Arg Gly Lys Ala Ser Gln Trp Met Arg Arg
    515                 520                 525 tcg agc cgc tcg tga                                                  1599
Ser Ser Arg Ser
    530
```

<210> SEQ ID NO 34
<211> LENGTH: 532
<212> TYPE: PRT
<213> ORGANISM: artificial sequence
<220> FEATURE:
<223> OTHER INFORMATION: Synthetic Construct

<400> SEQUENCE: 34

```
Met Ser Ala Phe Leu Asp Ala Val Val Gly Ser Gly His Asn Gly
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg
        35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
    130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Ser Gly Ala Leu Ser Ala Ala Leu
225                 230                 235                 240
```

```
Ala Ser Arg Met Ala Val Asp Gly Ala Thr Val Ala Leu Gly Asp Gly
            245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
            275                 280                 285

Leu Thr Thr Leu Asp Leu Leu Gly Asn Gly Gly Phe Asp Arg Thr Thr
            290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
            325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
            355                 360                 365

Pro Arg Pro Ala Val Leu Gly Met Ser Phe Ser Gly Ile Asp Pro Thr
            370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
            405                 410                 415

Glu Ala Asp Arg Ile Val Gly Glu Met Glu Ala Tyr Ala Pro Gly Phe
            420                 425                 430

Thr Asp Ser Val Leu Asp Arg Phe Ile Gln Thr Pro Arg Asp Ile Glu
            435                 440                 445

Ser Glu Leu Gly Met Ile Gly Gly Asn Val Met His Val Glu Met Ser
            450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
            485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Met Arg Arg
            515                 520                 525

Ser Ser Arg Ser
    530

<210> SEQ ID NO 35
<211> LENGTH: 1599
<212> TYPE: DNA
<213> ORGANISM: artificial sequence
<220> FEATURE:
<223> OTHER INFORMATION: 320M4036
<220> FEATURE:
<221> NAME/KEY: CDS
<222> LOCATION: (1)..(1599)

<400> SEQUENCE: 35 atg agt gca ttt ctc gac gcc gtc gtc gtc ggt tcc gga cac aac gcg    48
Met Ser Ala Phe Leu Asp Ala Val Val Val Gly Ser Gly His Asn Ala
1               5                   10                  15 ctc gtt tcg gcc gcg tat ctc gca cgt gag ggt tgg tcg gtc gag gtt    96
Leu Val Ser Ala Ala Tyr Leu Ala Arg Glu Gly Trp Ser Val Glu Val
            20                  25                  30
```

```
ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
     35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
 50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccc gcc cct ggc         288
Arg Tyr Ile Asp Cys Asp Pro Trp Ala Phe Ala Pro Ala Pro Gly
                     85                  90                  95 acc gac ggg ccg ggc atc gtg ttt cat cgc gac ctc gat gca acc tgc     336
Thr Asp Gly Pro Gly Ile Val Phe His Arg Asp Leu Asp Ala Thr Cys
             100                 105                 110 cag tcc atc gaa cga gct tgc ggg aca aag gac gcc gac gcg tac cgg     384
Gln Ser Ile Glu Arg Ala Cys Gly Thr Lys Asp Ala Asp Ala Tyr Arg
         115                 120                 125 cgg ttc gtc gcg gtc tgg tcg gag cgc agc cga cac gtg atg aag gca     432
Arg Phe Val Ala Val Trp Ser Glu Arg Ser Arg His Val Met Lys Ala
     130                 135                 140 ttt tcc aca ccg ccc acc gga tcg aac ctg atc ggt gcg ttc gga gga     480
Phe Ser Thr Pro Pro Thr Gly Ser Asn Leu Ile Gly Ala Phe Gly Gly
145                 150                 155                 160 ctg gcc aca gcg cgc ggc aac agc gaa ctg tcg cgg cag ttc ctc gcg     528
Leu Ala Thr Ala Arg Gly Asn Ser Glu Leu Ser Arg Gln Phe Leu Ala
                 165                 170                 175 ccg ggc gac gcg ctg ctg gac gag tat ttc gac agt gag gca ctc aag     576
Pro Gly Asp Ala Leu Leu Asp Glu Tyr Phe Asp Ser Glu Ala Leu Lys
             180                 185                 190 gca gcg ttg gcg tgg ttc ggc gcc cag tcc ggg cct ccg atg tcg gaa     624
Ala Ala Leu Ala Trp Phe Gly Ala Gln Ser Gly Pro Pro Met Ser Glu
         195                 200                 205 ccg gga acc gct ccg atg gtc ggc ttc gcg gcc ctc atg cac gtc ctg     672
Pro Gly Thr Ala Pro Met Val Gly Phe Ala Ala Leu Met His Val Leu
     210                 215                 220 ccg ccc ggg cga gca gtc gga ggg agc ggc gca ctg agt gct gcg ttg     720
Pro Pro Gly Arg Ala Val Gly Gly Ser Gly Ala Leu Ser Ala Ala Leu
225                 230                 235                 240 gca tcc cgg atg gct gtc gac ggc gcc acc gtc acg ctc ggt gac ggc     768
Ala Ser Arg Met Ala Val Asp Gly Ala Thr Val Thr Leu Gly Asp Gly
                 245                 250                 255 gtg acg tcg atc cgc cgg aac ccg aat cac tgg acc gtc aca acc gag     816
Val Thr Ser Ile Arg Arg Asn Pro Asn His Trp Thr Val Thr Thr Glu
             260                 265                 270 agc ggt cga gaa gtt cac gct cgc aag gta atc gcg ggt tgc cac atc     864
Ser Gly Arg Glu Val His Ala Arg Lys Val Ile Ala Gly Cys His Ile
         275                 280                 285 ctc acg aca ctc gat ctc ctg ggc aac gga ggc ttc gac cga acc acg     912
Leu Thr Thr Leu Asp Leu Leu Gly Asn Gly Gly Phe Asp Arg Thr Thr
     290                 295                 300 ctc gat cac tgg cgg cgg aag atc agg gtc ggc ccc ggc atc ggc gct     960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc    1008
Val Leu Arg Leu Ala Thr Ser Ala Leu Pro Ser Tyr Arg Gly Asp Ala
                 325                 330                 335 acg aca cgg gaa agt acc tcg gga ttg caa tta ctc gtt tcc gat cgc    1056
Thr Thr Arg Glu Ser Thr Ser Gly Leu Gln Leu Leu Val Ser Asp Arg
             340                 345                 350
```

```
gcc cac ttg cgc act gca cac ggc gca gca ctg gca ggg gaa ctg cct      1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg      1152
Pro Arg Pro Ala Val Leu Gly Met Ser Phe Ser Gly Ile Asp Pro Thr
370                 375                 380 atc gcc ccg gcc ggg cgg cat cag gtg aca ctg tgg tcg cag tgg cag      1200
Ile Ala Pro Ala Gly Arg His Gln Val Thr Leu Trp Ser Gln Trp Gln
385                 390                 395                 400 ccg tat cgt ctc agc gga caa cgc gat tgg gcg tcg gtc gcc gag gcc      1248
Pro Tyr Arg Leu Ser Gly Gln Arg Asp Trp Ala Ser Val Ala Glu Ala
                405                 410                 415 gag gcc gac cgg atc gtc ggc gag atg gag gct ttt gca ccc gga ttc      1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag      1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca      1392
Ser Glu Leu Gly Met Ile Gly Gly Asn Val Met His Val Glu Met Ser
450                 455                 460 ctc gat cag atg atg ttg tgg cga ccg ctt ccc gaa ctg tcc ggc cat      1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat      1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc      1536
Pro Gly Gly Gly Val Ser Gly Ala Ser Gly Arg Ser Ala Ala Arg Ile
            500                 505                 510 gca ctg tcc gac agc cgc cgg ggt aaa gcg agt cag tgg atg cgt cgt      1584
Ala Leu Ser Asp Ser Arg Arg Gly Lys Ala Ser Gln Trp Met Arg Arg
        515                 520                 525 tcg agc cgc tcg tga                                                  1599
Ser Ser Arg Ser
    530

<210> SEQ ID NO 36
<211> LENGTH: 532
<212> TYPE: PRT
<213> ORGANISM: artificial sequence
<220> FEATURE:
<223> OTHER INFORMATION: Synthetic Construct

<400> SEQUENCE: 36

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110
```

-continued

```
Gln Ser Ile Glu Arg Ala Cys Gly Thr Lys Asp Ala Asp Ala Tyr Arg
            115                 120                 125

Arg Phe Val Ala Val Trp Ser Glu Arg Ser Arg His Val Met Lys Ala
            130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
            195                 200                 205

Pro Gly Thr Ala Pro Met Val Gly Phe Ala Ala Leu Met His Val Leu
            210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Thr Leu Gly Asp Gly
                245                 250                 255

Val Thr Ser Ile Arg Arg Asn Pro Asn His Trp Thr Val Thr Thr Glu
            260                 265                 270

Ser Gly Arg Glu Val His Ala Arg Lys Val Ile Ala Gly Cys His Ile
            275                 280                 285

Leu Thr Thr Leu Asp Leu Leu Gly Asn Gly Gly Phe Asp Arg Thr Thr
            290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
            355                 360                 365

Pro Arg Pro Ala Val Leu Gly Met Ser Phe Ser Gly Ile Asp Pro Thr
            370                 375                 380

Ile Ala Pro Ala Gly Arg His Gln Val Thr Leu Trp Ser Gln Trp Gln
385                 390                 395                 400

Pro Tyr Arg Leu Ser Gly Gln Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
            435                 440                 445

Ser Glu Leu Gly Met Ile Gly Gly Asn Val Met His Val Glu Met Ser
            450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Met Arg Arg
            515                 520                 525
```

<210> SEQ ID NO 37
<211> LENGTH: 1599
<212> TYPE: DNA
<213> ORGANISM: artificial sequence
<220> FEATURE:
<223> OTHER INFORMATION: 320SHU001
<220> FEATURE:
<221> NAME/KEY: CDS
<222> LOCATION: (1)..(1599)

<400> SEQUENCE: 37

```
atg agc gca ttt ctc gac gcc gtc gtc gtc ggt tcc gga cac aac gca     48
Met Ser Ala Phe Leu Asp Ala Val Val Val Gly Ser Gly His Asn Ala
1               5                   10                  15 ctc gtt tcg gcc gcg tat ctc gcc cgt gag ggt tgg tcg gtc gag gtt     96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga    144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc    192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt    240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc    288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc    336
Thr Asp Gly Pro Gly Ile Val Phe His Arg Asp Leu Asp Ala Thr Cys
            100                 105                 110 cag tcc atc gaa cga gct tgc ggg aca aag gac gcc gac gcg tac cgg    384
Gln Ser Ile Glu Arg Ala Cys Gly Thr Lys Asp Ala Asp Ala Tyr Arg
        115                 120                 125 cgg ttc gtc gcg gtc tgg tcg gag cgc agc cga cac gtg ttg aag gca    432
Arg Phe Val Ala Val Trp Ser Glu Arg Ser Arg His Val Leu Lys Ala
    130                 135                 140 ttt tcc aca ccg ccc acc gga tcg aac ctg atc ggt gcg ttc gga gga    480
Phe Ser Thr Pro Pro Thr Gly Ser Asn Leu Ile Gly Ala Phe Gly Gly
145                 150                 155                 160 ctg gcc aca gtg cgc ggc aac agc gaa ctg tcg cgg cag ttc ctc gcg    528
Leu Ala Thr Val Arg Gly Asn Ser Glu Leu Ser Arg Gln Phe Leu Ala
                165                 170                 175 ccg ggc gac gca ctg ctg gac gag tat ttc gac agt gag gca ctc aag    576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa    624
Ala Ala Leu Ala Trp Phe Gly Ala Gln Ser Gly Pro Pro Met Ser Glu
        195                 200                 205 ccg gga acc gct ccg atg gtc ggc ttc gcg gcc ctc atg cac gtc ctg    672
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg    720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc    768
Ala Ser Arg Met Ala Val Asp Gly Ala Thr Val Ala Leu Gly Asp Gly
                245                 250                 255
```

```
gtg acg tcg atc cgc cgg aac tcg aat cac tgg acc gtc aca acc gag    816
Val Thr Ser Ile Arg Arg Asn Ser Asn His Trp Thr Val Thr Thr Glu
        260                 265                 270 agc ggt cga gaa gtt cac gct cgc aag gta atc gcg ggt tgc cac atc    864
Ser Gly Arg Glu Val His Ala Arg Lys Val Ile Ala Gly Cys His Ile
    275                 280                 285 ctc acg aca ctc gat ctc ctg ggc aac gga ggc ttc gac cga acc aag    912
Leu Thr Thr Leu Asp Leu Leu Gly Asn Gly Gly Phe Asp Arg Thr Lys
        290                 295                 300 ctc gat cac tgg cgg cgg aag atc agg gtc ggc ccc ggc atc ggc gct    960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc    1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc    1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct    1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg    1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag    1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc    1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc    1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag    1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca    1392
Ser Glu Leu Gly Met Ile Gly Gly Asn Val Met His Val Glu Met Ser
    450                 455                 460 ctc gat cag atg atg ttg tgg cga ccg ctt ccc gaa ttg tcc ggc cat    1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat    1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc    1536
Pro Gly Gly Gly Val Ser Gly Ala Ser Gly Arg Ser Ala Ala Arg Ile
            500                 505                 510 gca ctg tcc gac agc cgc tgg ggt aaa gcg agt cag tgg atg cgt cgt    1584
Ala Leu Ser Asp Ser Arg Trp Gly Lys Ala Ser Gln Trp Met Arg Arg
        515                 520                 525 tcg agc cgc tcg tga                                                1599
Ser Ser Arg Ser
        530

<210> SEQ ID NO 38
<211> LENGTH: 532
<212> TYPE: PRT
<213> ORGANISM: artificial sequence
<220> FEATURE:
```

<223> OTHER INFORMATION: Synthetic Construct

<400> SEQUENCE: 38

```
Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
            50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                    85                  90                  95

Thr Asp Gly Pro Gly Ile Val Phe His Arg Asp Leu Asp Ala Thr Cys
                100                 105                 110

Gln Ser Ile Glu Arg Ala Cys Gly Thr Lys Asp Ala Asp Ala Tyr Arg
            115                 120                 125

Arg Phe Val Ala Val Trp Ser Glu Arg Ser Arg His Val Leu Lys Ala
        130                 135                 140

Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
        210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Lys
        290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
        370                 375                 380

Ile Ala Pro Ala Gly Arg His Gln Val Thr Leu Trp Ser Gln Trp Gln
385                 390                 395                 400
```

```
Pro Tyr Arg Leu Ser Gly His Arg Asp Trp Ala Ser Val Ala Glu Ala
            405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
            435                 440                 445

Ser Glu Leu Gly Met Ile Gly Gly Asn Val Met His Val Glu Met Ser
        450                 455                 460

Leu Asp Gln Met Met Leu Trp Arg Pro Leu Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Trp Gly Lys Ala Ser Gln Trp Met Arg Arg
            515                 520                 525

Ser Ser Arg Ser
        530

<210> SEQ ID NO 39
<211> LENGTH: 1599
<212> TYPE: DNA
<213> ORGANISM: artificial sequence
<220> FEATURE:
<223> OTHER INFORMATION: 320SHU004
<220> FEATURE:
<221> NAME/KEY: CDS
<222> LOCATION: (1)..(1599)

<400> SEQUENCE: 39 atg agc gca ttt ctc gac gcc gtc gtc gtc ggt tcc gga cac aac gca      48
Met Ser Ala Phe Leu Asp Ala Val Val Val Gly Ser Gly His Asn Ala
1               5                   10                  15 ctc gtt tcg gcc gcg tat ctc gca cgt gag ggt tgg tcg gtc gag gtt      96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc     288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc     336
Thr Asp Gly Pro Gly Ile Val Phe His Arg Asp Leu Asp Ala Thr Cys
                100                 105                 110 cag tcc atc gaa cga gct tgc ggg aca aag gac gcc gac gcg tac cgg     384
Gln Ser Ile Glu Arg Ala Cys Gly Thr Lys Asp Ala Asp Ala Tyr Arg
            115                 120                 125 cgg ttc gtc gcg gtc tgg tcg gag cgc agc cga cac gtg atg aag gca     432
Arg Phe Val Ala Val Trp Ser Glu Arg Ser Arg His Val Met Lys Ala
        130                 135                 140 ttt tcc aca ccg ccc acc gga tcg aac ctg atc ggt gcg ttc gga gga     480
Phe Ser Thr Pro Pro Thr Gly Ser Asn Leu Ile Gly Ala Phe Gly Gly
145                 150                 155                 160
```

-continued

| | | |
|---|---|---|
| ctg gcc aca gcg cgc ggc aac agc gaa ctg tcg cgg cag ttc ctc gcg<br>Leu Ala Thr Ala Arg Gly Asn Ser Glu Leu Ser Arg Gln Phe Leu Ala<br>165 170 175 | | 528 |
| ccg ggc gac gca ctg ctg gac gag tat ttc gac agt gag gca ctc aag<br>Pro Gly Asp Ala Leu Leu Asp Glu Tyr Phe Asp Ser Glu Ala Leu Lys<br>180 185 190 | | 576 |
| gca gcg ttg gcg tgg ttc ggc gcc cag tcc ggg cct ccg atg tcg gaa<br>Ala Ala Leu Ala Trp Phe Gly Ala Gln Ser Gly Pro Pro Met Ser Glu<br>195 200 205 | | 624 |
| ccg gga acc gct ccg atg gtc ggc ttc gcg gcc ctc atg cac gtc ctg<br>Pro Gly Thr Ala Pro Met Val Gly Phe Ala Ala Leu Met His Val Leu<br>210 215 220 | | 672 |
| ccg ccc ggg cga gca gtc gga ggg agc ggc gca ctg agt gct gcg ttg<br>Pro Pro Gly Arg Ala Val Gly Gly Ser Gly Ala Leu Ser Ala Ala Leu<br>225 230 235 240 | | 720 |
| gca tcc cgg atg gct gtc gac ggc gcc acc gtc gcg ctc ggt gac ggc<br>Ala Ser Arg Met Ala Val Asp Gly Ala Thr Val Ala Leu Gly Asp Gly<br>245 250 255 | | 768 |
| gtg acg tcg atc cgc cgg aac tcg aat cac tgg acc gtc aca acc gag<br>Val Thr Ser Ile Arg Arg Asn Ser Asn His Trp Thr Val Thr Thr Glu<br>260 265 270 | | 816 |
| agc ggt cga gaa gtt cac gct cgc aag gta atc gcg ggt tgc cac atc<br>Ser Gly Arg Glu Val His Ala Arg Lys Val Ile Ala Gly Cys His Ile<br>275 280 285 | | 864 |
| ctc acg aca ctc gat ctc ctg ggc aac gga ggc ttc gac cga acc acg<br>Leu Thr Thr Leu Asp Leu Leu Gly Asn Gly Gly Phe Asp Arg Thr Thr<br>290 295 300 | | 912 |
| ctc gat cac tgg cgg cgg aag atc agg gtc ggc ccc ggc atc ggc gct<br>Leu Asp His Trp Arg Arg Lys Ile Arg Val Gly Pro Gly Ile Gly Ala<br>305 310 315 320 | | 960 |
| gta ttg cga ctg gcg aca tct gcg ctc ccg tct tac cgc ggc gac gcc<br>Val Leu Arg Leu Ala Thr Ser Ala Leu Pro Ser Tyr Arg Gly Asp Ala<br>325 330 335 | | 1008 |
| acg aca cgg gaa agt acc tcg gga ttg caa tta ctc gtt tcc gat cgc<br>Thr Thr Arg Glu Ser Thr Ser Gly Leu Gln Leu Leu Val Ser Asp Arg<br>340 345 350 | | 1056 |
| gcc cac ttg cgc act gca cac ggc gca gca ctg gca ggg gaa ctg cct<br>Ala His Leu Arg Thr Ala His Gly Ala Ala Leu Ala Gly Glu Leu Pro<br>355 360 365 | | 1104 |
| cct cgc cct gcg gtt ctc gga atg agt ttc agc gga atc gat ccc acg<br>Pro Arg Pro Ala Val Leu Gly Met Ser Phe Ser Gly Ile Asp Pro Thr<br>370 375 380 | | 1152 |
| atc gcc ccg gcc ggg cgg cat cag gtg aca ctg tgg tcg cag tgg cag<br>Ile Ala Pro Ala Gly Arg His Gln Val Thr Leu Trp Ser Gln Trp Gln<br>385 390 395 400 | | 1200 |
| ccg tat cgt ctc agc gga cat cgc gat tgg gcg tcg gtc gcc gag gcc<br>Pro Tyr Arg Leu Ser Gly His Arg Asp Trp Ala Ser Val Ala Glu Ala<br>405 410 415 | | 1248 |
| gag gcc gac cgg atc gtc ggc gag atg gag gct ttt gca ccc gga ttc<br>Glu Ala Asp Arg Ile Val Gly Glu Met Glu Ala Phe Ala Pro Gly Phe<br>420 425 430 | | 1296 |
| acc gat tcc gtc ctc gac cgc ttc att caa act ccc cgc gac atc gag<br>Thr Asp Ser Val Leu Asp Arg Phe Ile Gln Thr Pro Arg Asp Ile Glu<br>435 440 445 | | 1344 |
| tcg gaa ttg ggg atg atc ggc gga aat gtc atg cac gtc gag atg tca<br>Ser Glu Leu Gly Met Ile Gly Gly Asn Val Met His Val Glu Met Ser<br>450 455 460 | | 1392 |
| ctc gat cag atg atg ttg tgg cga ccg ctt ccc gaa ctg tcc ggc cat<br>Leu Asp Gln Met Met Leu Trp Arg Pro Leu Pro Glu Leu Ser Gly His | | 1440 |

```
                465                 470                 475                 480
cgc gtt ccg gga gca gac ggg ttg tat ctg acc gga gcc tcg acg cat     1488
Arg Val Pro Gly Ala Asp Gly Leu Tyr Leu Thr Gly Ala Ser Thr His
                    485                 490                 495 ccc ggt ggt ggt gtg tcc gga gcc agt ggt cgc agt gcc gct cga atc     1536
Pro Gly Gly Gly Val Ser Gly Ala Ser Gly Arg Ser Ala Ala Arg Ile
            500                 505                 510 gca ctg tcc gac agc cgc tgg ggt aaa gcg agt cag tgg atg cgt cgt     1584
Ala Leu Ser Asp Ser Arg Trp Gly Lys Ala Ser Gln Trp Met Arg Arg
                515                 520                 525 tcg agc cgc tcg tga                                                 1599
Ser Ser Arg Ser
    530

<210> SEQ ID NO 40
<211> LENGTH: 532
<212> TYPE: PRT
<213> ORGANISM: artificial sequence
<220> FEATURE:
<223> OTHER INFORMATION: Synthetic Construct

<400> SEQUENCE: 40

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
        50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
    130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270
```

```
Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
        290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
                340                 345                 350

Ala His Leu Arg Thr Ala His Gly Ala Ala Leu Ala Gly Glu Leu Pro
                355                 360                 365

Pro Arg Pro Ala Val Leu Gly Met Ser Phe Ser Gly Ile Asp Pro Thr
                370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
                420                 425                 430

Thr Asp Ser Val Leu Asp Arg Phe Ile Gln Thr Pro Arg Asp Ile Glu
                435                 440                 445

Ser Glu Leu Gly Met Ile Gly Gly Asn Val Met His Val Glu Met Ser
        450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
                500                 505                 510

Ala Leu Ser Asp Ser Arg Trp Gly Lys Ala Ser Gln Trp Met Arg Arg
        515                 520                 525

Ser Ser Arg Ser
        530

<210> SEQ ID NO 41
<211> LENGTH: 1599
<212> TYPE: DNA
<213> ORGANISM: artificial sequence
<220> FEATURE:
<223> OTHER INFORMATION: 320SHU008
<220> FEATURE:
<221> NAME/KEY: CDS
<222> LOCATION: (1)..(1599)

<400> SEQUENCE: 41 atg agc gca ttt ctc gac gcc gtc gtc gtc ggt tcc gga cac aac gca      48
Met Ser Ala Phe Leu Asp Ala Val Val Val Gly Ser Gly His Asn Ala
1               5                   10                  15 ctc gtt tcg gcc gcg tat ctc gcc cgt gag ggt tgg tcg gtc gag gtt      96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
        50                  55                  60
```

```
cga cac agt ggc atc atc gag gaa ctc gga ctc ggc gcg cac ggc ctt    240
Arg His Ser Gly Ile Ile Glu Glu Leu Gly Leu Gly Ala His Gly Leu
 65              70                  75                  80 cgc tac atc gac tgt gac ccg tgg gcg ttc gct ccg ccc gcc cct ggc    288
Arg Tyr Ile Asp Cys Asp Pro Trp Ala Phe Ala Pro Pro Ala Pro Gly
                 85                  90                  95 acc gac ggg ccg ggc atc gtg ttt cat cgc gac ctc gat gca acc tgc    336
Thr Asp Gly Pro Gly Ile Val Phe His Arg Asp Leu Asp Ala Thr Cys
            100                 105                 110 cag tcc atc gaa cga gct tgc ggg aca aag gac gcc gac gcg tac cgg    384
Gln Ser Ile Glu Arg Ala Cys Gly Thr Lys Asp Ala Asp Ala Tyr Arg
        115                 120                 125 cgg ttc gtt gcg gtc tgg tcg gag cgc agc cga cac gtg ttg aag gca    432
Arg Phe Val Ala Val Trp Ser Glu Arg Ser Arg His Val Leu Lys Ala
    130                 135                 140 ttt tcc aca ccg ccc acc gga tcg aac ctg atc ggt gcg ttc gga gga    480
Phe Ser Thr Pro Pro Thr Gly Ser Asn Leu Ile Gly Ala Phe Gly Gly
145                 150                 155                 160 ctg gcc aca gtg cgc ggc aac agc gaa ctg tcg cgg cag ttc ctc gcg    528
Leu Ala Thr Val Arg Gly Asn Ser Glu Leu Ser Arg Gln Phe Leu Ala
                165                 170                 175 ccg ggc gac gca ctg ctg gac gag tat ttc gac agt gag gca ctc aag    576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa    624
Ala Ala Leu Ala Trp Phe Gly Ala Gln Ser Gly Pro Pro Met Ser Glu
        195                 200                 205 ccg gga acc gct ccg atg gtc ggc ttc gcc gcc ctc atg cac gtc ctg    672
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg    720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc    768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag    816
Val Thr Ser Ile Arg Arg Asn Ser Asn His Trp Thr Val Thr Thr Glu
            260                 265                 270 agc ggt cga gaa gtt cac gct cgc aag gta gtc gcg ggt tgc cac atc    864
Ser Gly Arg Glu Val His Ala Arg Lys Val Val Ala Gly Cys His Ile
        275                 280                 285 ctc acg aca ctc gat ctc ctg ggc aac gga ggc ttc gac cga acc acg    912
Leu Thr Thr Leu Asp Leu Leu Gly Asn Gly Gly Phe Asp Arg Thr Thr
    290                 295                 300 ctc gat cac tgg cgg cgg aag atc agg gtc ggc ccc ggc atc ggc gct    960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc   1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc   1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct   1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg   1152
Pro Arg Pro Ala Val Leu Gly Met Ser Phe Ser Gly Ile Asp Pro Thr
```

```
                370                 375                 380
atc gcc ccg gcc ggg cgg cat cag gtg aca ctg tgg tcg cag tgg cag       1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc       1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc       1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag       1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca       1392
Ser Glu Leu Gly Met Ile Gly Gly Asn Val Met His Val Glu Met Ser
    450                 455                 460 ctc gat cag atg atg ttg tgg cga ccg ctt ccc gaa ctg tcc ggc cat       1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat       1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc       1536
Pro Gly Gly Gly Val Ser Gly Ala Ser Gly Arg Ser Ala Ala Arg Ile
            500                 505                 510 gca ctg tcc gac agc cgc cgg ggt aaa gcg agt cag tgg atg cgt cgt       1584
Ala Leu Ser Asp Ser Arg Arg Gly Lys Ala Ser Gln Trp Met Arg Arg
        515                 520                 525 tcg agc cgc tcg tga                                                   1599
Ser Ser Arg Ser
    530

<210> SEQ ID NO 42
<211> LENGTH: 532
<212> TYPE: PRT
<213> ORGANISM: artificial sequence
<220> FEATURE:
<223> OTHER INFORMATION: Synthetic Construct

<400> SEQUENCE: 42

Met Ser Ala Phe Leu Asp Ala Val Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
        50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Leu Lys Ala
    130                 135                 140
```

```
Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
            165                 170                 175

Pro Gly Asp Ala Leu Leu Asp Glu Tyr Phe Asp Ser Glu Ala Leu Lys
        180                 185                 190

Ala Ala Leu Ala Trp Phe Gly Ala Gln Ser Gly Pro Pro Met Ser Glu
    195                 200                 205

Pro Gly Thr Ala Pro Met Val Gly Phe Ala Ala Leu Met His Val Leu
210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Val Ala Gly Cys His Ile
        275                 280                 285

Leu Thr Thr Leu Asp Leu Leu Gly Asn Gly Gly Phe Asp Arg Thr Thr
290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
        435                 440                 445

Ser Glu Leu Gly Met Ile Gly Gly Asn Val Met His Val Glu Met Ser
450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Met Arg Arg
        515                 520                 525

Ser Ser Arg Ser
        530

<210> SEQ ID NO 43
<211> LENGTH: 1599
<212> TYPE: DNA
```

<213> ORGANISM: artificial sequence
<220> FEATURE:
<223> OTHER INFORMATION: 320SHU015
<220> FEATURE:
<221> NAME/KEY: CDS
<222> LOCATION: (1)..(1599)

<400> SEQUENCE: 43

```
atg agc gca ttt ctc gac gcc gtc gtc gtc ggt tcc gga cac aac gca       48
Met Ser Ala Phe Leu Asp Ala Val Val Val Gly Ser Gly His Asn Ala
1               5                   10                  15 ctc gtt tcg gcc gcg tat ctc gca cgt gag ggt tgg tcg gtc gag gtt       96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga      144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc      192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt      240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc      288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc      336
Thr Asp Gly Pro Gly Ile Val Phe His Arg Asp Leu Asp Ala Thr Cys
                100                 105                 110 cag tcc atc gaa cga gct tgc ggg aca aag gac gcc gac gcg tac cgg      384
Gln Ser Ile Glu Arg Ala Cys Gly Thr Lys Asp Ala Asp Ala Tyr Arg
            115                 120                 125 cgg ttc gtc gcg gtc tgg tcg gag cgc agc cga cac gtg atg aag gca      432
Arg Phe Val Ala Val Trp Ser Glu Arg Ser Arg His Val Met Lys Ala
        130                 135                 140 ttt tcc aca ccg ccc acc gga ttg aac ctg atc ggt gcg ttc gga gga      480
Phe Ser Thr Pro Pro Thr Gly Leu Asn Leu Ile Gly Ala Phe Gly Gly
145                 150                 155                 160 ctg gcc aca gcg cgc ggc aac agc gaa ctg tcg cgg cag ttc ctc gcg      528
Leu Ala Thr Ala Arg Gly Asn Ser Glu Leu Ser Arg Gln Phe Leu Ala
                165                 170                 175 ccg ggc gac gca ctg ctg gac gag tat ttc gac agt gag gca ctc aag      576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa      624
Ala Ala Leu Ala Trp Phe Gly Ala Gln Ser Gly Pro Pro Met Ser Glu
        195                 200                 205 ccg gga acc gct ccg atg gtc ggc ttc gcg gcc ctc atg cac gtc ctg      672
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg      720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc      768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag      816
Val Thr Ser Ile Arg Arg Asn Ser Asn His Trp Thr Val Thr Thr Glu
            260                 265                 270 agc ggt cga gaa gtt cac gct cgc aag gta atc gcg ggt tgc cac atc      864
Ser Gly Arg Glu Val His Ala Arg Lys Val Ile Ala Gly Cys His Ile
```

|  |  |  |  |  |  |  |  |  |  |  |  |  |  |  |  |
|---|---|---|---|---|---|---|---|---|---|---|---|---|---|---|---|
|  |  | 275 |  |  |  | 280 |  |  |  | 285 |  |  |  |  |  |
| ctc | acg | aca | ctc | gat | ctc | ctg | ggc | aac | gga | ggc | ttc | gac | cga | acc | acg | 912 |
| Leu | Thr | Thr | Leu | Asp | Leu | Leu | Gly | Asn | Gly | Gly | Phe | Asp | Arg | Thr | Thr |  |
|  | 290 |  |  |  |  | 295 |  |  |  |  | 300 |  |  |  |  |  |
| ctc | gat | cac | tgg | cgg | cgg | aag | atc | agg | gtc | ggc | ccc | ggc | atc | ggc | gct | 960 |
| Leu | Asp | His | Trp | Arg | Arg | Lys | Ile | Arg | Val | Gly | Pro | Gly | Ile | Gly | Ala |  |
| 305 |  |  |  |  | 310 |  |  |  |  | 315 |  |  |  |  | 320 |  |
| gta | ttg | cga | ctg | gcg | aca | tct | gcg | ctc | ccg | tct | tac | cgc | ggc | gac | gcc | 1008 |
| Val | Leu | Arg | Leu | Ala | Thr | Ser | Ala | Leu | Pro | Ser | Tyr | Arg | Gly | Asp | Ala |  |
|  |  |  |  | 325 |  |  |  |  | 330 |  |  |  |  | 335 |  |  |
| acg | aca | cgg | gaa | agt | acc | tcg | gga | ttg | caa | tta | ctc | gtt | tcc | gat | cgc | 1056 |
| Thr | Thr | Arg | Glu | Ser | Thr | Ser | Gly | Leu | Gln | Leu | Leu | Val | Ser | Asp | Arg |  |
|  |  |  | 340 |  |  |  |  | 345 |  |  |  |  | 350 |  |  |  |
| gcc | cac | ttg | cgc | act | gca | cac | ggc | gca | gca | ctg | gca | ggg | gaa | ctg | cct | 1104 |
| Ala | His | Leu | Arg | Thr | Ala | His | Gly | Ala | Ala | Leu | Ala | Gly | Glu | Leu | Pro |  |
|  |  | 355 |  |  |  |  | 360 |  |  |  |  | 365 |  |  |  |  |
| cct | cgc | cct | gcg | gtt | ctc | gga | atg | agt | ttc | agc | gga | atc | gat | ccc | acg | 1152 |
| Pro | Arg | Pro | Ala | Val | Leu | Gly | Met | Ser | Phe | Ser | Gly | Ile | Asp | Pro | Thr |  |
| 370 |  |  |  |  | 375 |  |  |  |  | 380 |  |  |  |  |  |  |
| atc | gcc | ccg | gcc | ggg | cgg | cat | cag | gtg | aca | ctg | tgg | tcg | cag | tgg | cag | 1200 |
| Ile | Ala | Pro | Ala | Gly | Arg | His | Gln | Val | Thr | Leu | Trp | Ser | Gln | Trp | Gln |  |
| 385 |  |  |  | 390 |  |  |  |  | 395 |  |  |  |  | 400 |  |  |
| ccg | tat | cgt | ctc | agc | gga | cat | cgc | gat | tgg | gcg | tcg | gtc | gcc | gag | gcc | 1248 |
| Pro | Tyr | Arg | Leu | Ser | Gly | His | Arg | Asp | Trp | Ala | Ser | Val | Ala | Glu | Ala |  |
|  |  |  |  | 405 |  |  |  |  | 410 |  |  |  |  | 415 |  |  |
| gag | gcc | gac | cgg | atc | gtc | ggc | gag | atg | gag | gct | ttt | gca | ccc | gga | ttc | 1296 |
| Glu | Ala | Asp | Arg | Ile | Val | Gly | Glu | Met | Glu | Ala | Phe | Ala | Pro | Gly | Phe |  |
|  |  |  | 420 |  |  |  |  | 425 |  |  |  |  | 430 |  |  |  |
| acc | gat | tcc | gtc | ctc | gac | cgc | ttc | att | caa | act | ccc | cgc | gac | atc | gag | 1344 |
| Thr | Asp | Ser | Val | Leu | Asp | Arg | Phe | Ile | Gln | Thr | Pro | Arg | Asp | Ile | Glu |  |
|  |  | 435 |  |  |  |  | 440 |  |  |  |  | 445 |  |  |  |  |
| tcg | gaa | ttg | ggg | atg | atc | ggc | gga | aat | gtc | atg | cac | gtc | gag | atg | tca | 1392 |
| Ser | Glu | Leu | Gly | Met | Ile | Gly | Gly | Asn | Val | Met | His | Val | Glu | Met | Ser |  |
|  | 450 |  |  |  |  | 455 |  |  |  |  | 460 |  |  |  |  |  |
| ctc | gat | cag | atg | atg | ttg | tgg | cga | ccg | ctt | ccc | gaa | ctg | tcc | ggc | cat | 1440 |
| Leu | Asp | Gln | Met | Met | Leu | Trp | Arg | Pro | Leu | Pro | Glu | Leu | Ser | Gly | His |  |
| 465 |  |  |  |  | 470 |  |  |  |  | 475 |  |  |  |  | 480 |  |
| cgc | gtt | ccg | gga | gca | gac | ggg | ttg | tat | ctg | acc | gga | gcc | tcg | acg | cat | 1488 |
| Arg | Val | Pro | Gly | Ala | Asp | Gly | Leu | Tyr | Leu | Thr | Gly | Ala | Ser | Thr | His |  |
|  |  |  |  | 485 |  |  |  |  | 490 |  |  |  |  | 495 |  |  |
| ccc | ggt | ggt | ggt | gtg | tcc | gga | gcc | agt | ggt | cgc | agt | gcc | gct | cga | atc | 1536 |
| Pro | Gly | Gly | Gly | Val | Ser | Gly | Ala | Ser | Gly | Arg | Ser | Ala | Ala | Arg | Ile |  |
|  |  |  | 500 |  |  |  |  | 505 |  |  |  |  | 510 |  |  |  |
| gca | ctg | tcc | gac | agc | cgc | tgg | ggt | aaa | gcg | agt | cag | tgg | atg | cgt | cgt | 1584 |
| Ala | Leu | Ser | Asp | Ser | Arg | Trp | Gly | Lys | Ala | Ser | Gln | Trp | Met | Arg | Arg |  |
|  |  | 515 |  |  |  |  | 520 |  |  |  |  | 525 |  |  |  |  |
| tcg | agc | cgc | tcg | tga |  |  |  |  |  |  |  |  |  |  |  | 1599 |
| Ser | Ser | Arg | Ser |  |  |  |  |  |  |  |  |  |  |  |  |  |
|  | 530 |  |  |  |  |  |  |  |  |  |  |  |  |  |  |  |

<210> SEQ ID NO 44
<211> LENGTH: 532
<212> TYPE: PRT
<213> ORGANISM: artificial sequence
<220> FEATURE:
<223> OTHER INFORMATION: Synthetic Construct

<400> SEQUENCE: 44

| Met | Ser | Ala | Phe | Leu | Asp | Ala | Val | Val | Gly | Ser | Gly | His | Asn | Ala |
|---|---|---|---|---|---|---|---|---|---|---|---|---|---|---|
| 1 |  |  |  | 5 |  |  |  |  | 10 |  |  |  |  | 15 |

Leu Val Ser Ala Ala Tyr Leu Ala Arg Glu Gly Trp Ser Val Glu Val
            20                  25                  30

Leu Glu Lys Asp Thr Val Leu Gly Ala Val Ser Thr Val Glu Arg
            35                  40                  45

Phe Pro Gly Tyr Lys Val Asp Arg Gly Ser Ser Ala His Leu Met Ile
        50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Pro Ala Pro Gly
                    85                  90                  95

Thr Asp Gly Pro Gly Ile Val Phe His Arg Asp Leu Asp Ala Thr Cys
                100                 105                 110

Gln Ser Ile Glu Arg Ala Cys Gly Thr Lys Asp Ala Asp Ala Tyr Arg
            115                 120                 125

Arg Phe Val Ala Val Trp Ser Glu Arg Ser Arg His Val Met Lys Ala
130                 135                 140

Phe Ser Thr Pro Pro Thr Gly Leu Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu

```
                435                 440                 445
Ser Glu Leu Gly Met Ile Gly Gly Asn Val Met His Val Glu Met Ser
    450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Trp Gly Lys Ala Ser Gln Trp Met Arg Arg
        515                 520                 525

Ser Ser Arg Ser
    530

<210> SEQ ID NO 45
<211> LENGTH: 1599
<212> TYPE: DNA
<213> ORGANISM: artificial sequence
<220> FEATURE:
<223> OTHER INFORMATION: 320SHU016
<220> FEATURE:
<221> NAME/KEY: CDS
<222> LOCATION: (1)..(1599)

<400> SEQUENCE: 45 atg agc gca ttt ctc gac gcc gtc gtc gtc ggt tcc gga cac aac gca      48
Met Ser Ala Phe Leu Asp Ala Val Val Val Gly Ser Gly His Asn Ala
 1               5                  10                  15 ctc gtt tcg gcc gcg tat ctc gcc cgt gag ggt tgg tcg gtc gag gtt      96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc     288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc     336
Thr Asp Gly Pro Gly Ile Val Phe His Arg Asp Leu Asp Ala Thr Cys
               100                 105                 110 cag tcc atc gaa cga gct tgc ggg gca aag gac gcc gac gcg tac cgg     384
Gln Ser Ile Glu Arg Ala Cys Gly Ala Lys Asp Ala Asp Ala Tyr Arg
           115                 120                 125 cgg ttc gtc gcg gtc tgg tcg gag cgc agc cga cac gtg ttg aag gca     432
Arg Phe Val Ala Val Trp Ser Glu Arg Ser Arg His Val Leu Lys Ala
       130                 135                 140 ttt tcc aca ccg ccc acc gga tcg aac ctg atc ggt gcg ttc gga gga     480
Phe Ser Thr Pro Pro Thr Gly Ser Asn Leu Ile Gly Ala Phe Gly Gly
145                 150                 155                 160 ctg gcc aca gtg cgc ggc aac agc gaa ctg tcg cgg cag ttc ctc gcg     528
Leu Ala Thr Val Arg Gly Asn Ser Glu Leu Ser Arg Gln Phe Leu Ala
                165                 170                 175 ccg ggc gac gca ctg ctg gac gag tat ttc gac agt gag gca ctc aag     576
Pro Gly Asp Ala Leu Leu Asp Glu Tyr Phe Asp Ser Glu Ala Leu Lys
```

-continued

```
              180                 185                 190
gca gcg ttg gcg tgg ttc ggc gcc cag tcc ggg cct ccg atg tcg gaa        624
Ala Ala Leu Ala Trp Phe Gly Ala Gln Ser Gly Pro Pro Met Ser Glu
        195                 200                 205 ccg gga acc gct ccg atg gtc ggc ttc gcg gcc ctc atg cac gtc ctg        672
Pro Gly Thr Ala Pro Met Val Gly Phe Ala Ala Leu Met His Val Leu
210                 215                 220 ccg ccc ggg cga gca gtc gga ggg agc ggc gca ctg agt gct gcg ttg        720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc        768
Ala Ser Arg Met Ala Val Asp Gly Ala Thr Val Ala Leu Gly Asp Gly
            245                 250                 255 gtg acg tcg atc cgc cgg aac tcg aat cac tgg acc gtc aca acc gag        816
Val Thr Ser Ile Arg Arg Asn Ser Asn His Trp Thr Val Thr Thr Glu
        260                 265                 270 agc ggt cga gaa gtt cac gct cgc aag gta gtc gcg ggt tgc cac atc        864
Ser Gly Arg Glu Val His Ala Arg Lys Val Val Ala Gly Cys His Ile
    275                 280                 285 ctc acg aca ctc gat ctc ctg ggc aac gga ggc ttc gac cga acc acg        912
Leu Thr Thr Leu Asp Leu Leu Gly Asn Gly Gly Phe Asp Arg Thr Thr
290                 295                 300 ctc gat cac tgg cgg cgg aag atc agg gtc ggc ccc ggc atc ggc gct        960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc       1008
Val Leu Arg Leu Ala Thr Ser Ala Leu Pro Ser Tyr Arg Gly Asp Ala
            325                 330                 335 acg aca cgg gaa agt acc tcg gga ttg caa tta ctc gtt tcc gat cgc       1056
Thr Thr Arg Glu Ser Thr Ser Gly Leu Gln Leu Leu Val Ser Asp Arg
        340                 345                 350 gcc cac ttg cgc act gca cac ggc gca gca ctg gca ggg gaa ctg cct       1104
Ala His Leu Arg Thr Ala His Gly Ala Ala Leu Ala Gly Glu Leu Pro
    355                 360                 365 cct cgc cct gcg gtt ctc gga atg agt ttc agc gga atc gat ccc acg       1152
Pro Arg Pro Ala Val Leu Gly Met Ser Phe Ser Gly Ile Asp Pro Thr
370                 375                 380 atc gcc ccg gcc ggg cgg cat cag gtg aca ctg tgg tcg cag tgg cag       1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc       1248
Pro Tyr Arg Leu Ser Gly His Arg Asp Trp Ala Ser Val Ala Glu Ala
            405                 410                 415 gag gcc gac cgg atc gtc ggc gag atg gag gct ttt gca ccc gga ttc       1296
Glu Ala Asp Arg Ile Val Gly Glu Met Glu Ala Phe Ala Pro Gly Phe
        420                 425                 430 acc gat tcc gtc ctc gac cgc ttc att caa act ccc cgc gac atc gag       1344
Thr Asp Ser Val Leu Asp Arg Phe Ile Gln Thr Pro Arg Asp Ile Glu
    435                 440                 445 tcg gaa ttg ggg atg atc ggc gga aat gtc atg cac gtc gag atg tca       1392
Ser Glu Leu Gly Met Ile Gly Gly Asn Val Met His Val Glu Met Ser
450                 455                 460 ctc gat cag atg atg ttg tgg cga ccg ctt ccc gaa ctg tcc ggc cat       1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat       1488
Arg Val Pro Gly Ala Asp Gly Leu Tyr Leu Thr Gly Ala Ser Thr His
            485                 490                 495 ccc ggt ggt ggt gtg tcc gga gcc agt ggt cgc agt gct gct cga atc       1536
```

```
Pro Gly Gly Gly Val Ser Gly Ala Ser Gly Arg Ser Ala Ala Arg Ile
            500                 505                 510 gca ctg tcc gac agc cgc cgg ggt aaa gcg agt ctg tgg atg cgt cgt      1584
Ala Leu Ser Asp Ser Arg Arg Gly Lys Ala Ser Leu Trp Met Arg Arg
            515                 520                 525 tcg agc cgc tcg tga                                                   1599
Ser Ser Arg Ser
530

<210> SEQ ID NO 46
<211> LENGTH: 532
<212> TYPE: PRT
<213> ORGANISM: artificial sequence
<220> FEATURE:
<223> OTHER INFORMATION: Synthetic Construct

<400> SEQUENCE: 46

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Ala Lys Asp Ala Asp Ala Tyr Arg
        115                 120                 125

Arg Phe Val Ala Val Trp Ser Glu Arg Ser Arg His Val Leu Lys Ala
    130                 135                 140

Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Val Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
```

```
                    305                 310                 315                 320
Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
        435                 440                 445

Ser Glu Leu Gly Met Ile Gly Gly Asn Val Met His Val Glu Met Ser
    450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Leu Trp Met Arg Arg
        515                 520                 525

Ser Ser Arg Ser
    530

<210> SEQ ID NO 47
<211> LENGTH: 1599
<212> TYPE: DNA
<213> ORGANISM: artificial sequence
<220> FEATURE:
<223> OTHER INFORMATION: 320SHU017
<220> FEATURE:
<221> NAME/KEY: CDS
<222> LOCATION: (1)..(1599)

<400> SEQUENCE: 47 atg agc gca ttt ctc gac gcc gtc gtc gtc ggt tcc gga cac aac gca      48
Met Ser Ala Phe Leu Asp Ala Val Val Val Gly Ser Gly His Asn Ala
1               5                   10                  15 ctc gtt tcg gcc gcg tat ctc gcc cgt gag ggt tgg tcg gtc gag gtt      96
Leu Val Ser Ala Ala Tyr Leu Ala Arg Glu Gly Trp Ser Val Glu Val
                20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
            35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
        50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc     288
Arg Tyr Ile Asp Cys Asp Pro Trp Ala Phe Ala Pro Pro Ala Pro Gly
```

-continued

```
                  85                  90                  95
acc gac ggg ccg ggc atc gtg ttt cat cgc gac ctc gat gca acc tgc      336
Thr Asp Gly Pro Gly Ile Val Phe His Arg Asp Leu Asp Ala Thr Cys
            100                 105                 110 cag tcc atc gaa cga gct tgc ggg aca aag gac gcc gac gcg tac cgg      384
Gln Ser Ile Glu Arg Ala Cys Gly Thr Lys Asp Ala Asp Ala Tyr Arg
        115                 120                 125 cgg ttc gtc gcg gtc tgg tcg gag cga agc cga cac gtg ttg aag gca      432
Arg Phe Val Ala Val Trp Ser Glu Arg Ser Arg His Val Leu Lys Ala
    130                 135                 140 ttt tcc aca ccg ccc acc gga tcg aac ctg atc ggt gcg ttc gga gga      480
Phe Ser Thr Pro Pro Thr Gly Ser Asn Leu Ile Gly Ala Phe Gly Gly
145                 150                 155                 160 ctg gcc aca gtg cgc ggc aac agc gaa ctg tcg cgg cag ttc ctc gcg      528
Leu Ala Thr Val Arg Gly Asn Ser Glu Leu Ser Arg Gln Phe Leu Ala
                165                 170                 175 ccg ggc gac gca ctg ctg gac gag tat ttc gac agt gag gca ctc aag      576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa      624
Ala Ala Leu Ala Trp Phe Gly Ala Gln Ser Gly Pro Pro Met Ser Glu
        195                 200                 205 ccg gga acc gct ccg atg gtc ggc ttc gcg gcc ctc atg cac gtc ctg      672
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg      720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc      768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag      816
Val Thr Ser Ile Arg Arg Asn Ser Asn His Trp Thr Val Thr Thr Glu
            260                 265                 270 agc ggt cga gaa gtt cac gct cgc aag gta gtc gcg ggt tgc cac atc      864
Ser Gly Arg Glu Val His Ala Arg Lys Val Val Ala Gly Cys His Ile
        275                 280                 285 ctc acg aca ctc gat ctc ctg ggc aac gga ggc ttc gac cga acc aag      912
Leu Thr Thr Leu Asp Leu Leu Gly Asn Gly Gly Phe Asp Arg Thr Lys
    290                 295                 300 ctc gat cac tgg cgg cgg aag atc agg gtc ggc ccc ggc atc ggc gct      960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc     1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc     1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct     1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg     1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag     1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc     1248
Pro Tyr Arg Leu Ser Gly His Arg Asp Trp Ala Ser Val Ala Glu Ala
```

```
Pro Tyr Arg Leu Ser Gly His Arg Asp Trp Ala Ser Val Ala Glu Ala
            405                 410                 415 gag gcc gac cgg atc gtc ggc gag atg gag gct ttt gca ccc gga ttc      1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag      1344
Thr Asp Ser Val Leu Asp Arg Phe Ile Gln Thr Pro Arg Asp Ile Glu
            435                 440                 445 tcg gaa ttg ggg atg atc ggc gga aat gtc atg cac gtc gag atg tca      1392
Ser Glu Leu Gly Met Ile Gly Gly Asn Val Met His Val Glu Met Ser
    450                 455                 460 ctc gat cag atg atg ttg tgg cga ccg ctt ccc gaa ttg tcc ggc cat      1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat      1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc      1536
Pro Gly Gly Gly Val Ser Gly Ala Ser Gly Arg Ser Ala Ala Arg Ile
            500                 505                 510 gca ctg tcc gac agc cgc tgg ggt aaa gcg agt cag tgg atg cgt cgt      1584
Ala Leu Ser Asp Ser Arg Trp Gly Lys Ala Ser Gln Trp Met Arg Arg
            515                 520                 525 tcg agc cgc tcg tga                                                   1599
Ser Ser Arg Ser
    530

<210> SEQ ID NO 48
<211> LENGTH: 532
<212> TYPE: PRT
<213> ORGANISM: artificial sequence
<220> FEATURE:
<223> OTHER INFORMATION: Synthetic Construct

<400> SEQUENCE: 48

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg
        35                  40                  45

Phe Pro Gly Tyr Lys Val Asp Arg Gly Ser Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser His Val Leu Lys Ala
    130                 135                 140

Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
```

-continued

```
            180                 185                 190
Ala Ala Leu Ala Trp Phe Gly Ala Gln Ser Gly Pro Pro Met Ser Glu
        195                 200                 205
Pro Gly Thr Ala Pro Met Val Gly Phe Ala Ala Leu Met His Val Leu
    210                 215                 220
Pro Pro Gly Arg Ala Val Gly Ser Gly Ala Leu Ser Ala Ala Leu
225                 230                 235                 240
Ala Ser Arg Met Ala Val Asp Gly Ala Thr Val Ala Leu Gly Asp Gly
                245                 250                 255
Val Thr Ser Ile Arg Arg Asn Ser Asn His Trp Thr Val Thr Thr Glu
            260                 265                 270
Ser Gly Arg Glu Val His Ala Arg Lys Val Val Ala Gly Cys His Ile
        275                 280                 285
Leu Thr Thr Leu Asp Leu Leu Gly Asn Gly Gly Phe Asp Arg Thr Lys
    290                 295                 300
Leu Asp His Trp Arg Arg Lys Ile Arg Val Gly Pro Gly Ile Gly Ala
305                 310                 315                 320
Val Leu Arg Leu Ala Thr Ser Ala Leu Pro Ser Tyr Arg Gly Asp Ala
                325                 330                 335
Thr Thr Arg Glu Ser Thr Ser Gly Leu Gln Leu Leu Val Ser Asp Arg
            340                 345                 350
Ala His Leu Arg Thr Ala His Gly Ala Ala Leu Ala Gly Glu Leu Pro
        355                 360                 365
Pro Arg Pro Ala Val Leu Gly Met Ser Phe Ser Gly Ile Asp Pro Thr
    370                 375                 380
Ile Ala Pro Ala Gly Arg His Gln Val Thr Leu Trp Ser Gln Trp Gln
385                 390                 395                 400
Pro Tyr Arg Leu Ser Gly His Arg Asp Trp Ala Ser Val Ala Glu Ala
                405                 410                 415
Glu Ala Asp Arg Ile Val Gly Glu Met Glu Ala Phe Ala Pro Gly Phe
            420                 425                 430
Thr Asp Ser Val Leu Asp Arg Phe Ile Gln Thr Pro Arg Asp Ile Glu
        435                 440                 445
Ser Glu Leu Gly Met Ile Gly Gly Asn Val Met His Val Glu Met Ser
    450                 455                 460
Leu Asp Gln Met Met Leu Trp Arg Pro Leu Pro Glu Leu Ser Gly His
465                 470                 475                 480
Arg Val Pro Gly Ala Asp Gly Leu Tyr Leu Thr Gly Ala Ser Thr His
                485                 490                 495
Pro Gly Gly Gly Val Ser Gly Ala Ser Gly Arg Ser Ala Ala Arg Ile
            500                 505                 510
Ala Leu Ser Asp Ser Arg Trp Gly Lys Ala Ser Gln Trp Met Arg Arg
        515                 520                 525
Ser Ser Arg Ser
    530

<210> SEQ ID NO 49
<211> LENGTH: 1599
<212> TYPE: DNA
<213> ORGANISM: artificial sequence
<220> FEATURE:
<223> OTHER INFORMATION: 320SHU019
<220> FEATURE:
<221> NAME/KEY: CDS
<222> LOCATION: (1)..(1599)
```

<400> SEQUENCE: 49

```
atg agc gca ttt ctc gac gcc gtc gtc gtc ggt tcc gga cac aac gca      48
Met Ser Ala Phe Leu Asp Ala Val Val Val Gly Ser Gly His Asn Ala
1               5                   10                  15 ctc gtt tcg gcc gcg tat ctc gcc cgt gag ggt tgg tcg gtc gag gtt      96
Leu Val Ser Ala Ala Tyr Leu Ala Arg Glu Gly Trp Ser Val Glu Val
            20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
        35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc     288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc     336
Thr Asp Gly Pro Gly Ile Val Phe His Arg Asp Leu Asp Ala Thr Cys
            100                 105                 110 cag tcc atc gaa cga gct tgc ggg aca aag gac gcc gac gcg tac cgg     384
Gln Ser Ile Glu Arg Ala Cys Gly Thr Lys Asp Ala Asp Ala Tyr Arg
        115                 120                 125 cgg ttc gtc gcg gtc tgg tcg gag cgc agc cga cac gtg ttg aag gca     432
Arg Phe Val Ala Val Trp Ser Glu Arg Ser Arg His Val Leu Lys Ala
    130                 135                 140 ttt tcc aca ccg ccc acc gga tcg aac ctg atc ggt gcg ttc gga gga     480
Phe Ser Thr Pro Pro Thr Gly Ser Asn Leu Ile Gly Ala Phe Gly Gly
145                 150                 155                 160 cta gcc aca gtg cgc ggc aac agc gaa ctg tcg cgg cag ttc ctc gcg     528
Leu Ala Thr Val Arg Gly Asn Ser Glu Leu Ser Arg Gln Phe Leu Ala
                165                 170                 175 ccg ggc gac gca ctg ctg gac gag tat ttc gac agt gag gca ctc aag     576
Pro Gly Asp Ala Leu Leu Asp Glu Tyr Phe Asp Ser Glu Ala Leu Lys
            180                 185                 190 gca gcg ttg gcg tgg ttc ggc gcc cag tcc ggg cct ccg atg tcg gaa     624
Ala Ala Leu Ala Trp Phe Gly Ala Gln Ser Gly Pro Pro Met Ser Glu
        195                 200                 205 ccg gga acc gct ccg atg gtc ggc ttc gcg gcc ctc atg cac gtc ctg     672
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg     720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc     768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag     816
Val Thr Ser Ile Arg Arg Asn Ser Asn His Trp Thr Val Thr Thr Glu
            260                 265                 270 agc ggt cga gaa gtt cac gct cgc aag gta atc gcg ggt tgc cac atc     864
Ser Gly Arg Glu Val His Ala Arg Lys Val Ile Ala Gly Cys His Ile
        275                 280                 285 ctc acg aca ctc gat ctc ctg ggc aac gga ggc ttc gac cga acc acg     912
Leu Thr Thr Leu Asp Leu Leu Gly Asn Gly Gly Phe Asp Arg Thr Thr
    290                 295                 300 ctc gat cac tgg cgg cgg aag atc agg gtc ggc ccc ggc atc ggc gct     960
```

```
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc    1008
Val Leu Arg Leu Ala Thr Ser Ala Leu Pro Ser Tyr Arg Gly Asp Ala
                325                 330                 335 acg aca cag gaa agt acc tcg gga ttg caa tta ctc gtt tcc gat cgc    1056
Thr Thr Gln Glu Ser Thr Ser Gly Leu Gln Leu Leu Val Ser Asp Arg
            340                 345                 350 gcc cac ttg cgc act gca cac ggc gca gca ctg gca ggg gaa ctg cct    1104
Ala His Leu Arg Thr Ala His Gly Ala Ala Leu Ala Gly Glu Leu Pro
        355                 360                 365 ccc cgc cct gcg gtt ctc gga atg agt ttc agc gga atc gat ccc acg    1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag    1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc    1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc    1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag    1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca    1392
Ser Glu Leu Gly Met Ile Gly Gly Asn Val Met His Val Glu Met Ser
    450                 455                 460 ctc gat cag atg atg ttg tgg cga ccg ctt ccc gaa ctg tcc ggc cat    1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat    1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc    1536
Pro Gly Gly Gly Val Ser Gly Ala Ser Gly Arg Ser Ala Ala Arg Ile
            500                 505                 510 gca ctg tcc gac agc cgc tgg ggt aaa gcg agt cag tgg atg cgt cgt    1584
Ala Leu Ser Asp Ser Arg Trp Gly Lys Ala Ser Gln Trp Met Arg Arg
        515                 520                 525 tcg agc cgc tcg tga                                                 1599
Ser Ser Arg Ser
    530

<210> SEQ ID NO 50
<211> LENGTH: 532
<212> TYPE: PRT
<213> ORGANISM: artificial sequence
<220> FEATURE:
<223> OTHER INFORMATION: Synthetic Construct

<400> SEQUENCE: 50

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
```

```
                50                  55                  60
Arg His Ser Gly Ile Ile Glu Glu Leu Gly Leu Gly Ala His Gly Leu
 65                  70                  75                  80

Arg Tyr Ile Asp Cys Asp Pro Trp Ala Phe Ala Pro Ala Pro Gly
                 85                  90                  95

Thr Asp Gly Pro Gly Ile Val Phe His Arg Asp Leu Asp Ala Thr Cys
                100                 105                 110

Gln Ser Ile Glu Arg Ala Cys Gly Thr Lys Asp Ala Asp Ala Tyr Arg
                115                 120                 125

Arg Phe Val Ala Val Trp Ser Glu Arg Ser Arg His Val Leu Lys Ala
130                 135                 140

Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
                180                 185                 190

Ala Ala Leu Ala Trp Phe Gly Ala Gln Ser Gly Pro Pro Met Ser Glu
                195                 200                 205

Pro Gly Thr Ala Pro Met Val Gly Phe Ala Ala Leu Met His Val Leu
                210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
                260                 265                 270

Ser Gly Arg Glu Val His Ala Arg Lys Val Ile Ala Gly Cys His Ile
                275                 280                 285

Leu Thr Thr Leu Asp Leu Leu Gly Asn Gly Gly Phe Asp Arg Thr Thr
                290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Gln Glu Ser Thr Ser Gly Leu Gln Leu Leu Val Ser Asp Arg
                340                 345                 350

Ala His Leu Arg Thr Ala His Gly Ala Ala Leu Ala Gly Glu Leu Pro
                355                 360                 365

Pro Arg Pro Ala Val Leu Gly Met Ser Phe Ser Gly Ile Asp Pro Thr
                370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
                420                 425                 430

Thr Asp Ser Val Leu Asp Arg Phe Ile Gln Thr Pro Arg Asp Ile Glu
                435                 440                 445

Ser Glu Leu Gly Met Ile Gly Gly Asn Val Met His Val Glu Met Ser
                450                 455                 460

Leu Asp Gln Met Met Leu Trp Arg Pro Leu Pro Glu Leu Ser Gly His
465                 470                 475                 480
```

```
Arg Val Pro Gly Ala Asp Gly Leu Tyr Leu Thr Gly Ala Ser Thr His
                485                 490                 495

Pro Gly Gly Val Ser Gly Ala Ser Gly Arg Ser Ala Ala Arg Ile
            500                 505                 510

Ala Leu Ser Asp Ser Arg Trp Gly Lys Ala Ser Gln Trp Met Arg Arg
        515                 520                 525

Ser Ser Arg Ser
        530

<210> SEQ ID NO 51
<211> LENGTH: 1599
<212> TYPE: DNA
<213> ORGANISM: artificial sequence
<220> FEATURE:
<223> OTHER INFORMATION: 320SHU022
<220> FEATURE:
<221> NAME/KEY: CDS
<222> LOCATION: (1)..(1599)

<400> SEQUENCE: 51
```

| | | | | | | | | | | | | | | | | |
|---|---|---|---|---|---|---|---|---|---|---|---|---|---|---|---|---|
| atg | agc | gca | ttt | ctc | gac | gcc | gtc | gtc | gtc | ggt | tcc | gga | cac | aac | gca | 48 |
| Met | Ser | Ala | Phe | Leu | Asp | Ala | Val | Val | Val | Gly | Ser | Gly | His | Asn | Ala | |
| 1 | | | | 5 | | | | | 10 | | | | | 15 | | |
| ctc | gtt | tcg | gcc | gcg | tat | ctc | gcc | cgt | gag | ggt | tgg | tcg | gtc | gag | gtt | 96 |
| Leu | Val | Ser | Ala | Ala | Tyr | Leu | Ala | Arg | Glu | Gly | Trp | Ser | Val | Glu | Val | |
| | | | | 20 | | | | | 25 | | | | | 30 | | |
| ctc | gag | aag | gac | acg | gtt | ctc | ggc | ggt | gcc | gtc | tcg | acc | gtc | gag | cga | 144 |
| Leu | Glu | Lys | Asp | Thr | Val | Leu | Gly | Gly | Ala | Val | Ser | Thr | Val | Glu | Arg | |
| | | 35 | | | | | 40 | | | | | 45 | | | | |
| ttt | ccc | gga | tac | aag | gtg | gac | cgg | gga | tcg | tct | gcg | cac | ctc | atg | atc | 192 |
| Phe | Pro | Gly | Tyr | Lys | Val | Asp | Arg | Gly | Ser | Ser | Ala | His | Leu | Met | Ile | |
| 50 | | | | | 55 | | | | | 60 | | | | | | |
| cga | cac | agt | ggc | atc | atc | gag | gaa | ctc | gga | ctc | ggc | gcg | cac | ggc | ctt | 240 |
| Arg | His | Ser | Gly | Ile | Ile | Glu | Glu | Leu | Gly | Leu | Gly | Ala | His | Gly | Leu | |
| 65 | | | | | 70 | | | | | 75 | | | | | 80 | |
| cgc | tac | atc | gac | tgt | gac | ccg | tgg | gcg | ttc | gct | ccg | ccc | gcc | cct | ggc | 288 |
| Arg | Tyr | Ile | Asp | Cys | Asp | Pro | Trp | Ala | Phe | Ala | Pro | Pro | Ala | Pro | Gly | |
| | | | | 85 | | | | | 90 | | | | | 95 | | |
| acc | gac | ggg | ccg | ggc | atc | gtg | ttt | cat | cgc | gac | ctc | gat | gca | acc | tgc | 336 |
| Thr | Asp | Gly | Pro | Gly | Ile | Val | Phe | His | Arg | Asp | Leu | Asp | Ala | Thr | Cys | |
| | | | 100 | | | | | 105 | | | | | 110 | | | |
| cag | tcc | atc | gaa | cga | gct | tgc | ggg | aca | aag | gac | gcc | gac | gcg | tac | cgg | 384 |
| Gln | Ser | Ile | Glu | Arg | Ala | Cys | Gly | Thr | Lys | Asp | Ala | Asp | Ala | Tyr | Arg | |
| | | 115 | | | | | 120 | | | | | 125 | | | | |
| cgg | ttc | gtc | gcg | gtc | tgg | tcg | gag | cgc | agc | cga | cac | gtg | ttg | aag | gca | 432 |
| Arg | Phe | Val | Ala | Val | Trp | Ser | Glu | Arg | Ser | Arg | His | Val | Leu | Lys | Ala | |
| | 130 | | | | | 135 | | | | | 140 | | | | | |
| ttt | tcc | aca | ccg | ccc | acc | gga | tcg | aac | ctg | atc | ggt | gcg | ttc | gga | gga | 480 |
| Phe | Ser | Thr | Pro | Pro | Thr | Gly | Ser | Asn | Leu | Ile | Gly | Ala | Phe | Gly | Gly | |
| 145 | | | | | 150 | | | | | 155 | | | | | 160 | |
| ctg | gcc | aca | gtg | cgc | ggc | aac | agc | gaa | ctg | tcg | cgg | cag | ttc | ctc | gcg | 528 |
| Leu | Ala | Thr | Val | Arg | Gly | Asn | Ser | Glu | Leu | Ser | Arg | Gln | Phe | Leu | Ala | |
| | | | | 165 | | | | | 170 | | | | | 175 | | |
| ccg | ggc | gac | gca | ctg | ctg | gac | gag | tat | ttc | gac | agt | gag | gca | ctc | aag | 576 |
| Pro | Gly | Asp | Ala | Leu | Leu | Asp | Glu | Tyr | Phe | Asp | Ser | Glu | Ala | Leu | Lys | |
| | | | 180 | | | | | 185 | | | | | 190 | | | |
| gca | gcg | ttg | gcg | tgg | ttc | ggc | gcc | cag | tcc | ggg | cct | ccg | atg | tcg | gaa | 624 |
| Ala | Ala | Leu | Ala | Trp | Phe | Gly | Ala | Gln | Ser | Gly | Pro | Pro | Met | Ser | Glu | |
| | | 195 | | | | | 200 | | | | | 205 | | | | |
| ccg | gga | acc | gct | ccg | atg | gtc | ggc | ttc | gcg | gcc | ctc | atg | cac | gtc | ctg | 672 |

```
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg        720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc        768
Ala Ser Arg Met Ala Val Asp Gly Ala Thr Val Ala Leu Gly Asp Gly
                245                 250                 255 gtg acg tcg atc cgc cgg aac tcg aat cac tgg acc gtc aca acc gag        816
Val Thr Ser Ile Arg Arg Asn Ser Asn His Trp Thr Val Thr Thr Glu
            260                 265                 270 agc ggt cga gaa gtt cac gct cgc aag gta gtc gcg ggt tgc cac atc        864
Ser Gly Arg Glu Val His Ala Arg Lys Val Val Ala Gly Cys His Ile
        275                 280                 285 ctc acg aca ctc gat ctc ctg ggc aac gga ggc ttc gac cga acc acg        912
Leu Thr Thr Leu Asp Leu Leu Gly Asn Gly Gly Phe Asp Arg Thr Thr
    290                 295                 300 ctc gat cac tgg cgg cgg aag atc agg gtc ggc ccc ggc atc ggc gct        960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc       1008
Val Leu Arg Leu Ala Thr Ser Ala Leu Pro Ser Tyr Arg Gly Asp Ala
                325                 330                 335 acg aca cgg gaa agt acc tcg gga ttg caa tta ctc gtt tcc gat cgc       1056
Thr Thr Arg Glu Ser Thr Ser Gly Leu Gln Leu Leu Val Ser Asp Arg
            340                 345                 350 gcc cac ttg cgc act gca cac ggc gca gca ctg gca ggg gaa ctg cct       1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg       1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag       1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc       1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc       1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag       1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca       1392
Ser Glu Leu Gly Met Ile Gly Gly Asn Val Met His Val Glu Met Ser
    450                 455                 460 ctc gat cag atg atg ttg tgg cga ccg ctt ccc gaa ctg tcc ggc cat       1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat       1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc       1536
Pro Gly Gly Gly Val Ser Gly Ala Ser Gly Arg Ser Ala Ala Arg Ile
            500                 505                 510 gca ctg tcc gac agc cgc cgg ggt aaa gcg agt cgg tgg atg cgt cgt       1584
Ala Leu Ser Asp Ser Arg Arg Gly Lys Ala Ser Arg Trp Met Arg Arg
        515                 520                 525
```

```
tcg agc cgc tcg tga                                              1599
Ser Ser Arg Ser
    530
```

<210> SEQ ID NO 52
<211> LENGTH: 532
<212> TYPE: PRT
<213> ORGANISM: artificial sequence
<220> FEATURE:
<223> OTHER INFORMATION: Synthetic Construct

<400> SEQUENCE: 52

```
Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Ala Val Ser Thr Val Glu Arg
                35                  40                  45

Phe Pro Gly Tyr Lys Val Asp Arg Gly Ser Ala His Leu Met Ile
    50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
                100                 105                 110

Gln Ser Ile Glu Arg Ala Cys Gly Thr Lys Asp Ala Asp Ala Tyr Arg
                115                 120                 125

Arg Phe Val Ala Val Trp Ser Glu Arg Ser Arg His Val Leu Lys Ala
    130                 135                 140

Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Val Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350
```

-continued

```
Ala His Leu Arg Thr Ala His Gly Ala Ala Leu Ala Gly Glu Leu Pro
        355                 360                 365
Pro Arg Pro Ala Val Leu Gly Met Ser Phe Ser Gly Ile Asp Pro Thr
    370                 375                 380
Ile Ala Pro Ala Gly Arg His Gln Val Thr Leu Trp Ser Gln Trp Gln
385                 390                 395                 400
Pro Tyr Arg Leu Ser Gly His Arg Asp Trp Ala Ser Val Ala Glu Ala
                405                 410                 415
Glu Ala Asp Arg Ile Val Gly Glu Met Glu Ala Phe Ala Pro Gly Phe
            420                 425                 430
Thr Asp Ser Val Leu Asp Arg Phe Ile Gln Thr Pro Arg Asp Ile Glu
        435                 440                 445
Ser Glu Leu Gly Met Ile Gly Gly Asn Val Met His Val Glu Met Ser
    450                 455                 460
Leu Asp Gln Met Met Leu Trp Arg Pro Leu Pro Glu Leu Ser Gly His
465                 470                 475                 480
Arg Val Pro Gly Ala Asp Gly Leu Tyr Leu Thr Gly Ala Ser Thr His
                485                 490                 495
Pro Gly Gly Gly Val Ser Gly Ala Ser Gly Arg Ser Ala Ala Arg Ile
            500                 505                 510
Ala Leu Ser Asp Ser Arg Arg Gly Lys Ala Ser Arg Trp Met Arg Arg
        515                 520                 525
Ser Ser Arg Ser
    530
```

CAROTENOID KETOLASE GENES WITH IMPROVED KETOCAROTENOID YIELD

This application claims the benefit of U.S. Provisional Application No. 60/577,970, filed Jun. 8, 2004.

FIELD OF THE INVENTION

This invention is in the field of microbiology and molecular biology. More specifically, nucleic acid molecules encoding CrtO carotenoid ketolases characterized by improved ketocarotenoid production are provided. Methods for microbial production of ketocarotenoid compounds using the present CrtO ketolases are also provided.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish and birds. Colors of carotenoid range from yellow to red with variations of brown and purple. As precursors of vitamin A, carotenoids are fundamental components in our diet and they play additional important role in human health. Industrial uses of carotenoids include pharmaceuticals, food supplements, animal feed additives and colorants in cosmetics to mention a few.

Because animals are unable to synthesize carotenoids de novo, they must obtain them by dietary means. Thus, manipulation of carotenoid production and composition in plants or bacteria can provide new or improved source for carotenoids.

Carotenoids come in many different forms and chemical structures. Most naturally occurring carotenoids are hydrophobic tetraterpenoids containing a $C_{40}$ methyl-branched hydrocarbon backbone derived from successive condensation of eight $C_5$ isoprene units (IPP). In addition, rare carotenoids with longer or shorter backbones occur in some species of nonphotosynthetic bacteria. The term "carotenoid" actually include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids are furthermore described as being acyclic, monocyclic, or bicyclic depending on whether the ends of the hydrocarbon backbones have been cyclized to yield aliphatic or cyclic ring structures (G. Armstrong, (1999) In *Comprehensive Natural Products Chemistry*, Elsevier Press, volume 2, pp 321-352).

Carotenoid biosynthesis starts with the isoprenoid pathway and the generation of a C5 isoprene unit, isopentenyl pyrophosphate (IPP). IPP is condensed with its isomer dimethylallyl pyrophophate (DMAPP) to form the C10, geranyl pyrophosphate (GPP), and elongated to the C15, farnesyl pyrophosphate (FPP). FPP synthesis is common to both carotenogenic and non-carotenogenic bacteria. Enzymes in subsequent carotenoid pathways generate carotenoid pigments from the FPP precursor and can be divided into two categories: carotene backbone synthesis enzymes and subsequent modification enzymes. The backbone synthesis enzymes include geranyl geranyl pyrophosphate synthase, phytoene synthase, phytoene dehydrogenase and lycopene cyclase, etc. The modification enzymes include ketolases, hydroxylases, dehydratases, glycosylases, etc.

Carotenoid ketolases are enzymes that introduce keto groups to the β-ionone ring of the cyclic carotenoids, such as β-carotene and zeaxanthin, to produce ketocarotenoids. Examples of ketocarotenoids include astaxanthin, canthaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-ketotorulene, deoxyflexixanthin, and myxobactone. Unlike genes in the upstream isoprenoid pathway that are common in many organisms, the downstream carotenoid modifying enzymes are less common.

Several classes of carotenoid ketolase have been reported (Hannibal et al., *J. Bacteriol.* 182: 3850-3853 (2000)). These include CrtW ketolases from *Agrobacterium aurantiacum* (Misawa et al., *J. Bacteriol.* 177(22): 6575-6584 (1995); WO 99/07867), *Bradyrhizobium* sp. ORS278 (Hannibal et al., supra), *Brevundimonas aurantiaca* (De Souza et al., WO 02/79395), *Paracoccus marcusii* (Yao et al., CN1380415); Bkt ketolases from *Haematococcus pluvialis* (Sun et al., *Proc. Natl. Acad. Sci. USA,* 95(19): 11482-11488 (1998); Linde, H. and Sandmann, G., EP1173579; Breitenbach et al., *FEMS Microbiol. Lett.,* 404(2-3): 241-246 (1996)); and CrtO ketolases from *Synechocystis* sp. (Lagarde et al., *Appl. Environ. Microbiol.,* 66(1): 64-72 (2000); Masamoto et al., *Plant Cell Physiol.,* 39(5): 560-564 (2000); FR 2792335; Cheng et al., U.S. Ser. No. 10/209,372, hereby incorporated by reference)), *Rhodococcus erythropolis* (Cheng et al., supra), *Deinococcus radiodurans* (Cheng et al., supra), and *Gloeobacter violaceus* (Nakamura et al., *DNA Res.,* 10: 181-201 (2003)). It should be noted that the CrtO ketolase reported in *Haematococcus pluvialis* (Harker, M. and Hirschberg, J., *FEBS Lett.,* 404(2-3): 129-134 (1997); U.S. Pat. No. 5,965,795; U.S. Pat. No. 5,916,791; and U.S. Pat. No. 6,218,599) appears to be a CrtW/Bkt ketolasd based on its size and homology to other CrtW/Bkt ketolases. Sequence comparison between the Bkt ketolase from *Haematococcus pluvialis* to publicly available sequences mostly closely matched to other CrtW ketolases. Bkt ketolases appear to be closely related to CrtW ketolases, sharing very little structural similarity to the CrtO ketolases (Cheng, et al, supra). For example, reported CrtW/Bkt ketolases are generally encoded by nucleic acid fragments about 800-1000 bp in length while CrtO ketolases are normally encoded by a nucleic acid fragments of about 1.6 kb in size. Cheng et al. defines CrtO ketolases based on the presence of six conserved motifs considered diagnostic for all CrtO ketolases. The reported CrtO ketolases from *Rhodococcus erythropolis, Deinococcus radiodurans,* and *Synechocystis* sp. PCC6803 are comprised of these diagnostic motifs (U.S. Ser. No. 10/209,372).

The CrtO ketolases reported by Cheng et al. generally exhibit much lower activity when producing ketocarotenoids (i.e. canthaxanthin) from β-carotene in comparison to the reported CrtW ketolases (see Tables 2 and 3 in U.S. Ser. No. 10/209,372). In vitro experiments using recombinantly expressed *R. erythropolis* AN12 CrtO ketolase showed that after 20 hours only 30% of the initial β-carotene substrate was converted into canthaxanthin (35% of the initial β-carotene was converted to echinenone with the remaining 35% remaining as β-carotene).

There is a need for CrtO carotenoid ketolases having improved activity for ketocarotenoid production. Improvements in ketocarotenoid production will enable use of CrtO ketolases for industrial production of commercially useful ketocarotenoids, such as canthaxanthin and astaxanthin. Additionally, commercially useful CrtO ketolases can be recombinantly coexpressed with one or more structurally unrelated CrtW/Bkt ketolases to increase carotenoid titer.

Coexpressing divergent ketocarotenoids should improve ketocarotenoid titer without adding instability to the host expression system.

The problem to be solved therefore is to provide nucleic acid molecules encoding CrtO ketolases useful for ketocarotenoid production.

SUMMARY OF THE INVENTION

Applicants have solved the stated problem by creating several mutant CrtO ketolases exhibiting improved ketocarotenoid production in comparison to the wild type CrtO from Rhodococcus erythropolis AN12. The CrtO ketolase from R. erythropolis AN12 was protein engineered using a combination of error-prone PCR and gene shuffling techniques to create a series of ketolases with significantly improved activity.

In one aspect, the invention provides an isolated nucleic acid molecule encoding a mutant carotenoid ketolase having the amino acid sequence, as set forth in SEQ ID NO:2 and comprising at least selected from the group consisting of:
   a) a replacement of threonine at amino acid position 121 with alanine;
   b) a replacement of methionine at amino acid position 142 with leucine;
   c) a replacement of alanine at amino acid position 164 with valine;
   d) a replacement of isoleucine at amino acid position 283 with valine;
   e) a replacement of threonine at amino acid position 304 with lysine;
   f) a replacement of arginine at amino acid position 339 with glutamine;
   g) a replacement of arginine at amino acid position 519 with tryptophan; and
   h) a replacement of glutamine at amino acid position 524 with leucine or arginine.

In another embodiment the invention provides an isolated nucleic acid molecule encoding a carotenoid ketolase enzyme having an amino acid sequence selected from the group consisting SEQ ID NO: 14, 16, 18, 20, 22, 24, 26, 28, 30, 32, 34, 36, 38, 40, 42, 44, 46, 48, 50, and 52. Additionally the invention provides polypeptides encoded by the isolated nucleic acid molecules of the invention and genetic chimera and host cells comprising the same.

In another embodiment the invention provides a method for the production of cyclic ketocarotenoid compounds comprising:
   a) providing a host cell which produces monocyclic or bicyclic carotenoids;
   b) transforming the host cell with the isolated nucleic acid molecule of the invention encoding a carotenoid ketolase enzyme;
   c) growing the transformed host cell of (b) under conditions whereby a cyclic ketocarotenoid is produced; and
   d) optionally isolating the ketocarotenoid produced in step c).

In another embodiment the invention provides a method of altering cyclic ketocarotenoid biosynthesis in an organism comprising,
   (a) introducing into a host cell the isolated nucleic acid molecule of the invention encoding a carotenoid ketolase; and
   (b) growing the host cell of (a) under conditions whereby the carotenoid ketolase gene is expressed and cyclic ketocarotenoid biosynthesis is altered.

BRIEF DESCRIPTION OF THE FIGURES AND SEQUENCE DESCRIPTIONS

Figure 1:
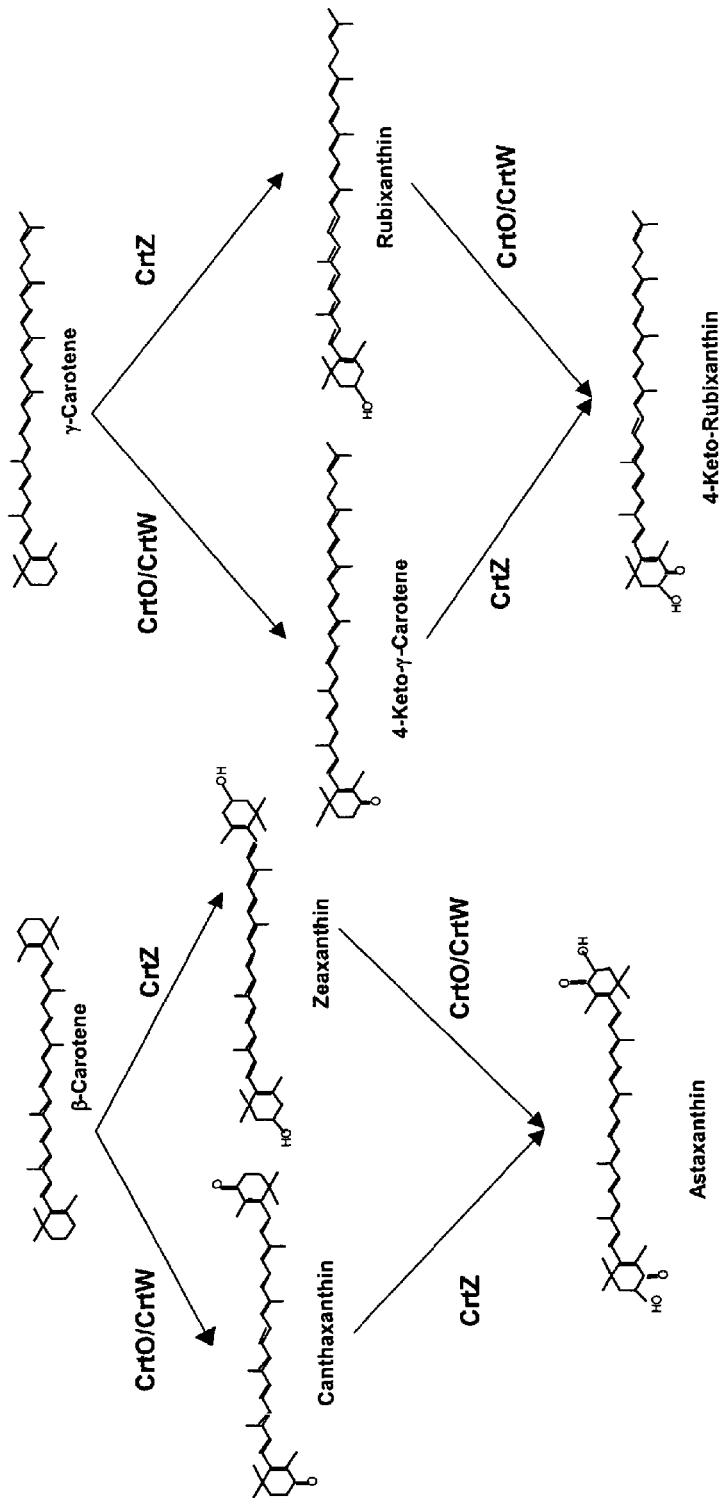
FIG. 1 illustrates common carotenoid products produced by a ketolase in conjunction with an hydroxylase enzyme.

The invention can be more fully understood from the following detailed description, biological deposits, and the accompanying sequence descriptions, which form a part of this application.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the wild type crtO ketolase coding sequence from Rhodococcus erythropolis AN12. SEQ ID NO:2 is deduced amino acid sequence of the wild type crtO ketolase from Rhodococcus erythropolis AN12.

SEQ ID NO: 3 is the nucleotide sequence encoding the codon optimized crtO319 gene in pDCQ319.

SEQ ID NO: 4 is the nucleotide sequence encoding the codon optimized crtO303 gene in pDCQ303.

SEQ ID NO: 5 is the deduced amino acid sequence of the polypeptide encoded by the crtO303 gene.

SEQ ID NO: 6 is the nucleotide sequence encoding the codon optimized crtO320 gene in pDCQ320.

SEQ ID NO: 7 is the nucleotide sequence of primer crtO-For.

SEQ ID NO: 8 is the nucleotide sequence of primer crtO-Rev.

SEQ ID NO: 9 is the nucleotide sequence of primer crtO900-For.

SEQ ID NO: 10 is the nucleotide sequence of primer crtO303-Rev.

SEQ ID NO: 11 is the nucleotide sequence of primer 320-F1.

SEQ ID NO: 12 is the nucleotide sequence of primer 320-R1.

SEQ ID NO: 13 is the nucleotide sequence of 319M3022.

SEQ ID NO: 14 is the deduced amino acid sequence of 319M3022.

SEQ ID NO: 15 is the nucleotide sequence of 303M3044.

SEQ ID NO: 16 is the deduced amino acid sequence of 303M3044.

SEQ ID NO: 17 is the nucleotide sequence of 320M4006.

SEQ ID NO: 18 is the deduced amino acid sequence of 320M4006.

SEQ ID NO: 19 is the nucleotide sequence of 320M4007.

SEQ ID NO: 20 is the deduced amino acid sequence of 320M4007.

SEQ ID NO: 21 is the nucleotide sequence of 320M4009.

SEQ ID NO: 22 is the deduced amino acid sequence of 320M4009.

SEQ ID NO: 23 is the nucleotide sequence of 320M4018.

SEQ ID NO: 24 is the deduced amino acid sequence of 320M4018.

SEQ ID NO: 25 is the nucleotide sequence of 320M4019.
SEQ ID NO: 26 is the deduced amino acid sequence of 320M4019.
SEQ ID NO: 27 is the nucleotide sequence of 320M4020.
SEQ ID NO: 28 is the deduced amino acid sequence of 320M4020.
SEQ ID NO: 29 is the nucleotide sequence of 320M4023.
SEQ ID NO: 30 is the deduced amino acid sequence of 320M4023 SEQ ID NO: 31 is the nucleotide sequence of 320M4027.
SEQ ID NO: 32 is the deduced amino acid sequence of 320M4027.
SEQ ID NO: 33 is the nucleotide sequence of 320M4032.
SEQ ID NO: 34 is the deduced amino acid sequence of 320M4032.
SEQ ID NO: 35 is the nucleotide sequence of 320M4036.
SEQ ID NO: 36 is the deduced amino acid sequence of 320M4036.
SEQ ID NO: 37 is the nucleotide sequence of 320SHU001.
SEQ ID NO: 38 is the deduced amino acid sequence of 320SHU001.
SEQ ID NO: 39 is the nucleotide sequence of 320SHU004.
SEQ ID NO: 40 is the deduced amino acid sequence of 320SHU004.
SEQ ID NO: 41 is the nucleotide sequence of 320SHU008.
SEQ ID NO: 42 is the deduced amino acid sequence of 320SHU008.
SEQ ID NO: 43 is the nucleotide sequence of 320SHU015.
SEQ ID NO: 44 is the deduced amino acid sequence of 320SHU015.
SEQ ID NO: 45 is the nucleotide sequence of 320SHU016.
SEQ ID NO: 46 is the deduced amino acid sequence of 320SHU016.
SEQ ID NO: 47 is the nucleotide sequence of 320SHU017.
SEQ ID NO: 48 is the deduced amino acid sequence of 320SHU017.
SEQ ID NO: 49 is the nucleotide sequence of 320SHU019.
SEQ ID NO: 50 is the deduced amino acid sequence of 320SHU019.
SEQ ID NO: 51 is the nucleotide sequence of 320SHU022.
SEQ ID NO: 52 is the deduced amino acid sequence of 320SHU022.

BRIEF DESCRIPTION OF BIOLOGICAL DEPOSITS

The following biological deposits have been made under the terms of the Budapest Treaty on the International Recognition of the Deposit of Microorganisms for the purposes of patent Procedure:

| Depositor Identification Reference | Int'l. Depository Designation | Date of Deposit |
|---|---|---|
| Methylomonas 16a | ATCC# PTA-2402 | Aug. 22, 2000 |
| WS#208 E. coli strain $P_{T5}$-dxs $P_{T5}$-idi $P_{T5}$-ygbBP $P_{T5}$-ispB, pDCQ108 | ATCC# PTA-4823 | Nov. 26, 2002 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The invention relates to engineered CrtO ketolases with improved catalytic efficiency (i.e. improved ketocarotenoid production) for use in commercial ketocarotenoid production. All of the ketolases were characterized as having an improved ability to produce ketocarotenoids when compared to a corresponding codon optimized version of the wild-type enzyme from which they were created.

The present mutant crtO genes and their expression products, CrtO carotenoid ketolases, are useful for the creation of recombinant organisms having the ability to produce ketocarotenoid compounds. Additionally, the present CrtO ketolases can be coexpressed with well-known CrtW ketolases since they share no structural similarity, creating stable recombinant organisms capable of increased ketocarotenoid production.

The present crtO ketolase genes described herein enable the production of ketocarotenoids in a recombinant host cell. Incorporation and expression of these genes in an industrially-suitable production host enables cost effective production of ketocarotenoids. The ketocarotenoid produced can be used for a variety of applications including, but not limited to, dietary supplements, fish and poultry pigmentation, and electro-optic applications. For example, salmon and shrimp aquacultures are particularly useful applications for this invention as carotenoid pigmentation is critically important for the value of these organisms (Shahidi, F. and Brown, J. A., Crit. Rev Food Sci 38(1): 1-67 (1998)). Additionally, the ketocarotenoid astaxanthin is a powerful antioxidant and has been reported to boost immune functions and reduce carcinogenesis in humans (Jyonouchi et al., Nutr. Cancer 23: 171-183 (1995); Tanaka et al., Cancer Res. 55: 4059-4064 (1995)).

In this disclosure, a number of terms and abbreviations are used. The following definitions are provided.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, the term "isoprenoid" or "terpenoid" refers to the compounds are any molecule derived from the isoprenoid pathway including 10 carbon terpenoids and their derivatives, such as carotenoids and xanthophylls.

As used herein, the terms "Rhodococcus erythropolis AN12", "Rhodococcus erythropolis strain AN12" or "AN12" will be used interchangeably and refer to the Rhodococcus erythropolis AN12 strain (U.S. Ser. No. 10/209,372).

As used herein, the term "carotenoid" refers to a compound composed of a polyene backbone which is condensed from five-carbon isoprene unit. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids that are particularly suitable in the present invention are monocyclic and bicyclic carotenoids.

As used herein, the term "carotenoid ketolase" or "ketolase" or "cyclic carotenoid ketolase" refers to an enzyme that can add keto groups to the ionone ring of either monocyclic or bicyclic carotenoids. Two distinct classes of carotenoid ketolase have been reported. The first class is CrtW/Bkt ketolases that typically exhibit homology to one another and are generally encoded by a nucleotide sequence of approximately 800-1000 bp in length. The second class of ketolase, and the object of the present application, are CrtO ketolases. These ketolases are normally encoded by nucleotide sequence of approximately 1.6 kb in length and exhibit no structural similarity to the CrtW/Bkt ketolases. A phylogentic analysis illustrating the differences between CrtO and CrtW ketolases is provided in FIG. 2 (WO 10/209,372).

As used herein, the term "motif" refers to short conserved amino acid sequences found in a group of protein sequences. Motifs frequently form a recognition sequence or are highly conserved parts of domains. Motif may also refer to all localized homology regions, independent of their size. A motif descriptor could be used to describe the short sequence motifs, consisting of amino acid characters and other characters represent ambiguities and length insertions. CrtO ketolases are known to possess six diagnostic conserved motifs (U.S. Ser. No. 10/209,372) not found in CrW/Bkt ketolases.

As used herein, the terms "diagnostic conserved motifs", "conserved amino acid motifs", and "diagnostic motif" refers to amino acid sequences that are common among CrtO ketolase enzymes and the presence of which is diagnostic for cyclic carotenoid ketolase functionality.

As used herein, the term "keto group" or "ketone group" will be used interchangeably and refers to a group in which a carbonyl group is bonded to two carbon atoms: $R_2C=O$ (neither R may be H).

As used herein the term "β-ionone ring" or "β-ionone group" is defined as $C_9H_{15}$.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp, *CABIOS* 5: 151-153 (1989)) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

"Codon degeneracy" refers to the nature in the genetic code permitting variation of the nucleotide sequence without affecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs: 14, 16, 18, 20, 22, 24, 26, 28, 30, 32, 34, 36, 38, 40, 42, 44, 46, 48, 50, and 52. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available. In the present application, the coding sequence of several genes was either partially or completely codon optimized to match the codon usage found in a *Methylomonas* sp. 16a (Table 1).

As used herein, the term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a nonnative organism, or chimeric genes. A "transgene" is a gene that has been introduced into the genome by a transformation procedure.

"Coding sequence" refers to a DNA sequence that codes for a specific amino acid sequence. As used herein, the term "suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal (normally limited to eurkaryotes) is usually characterized by affecting the addition of polyadenylic acid tracts to the 3' end of the mRNA precursor.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic", "recombinant" or "transformed" organisms.

As used herein, the term "recombination" will refer to a process whereby genetic combinations are formed which were not present in parental template molecules, by the processes of crossing over or independent assortment. Thus, recombination includes all combinations of genetic sequences that can be obtained from the parental template molecules (whereby each nucleotide position of the newly generated "recombinogenic product(s)" can be derived from any of the parental templates at that particular nucleotide position); and additionally, recombination includes the introduction of new mutations (i.e. deletions, substitutions, or insertions).

As used herein, the term "recombined polypeptide" means a polypeptide encoded by recombined genes or DNA. Recombined polypeptides will often have altered or enhanced properties. The term "Entner-Douderoff pathway" refers to a series of biochemical reactions for conversion of hexoses such as glucose or fructose to the important 3-carbon cellular intermediates pyruvate and glyceraldehyde 3-phosphate without any net production of biochemically useful energy. The key enzymes unique to the Entner-Douderoff pathway are the 6-phosphogluconate dehydratase and a ketodeoxyphospho-gluconate aldolase.

The term "Embden-Meyerhof pathway" refers to the series of biochemical reactions for conversion of hexoses such as glucose and fructose to important cellular 3-carbon intermediates such as glyceraldehyde 3 phosphate, dihydroxyacetone phosphate, phosphoenol pyruvate and pyruvate. These reactions typically proceed with net yield of biochemically useful energy in the form of ATP. The key enzymes unique to the Embden-Meyerhof pathway are the phosphofructokinase and fructose 1,6 bisphosphate aldolase.

As used herein, the term "carbon substrate" refers to a carbon source capable of being metabolized by host organisms of the present invention and particularly carbon sources selected from the group consisting of monosaccharides, disaccharides, polysaccharides, and single carbon substrates ($C_1$ carbon substrates) or mixtures thereof.

The term "$C_1$ carbon substrate" or "single carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide. In one aspect, the $C_1$ carbon substrate is methane and/or methanol.

The term "$C_1$ metabolizer" refers to a microorganism that has the ability to use a single carbon substrate as its sole source of energy and biomass. $C_1$ metabolizers will typically be methylotrophs and/or methanotrophs.

The term "methylotroph" means an organism capable of oxidizing organic compounds that do not contain carbon-carbon bonds. Where the methylotroph is able to oxidize $CH_4$, the methylotroph is also a methanotroph. In one aspect, the methylotroph is a methylotrophic bacteria. In another aspect, the methylotrophic bacteria grown on methane and/or methanol.

The term "methanotroph" or "methanotrophic bacteria" means a methylotrophic bacteria capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas, Methylobacter, Methylococcus*, and *Methylosinus*. In one aspect, the methanotroph is grown on methane and/or methanol.

As used herein, the term "high growth methanotrophic bacterial strain" refers to a bacterium capable of growth with methane or methanol as the sole carbon and energy source and which possesses a functional Embden-Meyerof carbon flux pathway resulting in a high rate of growth and yield of cell mass per gram of $C_1$ substrate metabolized. The specific "high growth methanotrophic bacterial strain" described herein is referred to as "*Methylomonas* 16a", "16a" or "*Methylomonas* sp. 16a", which terms are used interchangeably and which refer to the *Methylomonas* sp. 16a (ATCC PTA-2402) strain (U.S. Pat. No. 6,689,601; hereby incorporated by reference).

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein, the term "altered biological activity" or "altered activity" will refer to an activity associated with a protein encoded by a microbial nucleotide sequence which can be measured by an assay method, where that activity is either greater than or less than the activity associated with the native microbial sequence. As used herein, "enhanced biological activity" refers to an altered activity that is greater than that associated with the native sequence. As used herein, "diminished biological activity" refers to an altered activity that is less than that associated with the native sequence. In the present application, protein engineered CrtO ketolases are provided which have improved ketolase activity when compared to a codon optimized version of the wild type gene from which they were developed (endogenous crtO gene from Rhodococcus erythropolis AN12; U.S. Ser. No. 10/209,372). Increases in ketolase activity were measured by the amount of β-carotene converted into canthaxanthin (reported as percentage yield) under similar reaction conditions. The expression system used to evaluate each mutant and the corresponding control was essentially identical. The recombinant protein expression level of each mutant CrtO ketolase was essentially identical. Improvements in the percentage yield of ketocarotenoid production were therefore attributed to structural differences associated with each of the present CrtO ketolases. The structural differences are represented by the nucleotide and amino acid sequences provided for each of the present CrtO ketolases.

As used herein, the terms "recombinogenic extension method using unpaired primers" and "the unpaired primers method" are used interchangeably to refer to the method disclosed in WO 03/072743 (corresponding to U.S. Ser. No. 10/374,366; hereby incorporated by reference) wherein recombinogenic products are created from template molecules using a method based on unpaired primers.

As used herein, the term "paired primers" will refer to a pair of primers, consisting of a forward and reverse primer, which are designed to anneal to a single template molecule and permit synthesis of an exact copy of that template by a primer directed nucleic acid amplification process. In the case of a double-stranded template molecule, the forward and reverse primers enable the synthesis of an exact copy of the double-stranded template since the forward primer produces an exact copy of the antisense strand (that is, a complementary copy of the sense strand which it is using as a template) and the reverse primer produces an exact copy of the sense strand (that is, a complementary copy of the antisense strand which it is using as a template). In contrast, when the template molecule is single-stranded, an exact copy of that template is produced using a primer directed nucleic acid amplification process.

As used herein, the term "unpaired primers" will refer to a pair of primers, consisting of a forward and a reverse primer, which are not designed to anneal to a single template molecule and permit synthesis of an exact copy of that template by a primer directed nucleic acid amplification process. Instead, the forward primer will anneal to a first template molecule, but will not be able to anneal to a second template molecule. The reverse primer will anneal to a second template molecule that is different in sequence from the first template molecule, and yet will not be able to anneal to the first template molecule. This unique design of unpaired primers ensures that a single-or double-stranded template molecule can not be amplified by a primer directed nucleic acid amplification process, unless recombination occurs during replication via template switching.

As used herein, the term "template(s)" or "parent template(s)" refers to a nucleic acid molecule that is copied by a DNA or RNA polymerase according to the rules of Watson-Crick base pairing to produce a new strand of DNA or RNA. The sequence information in the template (or "model") is preserved, since the first copy produced from that template molecule has a complementary sequence. Template molecules may be single or double-stranded and derived from any source.

The "5' region" and "3' region" of a nucleic acid will be used as relative terms, in reference to the region of nucleotides wherein it is desirable for recombination to occur. These regions may be within a template molecule or within a flanking DNA sequence that is attached to the template molecules. Unpaired primers will anneal to a portion of these 5' and 3' regions.

As used herein, the term "flanking sequence" or "flanking DNA fragment" will refer to a short segment of DNA that is attached to either the 5' or 3' region of a template molecule, in order to provide a unique nucleotide sequence (with respect to the template molecule) to which an unpaired primer may anneal.

As used herein, a "full length extension product" is a nucleotide sequence produced by primer-directed replication that has a length very similar (within about 100 bases) to that contained between the 5' and 3' region of the parent templates.

As used herein, the term "amplification" is used to describe the process in which replication is repeated in cyclic manner such that the number of copies of the "template nucleic acid" is increased in either a linear or logarithmic fashion.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403-410 (1990)); 3.) DNASTAR (DNASTAR, Inc. Madison, Wis.); 4.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.); and 5.) the Vector NTI version 7.0 programs (Informax, Inc., Bethesda, Md.). Within the context of this application it will be understood that where sequence analysis software is used for analysis, that the results of the analysis will be based on the "default values" of the program referenced, unless otherwise specified. As used herein "default values" will mean any set of values or parameters (set by the manufacturer) which originally load with the software when first initialized.

Standard recombinant DNA and molecular cloning techniques used here are well known in the art and are described by Sambrook, J., Fritsch, E. F. and Maniatis, T., *Molecular*

*Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

As used herein, the term "improved ketolase activity" or "significantly improved ketolase activity" refers to the present crtO genes encoding mutant CrtO ketolases having improved ketolase activity when compared to the ketolase activity of the *Rhodococcus erythropolis* AN12 wild type CrtO ketolase (SEQ ID NO: 2). Improvements in ketolase activity were determined by measuring the percentage yield of canthaxanthin produced in recombinant hosts previously engineered to produce excess amounts of the ketolase substrate, β-carotene, when grown under similar conditions.

In one embodiment, mutant CrtO ketolases of the present invention are those having an increase in the percentage yield of canthaxanthin of at least a 5% when compared to the percentage yield of canthaxanthin from a codon optimized version (crtO320; SEQ ID NO: 6) of the *Rhodococcus erythropolis* AN12 crtO gene encoding the wild type CrtO amino acid sequence (SEQ ID NO: 2) grown under similar reaction conditions. As used herein, "similar reaction conditions" will be used to described reactions conditions that are essentially identical when assaying ketocarotenoid yield. In another embodiment, mutant CrtO ketolases of the present invention are those having at least a 10% increase in the percentage yield of canthaxanin. In yet another embodiment, preferred ketolases are those having at least a 25% increase in the percentage yield of canthaxanthin. Most preferred ketolases are those exhibiting at least a 50% increase in the percentage yield of canthaxanthin. Comparisons in ketolase activity can be conducted under a variety of reaction conditions depending upon the selected host organism. Suitable comparisons are those conducted between the engineered ketolase of interest and a suitable control under similar reaction conditions. Recombinant expression levels of the present ketolases were essentially identical, indicating that improvement in canthaxanthin yield were attributed to structural modifications resulting increased ketolase activity.

The present CrtO ketolases may be used in vitro or in vivo in for the production of ketocarotenoids from carotenoid compounds having at least one β-ionone ring.

Recombinant Expression—Microbial

The genes and gene products of the instant sequences may be produced in heterologous host cells, particularly in the cells of microbial hosts. Expression in recombinant microbial hosts may be useful for the expression of various pathway intermediates, for the modulation of pathways already existing in the host, or for the synthesis of new products heretofore not possible using the host.

Preferred heterologous host cells for expression of the present genes are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to bacterial, fungal or yeast species such as *Aspergillus, Trichoderma, Saccharomyces, Pichia, Phaffia, Candida, Hansenula*, or bacterial species such as *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferred bacterial species include *Escherichia coli, Methylomonas* sp. 16a, and derivatives thereof.

Microbial expression systems and expression vectors containing regulatory sequences that direct high-level expression of foreign proteins are well known to those skilled in the art. Any of these can be used to construct chimeric genes for expression of present ketolases. These chimeric genes could then be introduced into appropriate microorganisms via transformation to provide high-level expression of the present ketolases.

Accordingly, it is expected that introduction of chimeric genes encoding the instant bacterial enzymes under the control of the appropriate promoters will demonstrate increased or altered ketocarotenoid production. It is contemplated that it will be useful to express the instant genes both in natural host cells as well as heterologous hosts. Introduction of the present mutant crtO genes into native host will result in altered levels of existing carotenoid production. Additionally, the instant genes may also be introduced into non-native host bacteria where the existing carotenoid pathway may be manipulated.

Specific ketocarotenoids that will be produced by the present invention include but are not limited to, canthaxanthin, astaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone. Of particular interest is the production of canthaxanthin, astaxanthin, 4-keto-γ-carotene, and 4-keto-rubixanthin (FIG. 1). The specific substrate for the present CrtO enzyme is a carotenoid having at least one β-ionone ring. Cyclic carotenoids are well known in the art and available commercially. Preferred substrates in the present invention are cyclic carotenoids that include, but are not limited to, β-carotene, γ-carotene, zeaxanthin, rubixanthin, echinenone, and torulene. In the present examples, an *E. coli* strain (WS210) containing chromosomal modifications for enhanced carotenoid production previously engineered to produce elevated levels of β-carotene (up to 6000 ppm) was used to monitor ketolase activity (*E. coli* strain WS210 contains the same chromosomal modifications as *E. coli* strain WS208; ATCC PTA-4823; U.S. Ser. No. 10/735,442; hereby incorporated by reference). WS210 is identical to WS208 except for the fact that WS208 is comprised of plasmid (pDCQ108) expressing the β-carotene synthesis genes (crtEXYIB) from *Pantoea stewartii* (ATCC No. 8199).

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the instant ORF's in the desired host cell are numerous and familiar to those skilled in the art. Virtually any promoter capable of driving these genes is suitable for the present invention including, but not limited to: CYC1, HIS3, GAL1, GAL10, ADH1, PGK, PHO5, GAPDH, ADC1, TRP1, URA3, LEU2, ENO, TPI (e.g., useful for expression in *Saccharomyces*); AOX1 (e.g., useful for expression in *Pichia*); and lac, ara, tet, trp, $IP_L$, $IP_R$, T7, tac, and trc (e.g., useful for expression in *Escherichia coli*) as well as the amy, apr, npr promoters and various phage promoters useful for expression in, e.g., *Bacillus*. Additionally, the deoxy-xylulose phosphate synthase or methanol dehydrogenase operon promoter (Springer et al., *FEMS Microbiol Lett* 160: 119-124 (1998)), the promoter for polyhydroxyalkanoic acid synthesis (Foellner et al., *Appl. Microbiol. Biotechnol.* 40: 284-291 (1993)), promoters identified from native plasmids in methylotrophs (EP 296484), Plac (Toyama et al., *Microbiology* 143: 595-602 (1997); EP 62971), Ptrc (Brosius et al., *Gene* 27: 161-172 (1984)), promoters identified from methanotrophs (PCT/US03/33698), and promoters associated with antibiotic resistance [e.g., kanamycin (Springer et al., supra; Ueda et al., *Appl. Environ. Microbiol.* 57: 924-926 (1991)) or tetracycline (U.S. Pat. No. 4,824,786)] are suitable for expression in $C_1$ metabolizers.

It may be necessary to include an artificial ribosomal binding site ("RBS") upstream of a gene to be expressed, when the RBS is not provided by the vector. This is frequently required for the second, third, etc. gene(s) of an operon to be expressed, when a single promoter is driving the expression of a first, second, third, etc. group of genes. Methodology to determine the preferred sequence of a RBS in a particular host organism will be familiar to one of skill in the art, as are means for creation of this synthetic site.

Termination control regions may also be derived from various genes native to the preferred hosts. Optionally, a termination site may be unnecessary; however, it is most preferred if included.

Merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: 1.) the nature of the relevant transcriptional promoter and terminator sequences; 2.) the strength of the ribosome binding site; 3.) the number of copies of the cloned gene and whether the gene is plasmid-borne or integrated into the genome of the host cell; 4.) the final cellular location of the synthesized foreign protein; 5.) the efficiency of translation in the host organism; 6.) the intrinsic stability of the cloned gene protein within the host cell; and 7.) the codon usage within the cloned gene, such that its frequency approaches the frequency of preferred codon usage of the host cell. Each of these types of modifications are encompassed in the present invention, as means to further optimize expression of the present mutant CrtO ketolases.

Finally, to promote accumulation of ketocarotenoids, it may be necessary to reduce or eliminate the expression of certain genes in the target pathway or in competing pathways that may serve as sinks for energy or carbon. Alternatively, it may be useful to over-express various genes upstream of desired carotenoid intermediates to enhance production. Methods of manipulating genetic pathways for the purposes described above are common and well known in the art.

For example, once a key genetic pathway has been identified and sequenced, specific genes may be up-regulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (U.S. Pat. No. 5,565,350; Zarling et al., PCT/US93/03868).

In another aspect, where the sequence of the gene to be disrupted is known, one of the most effective methods for gene down-regulation is targeted gene disruption, where foreign DNA is inserted into a structural gene so as to disrupt transcription. This can be affected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.* 171: 4617-4622 (1989); Balbas et al., *Gene* 136: 211-213 (1993); Gueldener et al., *Nucleic Acids Res.* 24: 2519-2524 (1996); and Smith et al., *Methods Mol. Cell. Biol.* 5: 270-277 (1996)).

Antisense technology is another method of down-regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA encoding the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed., (1989) Sinauer Associates: Sunderland, M A; or Deshpande, Mukund V., *Appl. Biochem. Biotechnol.* 36: 227-234 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see, for example: The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wis., based upon the Tn5 bacterial transposable element).

Within the context of the present invention, it may be useful to modulate the expression of the carotenoid biosynthetic pathway by any one of the methods described above. For example, a number of genes encoding enzymes in the carotenoid pathway (crtE, crtX, crtY, crtI, crtB, crtZ, crtN, crtM, crtN1, crtN2, ald, sqs, etc.) are known, leading to the production of carotenoid. Thus, it may also be useful to up-regulate the initial condensation of 3-carbon compounds (pyruvate and D-glyceraldehyde 3-phosphate) to increase the yield of the 5-carbon compound D-1-deoxyxylulose-5-phosphate (mediated by the dxs gene). This would increase the flux of carbon entering the carotenoid biosynthetic pathway and permit increased production of ketocarotenoids. Alternatively (or in addition to), it may be desirable to knockout the crtM/crtN genes leading to the synthesis of $C_{30}$ carotenoids, if the microbial host is capable of synthesizing these types of compounds. For example, an optimized *Methylomonas* sp. 16a strain has been created containing a knockout of the native $C_{30}$ pathway, creating a non-pigmented strain suitable for engineering $C_{40}$ carotenoid production (U.S. Ser. No. 10/997,844; hereby incorporated by reference). Or, in systems having native functional crtE, crtX, crtY, crtI, crtB, and crtZ genes, the accumulation of β-carotene or zeaxanthin may be effected by the disruption of down-stream genes (e.g., crtZ or crtX) by any one of the methods described above.

Figure 2:
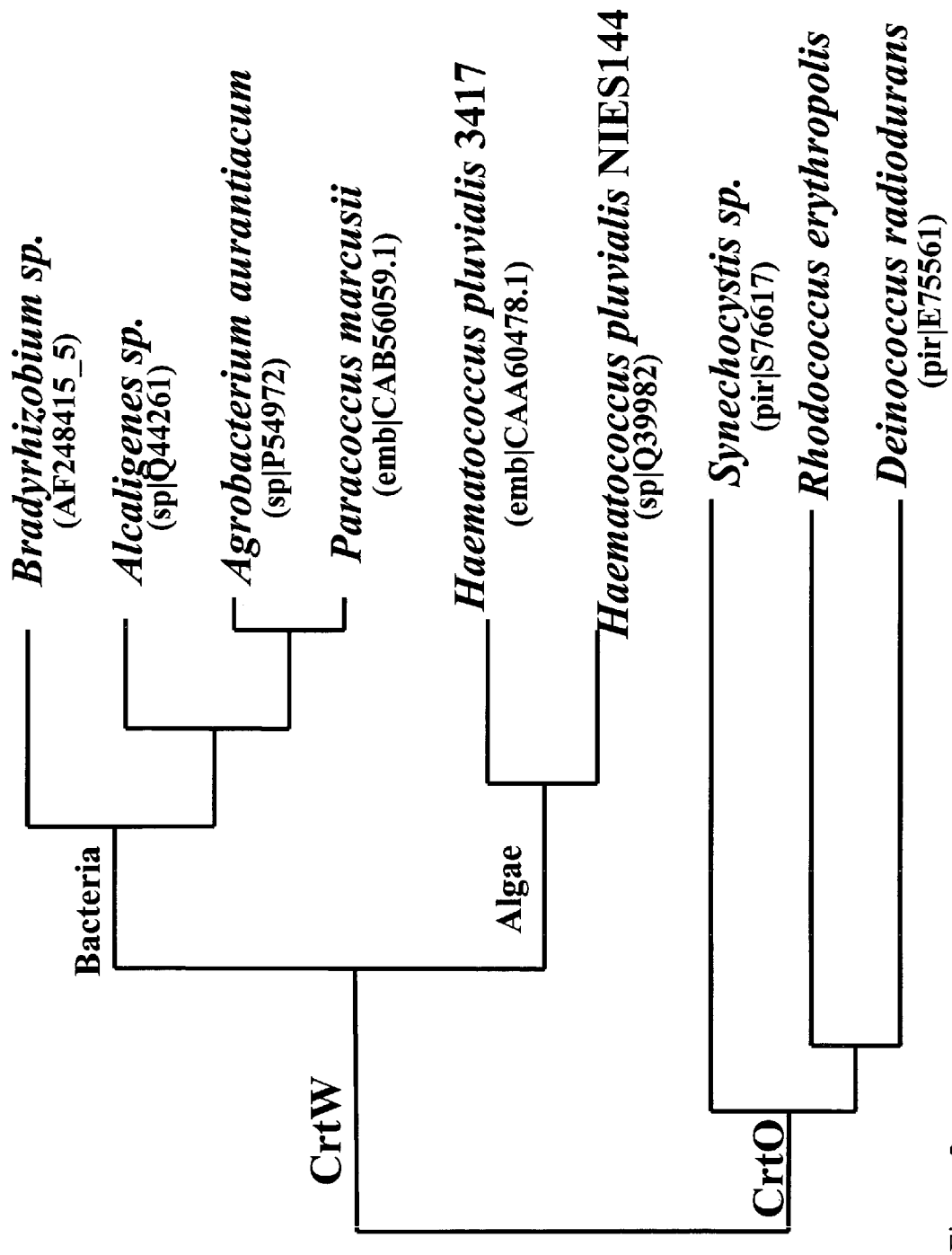
FIG. 2 illustrates the phylogenetic relationship of the carotenoid ketolases.

In another embodiment, the present CrtO ketolases can be coexpressed with one or more structurally unrelated CrtW/Bkt ketolases for increased production of ketocarotenoids. As used herein, "structurally unrelated" refers to differences in the gene's nucleic acid sequence. The absence of highly homologous regions between crtW/bkt and crtO ketolase genes permits stable expression as the probably of homologous recombination decreases. Cheng et al. (10/209,372) have previously shown that CrtW/Bkt ketolases are structurally unrelated CrtO ketolases based on a phylogenetic analysis (FIG. 2). Preferred structurally unrelated CrtW/Bkt ketolases useful for coexpression have less than 60% nucleic acid sequence identity based on BLASTN analysis when compared to the coding sequence of the present ketolases. More preferred structurally unrelated CrtW/Bkt ketolases share less than 50% identity with the present CrtO ketolases. Most preferred structurally unrelated CrtW/Bkt ketolases share less than 40% identify with the present CrtO ketolases.

Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Industrial Production using Recombinant Microorganisms

Where commercial production of ketocarotenoid compounds is desired using the present crtO genes, a variety of culture methodologies may be applied. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system with the exception that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch culturing methods are common and well known in the art and examples may be found in Brock (supra) or Deshpande (supra).

Commercial production of cyclic ketocarotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass.

Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane or methanol for which metabolic conversion into key biochemical intermediates has been demonstrated. In one aspect, the host cell is a methylotrophic microorganism grown on methane and/or methanol. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1-Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153: 485-489 (1990)). Hence it is contemplated that the source of carbon utilized in the present invention may encompass a wide variety of carbon containing substrates and will only be limited by the choice of organism.

Methylotrophs and *Methylomonas* sp. 16a as Microbial Hosts

Although a number of carotenoids have been produced from recombinant microbial sources [e.g., *E. coli* and *Candida utilis* for production of lycopene (Farmer, W. R. and Liao, J. C., *Biotechnol. Prog.* 17: 57-61 (2001); Wang et al., *Biotechnol Prog.* 16: 922-926 (2000); Misawa, N. and Shimada, H., *J. Biotechnol.* 59: 169-181 (1998); Shimada et al., *Appl. Environm. Microbiol.* 64: 2676-2680 (1998)]; *E. coli*, *Candida utilis* and *Pfaffia rhodozyma* for production of β-carotene (Albrecht et al., *Biotechnol. Lett.* 21: 791-795 (1999); Miura et al., *Appl. Environm. Microbiol.* 64: 1226-1229 (1998); U.S. Pat. No. 5,691,190); *E. coli* and *Candida utilis* for production of zeaxanthin (Albrecht et al., supra; Miura et al., supra; *E. Coli* and *Phaffia rhodozyma* for production of astaxanthin (U.S. Pat. No. 5,466,599; U.S. Pat. No. 6,015,684; U.S. Pat. No. 5,182,208; U.S. Pat. No. 5,972,642); see also: U.S. Pat. No. 5,656,472, U.S. Pat. No. 5,545,816, U.S. Pat. No. 5,530,189, U.S. Pat. No. 5,530,188, U.S. Pat. No. 5,429,939, and U.S. Pat. No. 6,124,113), these methods of producing carotenoids using various combinations of different crt genes suffer from low yields and reliance on relatively expensive feedstocks. Thus, it is desirable to use a method that produces higher yields of carotenoids in a microbial host from an inexpensive feedstock.

There are a number of microorganisms that utilize single carbon substrates as their sole energy source. Such microorganisms are referred to herein as "C1 metabolizers". These organisms are characterized by the ability to use carbon substrates lacking carbon to carbon bonds as a sole source of energy and biomass. These carbon substrates include, but are not limited to: methane, methanol, formate, formaldehyde, formic acid, methylated amines (e.g., mono-, di- and trimethyl amine), methylated thiols, carbon dioxide, and various other reduced carbon compounds which lack any carbon-carbon bonds.

All C1 metabolizing microorganisms are generally classified as methylotrophs. Methylotrophs may be defined as any organism capable of oxidizing organic compounds that do not contain carbon-carbon bonds. However, facultative methylotrophs, obligate methylotrophs, and obligate methanotrophs are all various subsets of methylotrophs. Specifically:

Facultative methylotrophs have the ability to oxidize organic compounds which do not contain carbon-carbon bonds, but may also use other carbon substrates such as sugars and complex carbohydrates for energy and biomass. Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1 Compounds.*, [Int. Symp.], $7^{th}$ (1993), pp 285-302. Murrell, J. Collin and Don P. Kelly, eds. Intercept: Andover, UK; Madigan et al., *Brock Biology of Microorganisms*, $8^{th}$ ed., Prentice Hall: Upper Saddle River, N.J. (1997)).

Obligate methylotrophs are those organisms that are limited to the use of organic compounds that do not contain carbon-carbon bonds for the generation of energy.

Obligate methanotrophs are those obligate methylotrophs that have the distinct ability to oxidize methane.

Additionally, the ability to utilize single carbon substrates is not limited to bacteria but extends also to yeasts and fungi. A number of yeast genera are able to use single carbon substrates as energy sources in addition to more complex materials (i.e., the methylotrophic yeasts).

Although a large number of these methylotrophic organisms are known, few of these microbes have been successfully harnessed in industrial processes for the synthesis of materials. And, although single carbon substrates are cost-effective energy sources, difficulty in genetic manipulation of these microorganisms as well as a dearth of information about their genetic machinery has limited their use primarily to the synthesis of native products.

Despite these hardships, many methanotrophs contain an inherent isoprenoid pathway which enables these organisms to synthesize pigments and provides the potential for one to envision engineering these microorganisms for production of other non-endogenous isoprenoid compounds. Since methanotrophs can use single carbon substrates (i.e., methane and/or methanol) as an energy source, it could be possible to produce carotenoids at low cost in these organisms. Examples wherein a methanotroph was engineered for production of β-carotene are described in U.S. Ser. No. 09/941,947 and U.S. Ser. No. 10/997,844; each hereby incorporated by reference.

In the present invention, methods are provided for the expression of genes involved in the biosynthesis of carotenoid compounds in microorganisms that are able to use single carbon substrates as a sole energy source. The host microorganism may be any C1 metabolizer that has the ability to synthesize farnesyl pyrophosphate (FPP) as a metabolic precursor for carotenoids. More specifically, facultative methylotrophic bacteria suitable in the present invention include, but are not limited to: *Methylophilus, Methylobacillus, Methylobacterium, Hyphomicrobium, Xanthobacter, Bacillus, Paracoccus, Nocardia, Arthrobacter, Rhodopseudomonas,* and *Pseudomonas*. Specific methylotrophic yeasts useful in the present invention include, but are not limited to: *Candida, Hansenula, Pichia, Torulopsis,* and *Rhodotorula*. And, exemplary methanotrophs are included in, but are not limited to, the genera *Methylomonas, Methylobacter, Methylococcus, Methylosinus, Methylocyctis, Methylomicrobium,* and *Methanomonas*.

Of particular interest in the present invention are high growth obligate methanotrophs having an energetically favorable carbon flux pathway. For example, a specific strain of methanotroph has been reported having several pathway features that makes it particularly useful for carbon flux manipulation. This strain is known as *Methylomonas* sp. 16a (ATCC PTA 2402) (U.S. Pat. No. 6,689,601); and, this particular strain and other related methylotrophs are preferred microbial hosts for expression of the gene products of this invention, useful for the production of $C_{40}$ carotenoids.

*Methylomonas* sp. 16a naturally produces $C_{30}$ carotenoids. Odom et al. have reported that expression of $C_{40}$ carotenoid genes in *Methylomonas* 16a produced a mixture of $C_{30}$ and $C_{40}$ carotenoids (U.S. Ser. No. 09/941,947). Several of the genes involved in $C_{30}$ carotenoid production in this strain have been identified including (but not limited to) the crtN1, ald, crtN2, and crtN3 genes. Disruption of the crtN1/ald genes or the promoter driving expression of the crtN1/ald/crtN2 gene cluster created various non-pigmented mutants ("white mutants") more suitable for $C_{40}$ carotenoid production (U.S. Ser. No. 10/997,844).

Transformation of C1 Metabolizing Bacteria

Electroporation has been used successfully for the transformation of: *Methylobacterium extorquens* AM1 (Toyama, H., et al., *FEMS Microbiol. Lett.* 166: 1-7 (1998)), *Methylophilus methylotrophus* AS1 (Kim, C. S., and Wood, T. K., *Appl. Microbiol. Biotechnol.* 48: 105-108 (1997)), and *Methylobacillus* sp. strain 12S (Yoshida, T., et al., *Biotechnol. Lett.*, 23: 787-791 (2001)). Extrapolation of specific electroporation parameters from one specific C1 metabolizing utilizing organism to another may be difficult, however, as is well to known to those of skill in the art.

Bacterial conjugation, relying on the direct contact of donor and recipient cells, is frequently more readily amenable for the transfer of genes into C1 metabolizing bacteria. Simplistically, this bacterial conjugation process involves mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1.) Double-strand plasmid DNA is nicked at a specific site in oriT; 2.) A single-strand DNA is released to the recipient through a pore or pilus structure; 3.) A DNA relaxase enzyme cleaves the double-strand DNA at oriT and binds to a release 5' end (forming a relaxosome as the intermediate structure); and 4.) Subsequently, a complex of auxiliary proteins assemble at oriT to facilitate the process of DNA transfer.

Alternatively, a "triparental" conjugation is required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving C1 metabolizing bacteria include the work of: Stolyar et al. (*Mikrobiologiya* 64(5): 686-691 (1995)); Motoyama et al. (*Appl. Micro. Biotech.* 42(1): 67-72 (1994)); Lloyd et al. (*Archives of Microbiology* 171(6): 364-370 (1999)); and Odom et al. (U.S. Ser. No. 09/941,947).

Recombinant Expression—Plants

Plants and algae are also known to produce carotenoid compounds. The nucleic acid fragments of the instant invention may be used to create transgenic plants having the ability to express the microbial protein. Preferred plant hosts will be any variety that will support a high production level of the instant proteins. Suitable green plants will include but are not limited to soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa,* L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include but not limited to commercially significant hosts such as *Spirulina, Haemotacoccus,* and *Dunaliela*. Production of the carotenoid compounds may be accomplished by first constructing chimeric genes of present invention in which the coding regions are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences or the present invention should be capable of promoting expression of the present gene product. High level plant promoters that may be used in this invention include the promoter of the small subunit (ss) of the ribulose-1,5-bisphosphate carboxylase from example from soybean (Berry-Lowe et al., *J. Molecular and App. Gen.*, 1: 483-498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29-38; Coruzzi, G. et al., *The Journal of Biological Chemistry*, 258: 1399 (1983), and Dunsmuir, P. et al., *Journal of Molecular and Applied Genetics*, 2: 285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4: 2411-2418 (1985); De Almeida et al., *Mol. Gen. Genetics* 218: 78-86 (1989)), and thus that multiple events must be screened in order to obtain lines displaying the desired expression level and pattern. Such screening may be accomplished by Southern analysis of DNA blots (Southern, *J. Mol. Biol.* 98, 503, (1975)), Northern analysis of mRNA expression (Kroczek, R. A., *J. Chromatogr. Biomed. Appl.*, 618 (1-2): 133-145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell* 56: 247-253 (1989)), signal sequences or sequences encoding endoplasmic reticulum localization (Chrispeels, J. J., *Ann. Rev. Plant Phys. Plant Mol. Biol.* 42: 21-53 (1991)), or nuclear localization signals (Raikhel, N., *Plant Phys.* 100: 1627-1632 (1992)) added and/or with targeting sequences that are already present removed. While the references cited give examples of each of these, the list is not exhaustive and more targeting signals of utility may be discovered in the future that are useful in the invention.

In vitro Bio-Conversion of Carotenoids

Alternatively, it is possible to carry out the bioconversions of the present application in vitro. Where substrates for the present CrtO ketolases are not synthesized endogenously by the host cell it will be possible to add the substrate exogenously. In this aspect, the suitable carotenoid substrate may be solubilized with mild detergent (e.g., DMSO) or mixed with phospholipid vesicles. To assist in transport into the cell, the host cell may optionally be permeabilized with a suitable solvent such as toluene. Methods for this type of in vitro bio-conversion of carotenoid substrates has basis in the art (see for example: Hundle, B. S., et al., *FEBS*, 315: 329-334 (1993); and Bramley, P. M., et al., *Phytochemistry*, 26: 1935-1939 (1987)).

Protein Engineering CrtO Ketolases

The present CrtO ketolases were protein engineered using a combination of error-prone PCR ((Melnikov et al., *Nucleic Acids Research*, 27(4): 1056-1062 (1999); Leung et al., *Techniques*, 1: 11-15 (1989); and Zhou et al., *Nucleic Acids Res.* 19: 6052-6052 (1991)) and a gene shuffling technique ("recombinogenic extension method using unpaired primers"; (U.S. Ser. No. 10/374,366; hereby incorporated by reference). It is contemplated that the present crtO genes may be further engineered to produce gene products having further enhanced or altered activity. Various methods are known for mutating a native gene sequence to produce a gene product with altered or enhanced activity including, but not limited to: 1.) error-prone PCR; 2.) site-directed mutagenesis (Coombs et al., *Proteins* (1998), pp 259-311, 1 plate. Angeletti, Ruth Hogue, Ed., Academic: San Diego, Calif.); and 3.) "gene-shuffling" (U.S. Pat. No. 5,605,793; U.S. Pat. No. 5,811,238; U.S. Pat. No. 5,830,721; and U.S. Pat. No. 5,837,458 or any similar means of promoting recombinogenic activity between nucleic acids (U.S. Ser. No. 10/374,366)).

The method of gene shuffling is particularly attractive due to its facile implementation, high rate of mutagenesis, and ease of screening. The process of gene shuffling involves the restriction endonuclease cleavage of a gene of interest into fragments of specific size in the presence of additional populations of DNA fragments having regions of similarity or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonucleases well known in the art (Maniatis, supra). In addition to the instant microbial sequences, populations of fragments that are hybridizable to all or portions of the microbial sequence may be added. Similarly, a population of fragments that are not hybridizable to the instant sequences may also be added. Typically these additional fragment populations are added in about a 10 to 20-fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times.

Preferably the cycle is repeated from about 2 to 50 times, more preferably the sequence is repeated from 10 to 40 times. The resulting nucleic acid is a larger double-stranded polynucleotide ranging from about 50 bp to about 100 kB and may be screened for expression and altered activity by standard cloning and expression protocols (Maniatis, supra).

Furthermore, a hybrid protein can be assembled by fusion of functional domains using the gene shuffling (exon shuffling) method (Nixon et al., *Proc. Natl. Acad. Sci.,* 94: 1069-1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

In addition to the methods exemplified above (which are designed to directly mutagenize the genes encoding CrtO ketolases), traditional methods of creating mutants could be utilized for the purposes described herein. For example, wild-type cells having CrtO ketolase activity may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm, where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible; but this range is generally not as effective as the short wave UV light, unless used in conjunction with various activators (such as psoralen dyes) that interact with the DNA. Likewise, mutagenesis with chemical agents is also effective for generating mutants and commonly used substances include chemicals that affect nonreplicating DNA (such as $HNO_2$ and $NH_2OH$), as well as agents that affect replicating DNA (such as acridine dyes, notable for causing frameshift mutations). Specific methods for creating mutants using radiation or chemical agents are well documented in the art. See, for example, Brock (supra) or Deshpande (supra).

Irrespective of the method of mutagenesis, a gene may be evolved such that the enzyme has an increase in ketolase activity. The increase in ketolase activity can be measured using a variety of techniques known in the art. In the present invention, a simple measurement of ketocarotenoid production in the presence of excess substrate (i.e. β-carotene) under essentially identical reaction conditions will typically be suitable to identify enzymes capable of providing a higher percentage yield of a ketocarotenoid.

Preferred Codon Usage Table for Methylomonas sp. 16a

The preferred codon usage for *Methylomonas* sp. 16a (ATCC PTA-2402) has previously been reported (U.S. Ser. No. 10/997,844). Briefly, the genome of *Methylomonas* sp. 16a was sequenced and 201 highly-expressed Methylomonas genes, according to microarray analysis, were used to determine the preferred codon usage profile in *Methylomonas* sp. 16a, which is shown in Table 1. The coding regions of these genes, comprising 164,751 bp, were translated by the Editseq program of DNASTAR to the corresponding 54,917 amino acids. The column titled "Number" refers to the number of times a given codon encodes a particular amino acid in the sample of 54,917 amino acids. The column titled "Fraction" refers to the frequency that a given codon encodes a particular amino acid. The stop codons were not included in the coding regions for tabulation.

TABLE 1

Preferred Codon Usage Table for *Methylomonas* sp. 16a

| Amino Acid | Codon | Number | Fraction |
|---|---|---|---|
| Gly | GGG | 288.00 | 0.07 |
| Gly | GGA | 300.00 | 0.07 |
| Gly | GGU | 1168.00 | 0.27 |
| Gly | GGC | 2541.00 | 0.59 |
| Glu | GAG | 966.00 | 0.28 |
| Glu | GAA | 2514.00 | 0.72 |
| Asp | GAU | 1435.00 | 0.46 |
| Asp | GAC | 1712.00 | 0.54 |
| Val | GUG | 1287.00 | 0.32 |
| Val | GUA | 508.00 | 0.13 |
| Val | GUU | 717.00 | 0.18 |
| Val | GUC | 1450.00 | 0.37 |
| Ala | GCG | 1576.00 | 0.31 |
| Ala | GCA | 607.00 | 0.12 |
| Ala | GCU | 658.00 | 0.13 |
| Ala | GCC | 2279.00 | 0.45 |
| Lys | AAG | 1055.00 | 0.35 |
| Lys | AAA | 1988.00 | 0.65 |
| Asn | AAU | 877.00 | 0.40 |
| Asn | AAC | 1317.00 | 0.60 |
| Met | AUG | 1443.00 | 1.00 |
| Ile | AUA | 301.00 | 0.09 |
| Ile | AUU | 933.00 | 0.28 |
| Ile | AUC | 2122.00 | 0.63 |
| Thr | ACG | 544.00 | 0.19 |
| Thr | ACA | 263.00 | 0.09 |
| Thr | ACU | 380.00 | 0.13 |
| Thr | ACC | 1738.00 | 0.59 |
| Trp | UGG | 600.00 | 1.00 |
| Cys | UGU | 151.00 | 0.24 |
| Cys | UGC | 474.00 | 0.76 |
| Tyr | UAU | 779.00 | 0.52 |
| Tyr | UAC | 723.00 | 0.48 |
| Phe | UUU | 793.00 | 0.38 |
| Phe | UUC | 1308.00 | 0.62 |
| Ser | AGU | 317.00 | 0.10 |
| Ser | AGC | 868.00 | 0.27 |
| Ser | UCG | 733.00 | 0.23 |
| Ser | UCA | 318.00 | 0.10 |
| Ser | UCU | 291.00 | 0.09 |
| Ser | UCC | 701.00 | 0.22 |
| Arg | AGG | 186.00 | 0.06 |
| Arg | AGA | 287.00 | 0.09 |
| Arg | CGG | 411.00 | 0.13 |
| Arg | CGA | 250.00 | 0.08 |
| Arg | CGU | 693.00 | 0.22 |
| Arg | CGC | 1292.00 | 0.41 |
| Gln | CAG | 893.00 | 0.40 |
| Gln | CAA | 1345.00 | 0.60 |
| His | CAU | 635.00 | 0.51 |
| His | CAC | 600.00 | 0.49 |
| Leu | UUG | 1825.00 | 0.38 |
| Leu | UUA | 319.00 | 0.07 |
| Leu | CUG | 1980.00 | 0.41 |
| Leu | CUA | 172.00 | 0.04 |
| Leu | CUU | 221.00 | 0.05 |
| Leu | CUC | 277.00 | 0.06 |
| Pro | CCG | 1104.00 | 0.44 |
| Pro | CCA | 443.00 | 0.18 |
| Pro | CCU | 441.00 | 0.18 |
| Pro | CCC | 520.00 | 0.21 |

The preferred codon usage for *Methyolmonas* was used to codon optimize all (or at least a portion of) the coding sequence of the crtO ketolase genes used for error-prone PCR (crtO303, SEQ ID NO: 4; crtO319, SEQ ID NO: 3; and crtO320 (SEQ ID NO: 6).

Accordingly, using the above described methods a number of mutants of crtO ketolase genes were created and screened for activity. Useful mutants had at least one of the following mutations based on the crtO ketolase from *Rhodococcus erythropolis* AN12 (SEQ ID NO:2):

a) a replacement of threonine at amino acid position 121 with alanine;
b) a replacement of methionine at amino acid position 142 with leucine;
c) a replacement of alanine at amino acid position 164 with valine;
d) a replacement of isoleucine at amino acid position 2 with valine;
e) a replacement of threonine at amino acid position 304 with lysine;
f) a replacement of arginine at amino acid position 339 with glutamine;
g) a replacement of arginine at amino acid position 519 with tryptophan; and
h) a replacement of glutamine at amino acid position 524 with leucine or arginine.

A preferred mutant had the following mutations based on the crtO ketolase from *Rhodococcus erythropolis* AN12 (SEQ ID NO:2):

a) a replacement of methionine at amino acid position 142 with leucine; and
b) a replacement of alanine at amino acid position 164 with valine.

The specific mutant amino acid sequences corresponding are given here in as SEQ ID NO: 14, 16, 18, 20, 22, 24, 26, 28, 30, 32, 34, 36, 38, 40, 42, 44, 46, 48, 50, and 52.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Maniatis (supra), Silhavy et al. (supra), and Ausubel et al. (supra).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Brock (supra). All reagents, restriction enzymes and materials used for the growth and maintenance of bacterial cells were obtained from Aldrich Chemicals (Milwaukee, Wis.), DIFCO Laboratories/BD Diagnostics (Sparks, Md.), Promega (Madison, Wis.), New England Biolabs (Beverly, Mass.), GIBCO/BRL Life Technologies (Carlsbad, Calif.), or Sigma Chemical Company (St. Louis, Mo.) unless otherwise specified.

XL1-Blue MRF' Electroporation-Competent *E. coli* cells (Catalog No. 200158) were purchased from Stratagene (La Jolla, Calif.).

PCR reactions were run on GeneAMP PCR System 9700 using Amplitaq or Amplitaq Gold enzymes (PE Applied Biosystems, Foster City, Calif.), unless otherwise specified. The cycling conditions and reactions were standardized according to the manufactures' instructions. The meaning of abbreviations is as follows: "min" means minute(s), "h" means hour(s), "µL" means microliter, "mL" means milliliters, "L" means liters, "cm" means centimeters, "nm" means nanometers, "mM" means millimolar, "kb" means kilobases, and "kV" means kilovolts.

Example 1

Making Mutant libraries

Error-Prone PCR

The gene encoding the carotene ketolase enzyme (CrtO) from *Rhodococcus erythropolis* AN12 was cloned by PCR (U.S. Ser. No. 10/209,372; hereby incorporated by reference). The coding sequence of the wild-type *R. erythropolisAN12* crtO is approximately 1600 bp (SEQ ID NO: 1) encoding the amino acid sequence represented by SEQ ID NO: 2. It should be noted that the start codon for all of the present crtO coding sequences was changed from GTG (as found in the wild type *R. erythropolis* AN12 coding sequence) to ATG to facilitate expression. Three constructs, pDCQ319, pDCQ303 and pDCQ320 were created and used as templates for error-prone PCR.

Briefly, plasmids pDCQ303, pDCQ319, and pDCQ320 were prepared by cloning variants of crtO genes into the unique MfeI site of pDCQ301 downsteam of crtE gene, which contains the crtEYIB genes from *Pantoea stewartii* (ATCC8199) in the pBHR1 vector (MoBiTec GmbH, Goettingen, Germany) for β-carotene synthesis. The unique MfeI site of pDCQ301 was introduced in the junction of crtE and crtY genes when removing the crtX gene in the original crtEXYIB cluster. The three plasmids pDCQ303, pDCQ319 and pDCQ320 all contain crtEOYIB gene cluster cloned under the Pcat promoter in pBHR1 vector. The crtO gene in each construct was confirmed to be expressed in the same orientation as the crtEYIB genes.

Plasmid pDCQ319 contained a codon modified *R. erythropolis* AN12 crtO ("crtO319"). The entire codon usage of crtO319 (SEQ ID NOs: 3) was optimized for *Methylomonas* sp. 16a (Table 1). The crtO319 gene was synthesized by GenScript Corp. (Scotch Plains, N.J.).

Plasmid pDCQ303 also contained a partially codon optimized version of the *R. erythropolis* AN12 crtO denoted as "crtO303" (SEQ ID NOs: 4 and 5). CrtO303 is different from crtO319 in that only several codons on the 5'- and 3'-ends of crtO303 introduced by PCR primers were optimized for *Methylomonas* 16a. Compared with natural crtO gene product from *Rhodococcus erythropolis* AN12, crtO303 contains three additional amino acids (Met-Ala-Leu) at its N-terminus (SEQ ID NO: 5).

Plasmid pDCQ320 contained a partially codon optimized version of *R. erythropolis* AN12 crtO denoted as "crtO320". The coding sequence of crtO320 (SEQ ID NO: 6) construct is the same as the coding sequence for crtO303 except that the three additional amino acids (Met-Ala-Leu) have been removed from the N-terminus.

The various crtO genes (crtO303, crtO319, and crtO320) were removed from the construct using MfeI and XbaI digestion. Three random mutant libraries targeting the entire crtO gene were made for all three constructs. The following primers were used to amplify the inserts by error-prone PCR:

```
for pDCQ319:
crtO-For
(5'-AGCCAATTGAAGGAGGAATAAACCATG-3')    (SEQ ID NO:7)
crtO-Rev
(5'-GCGAATTCCTCTAGATTAGCTACGGCT-3')    (SEQ ID NO:8)

for pDCQ303:
crtO900-For
5'-TAACAATTGAAGGAGGAATAAACCATGGCC-3'   (SEQ ID NO:9)
crtO303-Rev
5'-GCGAATTCCTCTAGATCACGAGCGGCTCGA-3'   (SEQ ID NO:10)

for pDCQ320:
320-F1
5'-GCCATTAGCCAGACCGGCA-3'              (SEQ ID NO:11)
320-R1
5'-GCGCCTGGCCAGTGAACA-3'               (SEQ ID NO:12)
```

A Clontech mutagenesis kit (Clontech Laboratories, Inc., Palo Alto, Calif.) was used for performing error-prone PCR. The following conditions described in Table 2 were used for preparing the error-prone PCR reaction mixture:

TABLE 2

Condition for Error-prone PCR using Clontech Mutagenesis Kit

| | Volumes (µL) | |
| --- | --- | --- |
| | Condition-1 | Condition-2 |
| PCR grade water | 38 | 37 |
| 10x AdvanTaq Plus Buff. | 5 | 5 |
| MnSO$_4$ (8 mM) | 2 | 3 |
| dGTP (2 mM) | 1 | 1 |
| 50x Diversify dNTP Mix | 1 | 1 |
| Primer mix | 1 | 1 |
| Template DNA | 1 | 1 |
| AdvanTaq Plus Polym. | 1 | 1 |

Condition-1 was used for crtO319 and crtO303 libraries, and Condition-2 was for the crtO320 library. The thermal cycling reaction was carried out according to the manufacturer's instructions. The 1.6 kb PCR products were digested with MfeI and XbaI, and ready for ligation. The mutants exhibiting red-orange color found from the crtO320 mutant library were further mutagenezied, and the resulting 1.6 kb DNA fragments were digested with MfeI and XbaI.

Mutant Library Construction

To prepare the vector, the template plasmids (pDCQ303, pDCQ319 and pDCQ320) were digested with MfeI and XbaI to remove the crtO insert. The digested vector was purified from the agarose gel. The Mfe I and XbaI-digested error-prone PCR products were then ligated with the MfeI/XbaI-digested vectors. After ethanol precipitation, the ligation mixture was ready for the transformation.

The ligation mixture was first transformed into XL1-Blue MRF' Electroporation-Competent E. coli cells (Stratagene, La Jolla, Calif.) by electroporation. After growing the mutant library cells in liquid or Agar LB containing kanamycin, the plasmids were isolated from the library cells.

E. coli strain WS210 was used for the mutant library construction. E. coli strain WS210 contains the same chromosomal modifications found in E. coli strain WS208 (ATCC PTA-4823; U.S. Ser. No. 10/735,442, hereby incorporated by reference), a strain capable of producing up to 6000 ppm β-carotene. WS210 is genetically identical to WS208 except for the fact that the β-carotene expression plasmid found in WS208 (pDCQ108) has been removed.

First, the electroporation-competent WS210 cells were made. Overnight cell culture (2.5 mL) was added to 500 mL of LB broth in a 2-L sterile flask. The culture was incubated at 37° C. on the shaker until the OD$_{600nm}$ reached 0.5 to 0.8. The cells were then incubated on ice for 10 min, followed by the centrifugation at 4° C. for 10 min. After washing the cell pellet once with 500 mL ice-cold water, the cells were resuspended in 1-2 mL of 10% ice-cold glycerol. Aliquots (50 µL) were made in sterile Eppendorf tubes and immediately frozen on dry ice. The competent cells were stored at −80° C. To do the transformation, 1 µL of mutant library plasmids isolated from E. coli XL1-Blue cells was added to 40 µL of competent cells, and the sample was transferred into electroporation cuvette with 0.1 cm gap. The voltage used for electroporation was 1.7 kV/cm. The cells were plated onto LB plates in the presence of kanamycin (50 µg/mL) and incubated overnight at 37° C. The mutant colonies were ready for high throughput screening.

Dna Sequence Analysis of the Mutant Libraries

Ten mutant colonies from each library were randomly picked for DNA sequencing analyses. The mutant genes were sequenced on an ABI 377 automated sequencer (Applied Biosystems, Foster City, Calif.), and the data managed using Vector NTI Version 7.0 program (InforMax, Inc., Bethesda, Md.). Most of the mutations were base substitution. The frequency of deletion and insertion mutations in the mutant libraries was very low. Many types of base substitution were present in these mutants, indicating that there was no bias for the mutation type. The mutation rate was 1-5 point mutations per kb. The enzyme activity distribution was estimated by the color of the mutant colonies (see Example 2). The results showed that about 40-60% of the mutants in the library were active.

Example 2

Screening the Mutant Libraries and Identifying the Hits

Cells producing β-carotene are yellow, and the color of the cells producing canthaxanthin are red-orange. The cells that make different amounts of canthaxanthin show slightly different coloration. Therefore, the mutant colonies that produce different amounts of canthaxanthin can be distinguished by the eye. Approximately 20,000-150,000 mutant colonies from each library were visually screened. The putative "hits" were streaked on Agar plates, and ranked based on their pigmentation.

HPLC analysis was used to confirm the percentage of canthaxanthin produced. Briefly, Cells were grown in LB with 50 µg/mL kanamycin at 37° C. shaking overnight. Cells were pelleted by centrifugation at 4000 g for 15 min, and the cell pellets were extracted with 10 mL acetone. The extraction was dried under nitrogen and redisolved in 1-2 mL of acetone. The extraction was filtered with an Acrodisc® CR25 mm syringe filter (Pall Corporation, Ann Arbor, Mich.). It was then analyzed using an Agilent Series 1100 LC/MSD Si (Agilent, Foster City, Calif.).

Sample (20 µL) was loaded onto a 150 mm×4.6 mm ZORBAX C18 (3.5 µm particles) column (Agilent Technologies, Inc.). The column temperature was kept at 40° C. The flow rate was 1 mL/min, while the solvent running program used was

- 0-2 min: 95% buffer A and 5% buffer B;
- 2-10 min: linear gradient from 95% buffer A and 5% buffer B to 60% buffer A and 40% buffer B;
- 10-12 min: linear gradient from 60% buffer A and 40% buffer B to 50% buffer A and 50% buffer B;
- 12-18 min: 50% buffer A and 50% buffer B; and,
- 18-20 min: 95% buffer A and 5% buffer B.

Buffer A was 95% acetonitrile and 5% dH₂O; buffer B was 100% tetrahydrofuran.

The peaks were identified based on comparisons of retention time, absorption spectra and molecular weight with those of the synthetic standards purchased from CaroteNature (Lupsingen, Switzerland). The percentage of canthaxanthin was calculated as the area of the canthaxanthin peak divided by the area of the total carotenoid peaks.

Table 3 summarizes the follow-up assay results for the hits:

TABLE 3

Confirmation results of the hits

| Strain | Percentage Yield of Canthaxanthin |
|---|---|
| CrtO319(starting gene) | 4.05 |
| 319M3022 | 14.9 |
| CrtO303(starting gene) | 5.9 |
| 303M3044 | 16.0 |
| CrtO320(starting gene) | 20.0 |
| 320M4019 | 46.3 |
| 320M4018 | 44.4 |
| 320M4006 | 43.4 |
| 320M4007 | 43.7 |
| 320M4027 | 39.5 |
| 320M4020 | 43.1 |
| 320M4036 | 41.2 |
| 320M4023 | 40.1 |
| 320M4009 | 45.8 |
| 320M4032 | 36.7 |
| 320SHU019 | 91.4 |
| 320SHU001 | 88.9 |
| 320SHU017 | 88.9 |
| 320SHU016 | 78.4 |
| 320SHU015 | 68.3 |
| 320SHU008 | 59.0 |
| 320SHU022 | 57.7 |
| 320SHU004 | 55.7 |

The cells were grown for 75 h at 30° C. in LB medium in the presence of kanamycin (50 µg/mL).

Table 3 shows that the percentage yield of canthaxanthin for the mutant gene products has been greatly improved. For example, compared with the starting gene crtO319, the mutant 319M3022 gene product showed a significant increase in percentage yield of canthaxanthin. Similar results were also obtained for the mutant (303M3044) from the crtO303 library. Several mutants from crtO320 library showed more than 40% of canthaxathin yield. Many mutants created using error-prone PCR ("first round mutants") exhibited a significant improvement in canthaxanthin yield. A second round of mutagenesis was performed using a gene shuffling technique in order to further improve canthaxanthin yield (U.S. Ser. No. 10/374,366). Many of the mutants (320SHU001-320SHU022) made from the improved first round mutants showed a significant improvement for their percentage yield of canthaxanthin. The mutants 320SHU001 and 320SHU019 exhibit an improvement in the percentage of canthaxanthin yield of approximately 90% yield (Table 3).

Under the current screening system, the performance of crtO gene product has significantly been improved.

Example 3

DNA Sequence Analysis of the Mutant Genes

The mutant genes were sequenced on an ABI377 automated sequencer (Applied Biosystem, Foster City, Calif.), and the data managed using Vector NTI program (InforMax, Inc., Bethesda, Md.). Analysis of the mutants, followed by comparison with the wild type gene, indicated that the mutant genes contained the following point mutations:

TABLE 4

DNA Sequence Analysis of Mutant Genes

| Strain (crtO NT and AA SEQ ID Nos.) | Mutations |
|---|---|
| 319M3022 (SEQ ID NOs. 13 and 14) | GCC(Ala3) to ACC(Thr) |
| 303M3044 (SEQ ID NOs. 15 and 16) | AGC(Ser5) to CGC(Arg)<br>ACG(Thr498) to ACA(Thr) |
| 320M4006 (SEQ ID NOs. 17 and 18) | GCG(Ala16) to GCA(Ala)<br>TCG(Ser449) to ACG(Thr) |
| 320M4007 (SEQ ID NOs. 19 and 20) | CTC(Leu17) to CTT(Leu)<br>GCA(Ala24) to GCT(Ala)<br>TGC(Cys112) to TAC(Tyr)<br>GCG(Ala252) to ACG(Thr)<br>CAG(Gln524) to CGG(Arg) |
| 320M4009 (SEQ ID NOs. 21 and 22) | AGC(Ser2) to AGA(Arg)<br>ACG(Thr37) to ATG(Met)<br>CGA(Arg117) to CGT(Arg)<br>CCC(Pro444) to CCA(Pro)<br>AGT(Ser505) to AGC(Ser) |
| 320m4018 (SEQ ID NOs. 23 and 24) | CGA(Arg117) to CGT(Arg)<br>GTC(Val133) to GTA(Val)<br>ACA(Thr147) to TCA(Ser)<br>CTG(Leu224) to CTT(Leu)<br>TCA(Ser464) to ACA(Thr)<br>CCC(Pro497) to CCT(Pro) |
| 320M4019 (SEQ ID NOs. 25 and 26) | AGC(Ser2) to AAC(Asn)<br>AGT(Ser67) to AAT(Asn)<br>TTT(Phe145) to TCT(Ser)<br>CGA(Arg302) to CGG(Arg)<br>GAC(Asp446) to GGC(Gly) |
| 320M4020 (SEQ ID NOs. 27 and 28) | ATG(Met142) to TTG(Leu)<br>GCG(Ala164) to GTG(Val)<br>ATC(Ile283) to GTC(Val) |
| 320M4023 (SEQ ID NOs. 29 and 30) | AGC(Ser2) to AGA(Arg)<br>GAC(Asp36) to GAT(Asp)<br>GAT(Asp293) to GGT(Gly) |
| 320M4027 (SEQ ID NOs. 31 and 32) | TCC(Ser331) to TCT(Ser)<br>CGG(Arg519) to TGG(Trp) |
| 320M4031 (SEQ ID NOs. 33 and 34) | GAA(Glu208) to GAG(Glu)<br>ACG(Thr304) to AAG(Lys)<br>CCT(Pro369) to CCC(Pro)<br>GCC(Ala509) to GCT(Ala)<br>CAG(Gln524) to CTG(Leu)<br>TCG(Ser529) to TGG(Trp) |
| 320M4032 (SEQ ID NOs. 33 and 34) | GCG(Ala16) to GGG(Gly)<br>TTG(Leu240) to CTG(Leu)<br>GAA(Glu276) to GAG(Glu)<br>TTT(Phe428) to TAT(Tyr) |

TABLE 4-continued

DNA Sequence Analysis of Mutant Genes

| Strain (crtO NT and AA SEQ ID Nos.) | Mutations |
|---|---|
| 320M4036 (SEQ ID NOs. 35 and 36) | AGC(Ser2) to AGT(Ser)<br>GCA(Ala180) to GCG(Ala)<br>GCG(Ala252) to ACG(Thr)<br>TCG(Ser264) to CCG(Pro)<br>CAT(His407) to CAA(Gln) |
| 320SHU001 (SEQ ID NOs. 37 and 38) | GCG(Ala16) to GCA(Ala)<br>GCA(Ala24) to GCC(Ala)<br>ATG(Met142) to TTG(Leu)<br>GCG(Ala164) to GTG(Val)<br>ACG(Thr304) to AAG(Lys)<br>GTG(Leu477) to TTG(Leu)<br>CGG(Arg519) to TGG(Trp) |
| 320SHU004 (SEQ ID NOs. 39 and 40) | GCG(Ala16) to GCA(Ala)<br>TCC(Ser331) to TCT(Ser)<br>CGG(Arg519) to TGG(Trp) |
| 320SHU008 (SEQ ID NOs. 41 and 42) | GCG(Ala16) to GCA(Ala)<br>GCA(Ala24) to GCC(Ala)<br>GTC(Val131) to GTT(Val)<br>ATG(Met142) to TTG(Leu)<br>GCG(Ala164) to GTG(Val)<br>ATC(Ile283) to GTC(Val) |
| 320SHU015 (SEQ ID NOs. 43 and 44) | GCG(Ala16) to GCA(Ala)<br>TCG(Ser152) to TTG(Leu)<br>TCC(Ser331) to TCT(Ser)<br>CGG(Arg519) to TGG(Trp) |
| 320SHU016 (SEQ ID NOs. 45 and 46) | GCG(Ala16) to GCA(Ala)<br>GCA(Ala24) to GCC(Ala)<br>ACA(Thr121) to GCA(Ala)<br>ATG(Met142) to TTG(Leu)<br>GCG(Ala164) to GTG(Val)<br>ATC(Ile283) to GTC(Val)<br>GCC(Ala509) to GCT(Ala)<br>CAG(Gln524) to CTG(Leu) |
| 320SHU017 (SEQ ID NOs. 47 and 48) | GCG(Ala16) to GCA(Ala)<br>GCA(Ala24) to GCC(Ala)<br>ATG(Met142) to TTG(Leu)<br>GCG(Ala164) to GTG(Val)<br>ATC(Ile283) to GTC(Val)<br>CGG(Arg519) to TGG(Trp) |
| 320SHU019 (SEQ ID NOs. 49 and 50) | GCG(Ala16) to GCA(Ala)<br>GCA(Ala24) to GCC(Ala)<br>ATG(Met142) to TTG(Leu)<br>CTG(Leu161) to CTA(Leu)<br>GCG(Ala164) to GTG(Val)<br>CGG(Arg339) to CAG(Gln)<br>CCT(Pro369) to CCC(Pro)<br>CGG(Arg519) to TGG(Trp) |
| 320SHU022 (SEQ ID NOs. 51 and 52) | GCG(Ala16) to GCA(Ala)<br>GCA(Ala24) to GCC(Ala)<br>ATG(Met142) to TTG(Leu)<br>GCG(Ala164) to GTG(Val)<br>ATC(Ile283) to GTC(Val)<br>CAG(Gln524) to CGG(Arg) |

Except for the silent mutations, all the mutations were amino acid substitutions (Table 4). Some of the mutations have been observed in many mutants, such as ATG(Met142) to TTG(Leu), GCG(Ala164) to GTG(Val), ATC(Ile283) to GTC(Val), CGG(Arg519) to TGG(Trp), CAG(Gln524) to CGG(Arg), GCG(Ala16) to GCA(Ala), and GCA(Ala24) to GCC(Ala). In particular, two mutations (Met142 to Leu and Ala164 to Val) were found in many of the mutant exhibiting particularly high yields of ketocarcarotenoids, namely, 320SHU001, 320SHU008, 320SHU016, 320SHU017, 320SHU019, 320SHU022, and 320M4020 (Table 3). This observation suggests that these sites, and possibly the regions around these sites, are important regions for the crtO gene's improvement of bioproduction of canthaxanthin.

Example 4

Performance of Mutant Genes in *Methylomonas* sp. 16a

Some of the improved crtO mutants have been tested their performance in *Methylomonas* sp. 16a. The plasmids containing the mutant genes in WS210 host *E. coli* cells were incorporated into *Methylomonas* 16a through conjugation as described previously (U.S. 60/527,083; hereby incorporated by reference). *Methylomonas* sp. 16a (ATCC PTA-2402) cells expressing the mutant crtO genes were then grown in "BTZ-3" medium, and the amounts of canthaxanthin produced were analyzed by HPLC as previously described (Table 7). The standard gas phase for cultivation contains 25% methane in air.

Briefly, *Methylomonas* 16a strains expressing various crtO mutants on the present invention were grown in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking.

Nitrate liquid medium, also referred to herein as "defined medium" or "BTZ-3" medium was comprised of various salts mixed with Solution 1 as indicated below (Tables 5 and 6) or where specified the nitrate was replaced with 15 mM ammonium chloride. Solution 1 provides the composition for 100-fold concentrated stock solution of trace minerals.

TABLE 5

Solution 1*

| | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to an end volume of 1 L. Keep refrigerated.

TABLE 6

Nitrate liquid medium (BTZ-3)**

| | MW | Conc. (mM) | g per L |
|---|---|---|---|
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7) | 238.3 | | 50 mL |
| Solution 1 | | | 10 mL |

**Dissolve in 900 mL $H_2O$. Adjust to pH = 7, and add $H_2O$ to give 1 L. For agar plates: Add 15 g of agarose in 1 L of medium, autoclave, let cool down to 50° C., mix, and pour plates.

Table 7 summarizes the percentage yield of canthaxanthin in *Methylomonas* strains expressing the present crtO mutants:

TABLE 7

Percentage Yields of Canthaxanthin in *Methylomonas* sp. 16a

| Strain | Percentage yield of Canthaxanthin |
|---|---|
| CrtO319 (starting gene) | 3-9% |
| CrtO303 (starting gene) | 7-15% |
| CrtO320 (starting gene) | 15-21% |
| 320M4019 | 38-40% |
| 320SHU001 | 45-53% |
| 320SHU019 | 44-51% |

These results indicate that the performance of the mutant crtO genes of the present invention has been greatly improved when compared with the starting genes. However, the absolute percentage yield of canthaxanthin in *Methylomonas* 16a was generally less than that in *E. coli* (Table 3). There could be many reasons for this observation. For example, the fermentation condition was not optimized for these mutant crtO genes; or the microenvironment inside the cell was different between *E. coli* and *Methylomonas* 16a. Since the percentage yield of canthaxanthin in *E. coli* for some of the mutants (e.g. 320SHU001 and 320SHU019) has almost been optimized, the further improvement of these mutant genes should be carried out in *Methylomonas* 16a.

What is claimed is:

1. An isolated nucleic acid molecule encoding a polypeptide having carotenoid ketolase activity, the polypeptide having the amino acid sequence set forth in SEQ ID NO:2, wherein the polypeptide has an amino acid substitution selected from the group consisting of:
   a) a replacement of threonine at amino acid position 121 of SEQ ID NO:2 with alanine;
   b) a replacement of methionine at amino acid position 142 of SEQ ID NO:2 with leucine;
   c) a replacement of alanine at amino acid position 164 of SEQ ID NO:2 with valine;
   d) a replacement of isoleucine at amino acid position 283 of SEQ ID NO:2 with valine;
   e) a replacement of threonine at amino acid position 304 of SEQ ID NO:2 with lysine;
   f) a replacement of arginine at amino acid position 339 of SEQ ID NO:2 with glutamine;
   g) a replacement of arginine at amino acid position 519 of SEQ ID NO:2 with tryptophan;
   h) a replacement of glutamine at amino acid position 524 of SEQ ID NO:2 with leucine or arginine; and
   i) a combination thereof.

2. An isolated nucleic acid molecule encoding a polypeptide having carotenoid ketolase activity, the polypeptide having the amino acid sequence set forth in SEQ ID NO:2, wherein the polypeptide has an amino acid substitution selected from the group consisting of:
   a) a replacement of methionine at amino acid position 142 of SEQ ID NO:2 with leucine;
   b) a replacement of alanine at amino acid position 164 of SEQ ID NO:2 with valine; and
   c) a combination thereof.

3. An isolated nucleic acid molecule encoding a carotenoid ketolase enzyme having an amino acid sequence selected from the group consisting SEQ ID NO: 14, 16, 18, 20, 22, 24, 26, 28, 30, 32, 34, 36, 38, 44, 46, 48, 50, and 52.

4. The isolated nucleic acid molecule of claim 3 selected from the group consisting of SEQ ID NO: 13, 15, 17, 19, 21, 23, 25, 27, 29, 31, 33, 35, 37, 39, 41, 43, 45, 47, 49, and 51.

5. A chimeric gene comprising the isolated nucleic acid molecule of claims 1 or 3 operably linked to suitable regulatory sequences.

6. A transformed host cell comprising the isolated nucleic acid molecule of claims 1 or 3.

7. The transformed host cell of claim 6 wherein the host cell is selected from the group consisting of bacteria, yeast, filamentous fungi, algae, and green plants.

8. The transformed host cell of claim 7 wherein the host cell is selected from the group consisting of *Aspergillus, Trichoderma, Saccharomyces, Pichia, Phaffia, Candida, Hansenula, Salmonella, Bacillus, Acinectorbacter, Zymomonas, Agrobacterium, Erythrobacter, Chloroborium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Methanomonas, Synechococcus, Anabeana, Thiobacillus, Methanobacterium, Klebsiella*, and *Myxococcus*.

9. The transformed host cell of claim 8 wherein the host cell is selected from the group consisting of *Escherichia* and *Methylomonas*.

10. The transformed host cell of claim 9 wherein the host cell is selected from the group consisting of *Escherichia coli* and *Methylomonas* sp. 16a (ATCC PTA-2402).

11. The transformed host cell of claim 7 where the host cell is selected from the group consisting of soybean, rapeseed, pepper, sunflower, cotton, corn, tobacco, alfalfa, wheat, barley, oats, sorghum, rice, *Arabidopsis*, cruciferous vegetables, melons, carrots, celery, parsley, tomatoes, potatoes, strawberries, peanuts, grapes, sugar beets, sugar cane, beans, peas, rye, flax, hardwood trees, softwood trees, and forage grasses.

12. A method for the production of cyclic ketocarotenoid compounds comprising:
    a) providing a host cell which produces monocyclic or bicyclic carotenoids;
    b) transforming the host cell with the isolated nucleic acid molecule of either of claims 1 or 3 encoding a carotenoid ketolase enzyme;
    c) growing the transformed host cell of (b) under conditions whereby a cyclic ketocarotenoid is produced; and
    d) optionally isolating the ketocarotenoid produced in step c).

13. A method according to claim 12 wherein the cyclic ketocarotenoid compounds are selected from the group consisting of canthaxanthin, astaxanthin, adonixanthin, adonirubin, echinenone, 3-hydroxyechinenone, 3'-hydroxyechinenone, 4-keto-γ-carotene, 4-keto-rubixanthin, 4-ketotorulene, 3-hydroxy-4-keto-torulene, deoxyflexixanthin, and myxobactone.

14. A method according to claim 13 wherein the monocyclic or bicyclic carotenoids are selected from the group consisting of β-carotene, γ-carotene, zeaxanthin, rubixanthin, echinenone, and torulene.

15. A method according to claim 12 wherein the host cell is selected from the group consisting of bacteria, yeast, filamentous fungi, algae, and green plants.

16. A method according to claim 15 wherein the transformed host cell is selected from the group consisting of *Aspergillus, Trichoderma, Saccharomyces, Pichia, Phaffia, Candida, Hansenula, Salmonella, Bacillus, Acinectorbacter, Zymomonas, Agrobacterium, Erythrobacter, Chloroborium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Methanomonas, Synechococcus, Anabeana, Thiobacillus, Methanobacterium, Klebsiella*, and *Myxococcus*.

17. The method according to claim 16 wherein the transformed host cell is selected from the group consisting of *Escherichia* and *Methylomonas*.

18. A method according to claim 17 wherein the transformed host cell is selected from the group consisting of *Escherichia coli* and *Methylomonas* sp. 16a (ATCC PTA 2402).

19. A method according to claim 15 wherein the host cell is selected from the group consisting of soybean, rapeseed, pepper, sunflower, cotton, corn, tobacco, alfalfa, wheat, barley, oats, sorghum, rice, *Arabidopsis*, cruciferous vegetables, melons, carrots, celery, parsley, tomatoes, potatoes, strawberries, peanuts, grapes, sugar beets, sugar cane, beans, peas, rye, flax, hardwood trees, softwood trees, and forage grasses.

20. A method of altering cyclic ketocarotenoid biosynthesis in an organism comprising,
    (a) introducing into a host cell the isolated nucleic acid molecule of either of claims 1 or 3 encoding a carotenoid ketolase; and
    (b) growing the host cell of (a) under conditions whereby the carotenoid ketolase gene is expressed and cyclic ketocarotenoid biosynthesis is altered.

21. A method according to claim 20 wherein the isolated nucleic acid molecule encodes a polypeptide having the amino acid sequence selected from the group consisting of SEQ ID NO: 14, 16, 18, 20, 22, 24, 26, 28, 30, 32, 34, 36, 38, 44, 46, 48, 50, and 52.

22. A method according to claim 20 wherein the isolated nucleic acid molecule is upregulated.

23. A method according to claim 20 wherein the isolated nucleic acid molecule is over-expressed on a multicopy plasmid.

24. A method according to claim 20 wherein the isolated nucleic acid molecule is operably linked to an inducible or regulated promoter.

* * * * *